(12) United States Patent
Yang et al.

(10) Patent No.: US 9,561,274 B2
(45) Date of Patent: Feb. 7, 2017

(54) TREATMENT AND PREVENTION OF CANCER WITH HMGB1 ANTAGONISTS

(75) Inventors: Haining Yang, Honolulu, HI (US); Michele Carbone, Honolulu, HI (US); Marco E. Bianchi, Milan (IT)

(73) Assignee: UNIVERSITY OF HAWAII, Honolulu, HI (US)

( * ) Notice: Subject to any disclaimer, the term of this patent is extended or adjusted under 35 U.S.C. 154(b) by 42 days.

(21) Appl. No.: 14/123,607

(22) PCT Filed: Jun. 7, 2012

(86) PCT No.: PCT/US2012/041430
§ 371 (c)(1),
(2), (4) Date: Dec. 3, 2013

(87) PCT Pub. No.: WO2012/170742
PCT Pub. Date: Dec. 13, 2012

(65) Prior Publication Data
US 2014/0127134 A1    May 8, 2014

Related U.S. Application Data

(60) Provisional application No. 61/494,340, filed on Jun. 7, 2011, provisional application No. 61/502,275, filed on Jun. 28, 2011.

(51) Int. Cl.
*A61K 39/395* (2006.01)
*A61K 45/06* (2006.01)
*A61K 49/00* (2006.01)
*A61K 38/17* (2006.01)
*C07K 16/18* (2006.01)
*C07K 16/28* (2006.01)
*A61K 39/00* (2006.01)

(52) U.S. Cl.
CPC ....... *A61K 39/3955* (2013.01); *A61K 38/1709* (2013.01); *A61K 45/06* (2013.01); *A61K 49/00* (2013.01); *C07K 16/18* (2013.01); *C07K 16/28* (2013.01); *A61K 2039/505* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,474,893 A | 10/1984 | Reading |
| 4,612,132 A | 9/1986 | Wollenberg et al. |
| 4,676,980 A | 6/1987 | Segal et al. |
| 4,714,681 A | 12/1987 | Reading |
| 4,716,111 A | 12/1987 | Osband et al. |
| 4,741,900 A | 5/1988 | Alvarez et al. |
| 4,816,397 A | 3/1989 | Boss et al. |
| 4,816,567 A | 3/1989 | Cabilly et al. |
| 4,908,773 A | 3/1990 | Pantoliano et al. |
| 4,925,648 A | 5/1990 | Hansen et al. |
| 4,946,778 A | 8/1990 | Ladner et al. |
| 5,010,175 A | 4/1991 | Rutter et al. |
| 5,112,946 A | 5/1992 | Maione |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,288,514 A | 2/1994 | Ellman |
| 5,314,995 A | 5/1994 | Fell, Jr. et al. |
| 5,331,573 A | 7/1994 | Balaji et al. |
| 5,336,603 A | 8/1994 | Capon et al. |
| 5,349,053 A | 9/1994 | Landolfi |
| 5,359,046 A | 10/1994 | Capon et al. |
| 5,359,115 A | 10/1994 | Campbell et al. |
| 5,403,484 A | 4/1995 | Ladner et al. |
| 5,413,923 A | 5/1995 | Kucherlapati et al. |
| 5,420,328 A | 5/1995 | Campbell |
| 5,427,908 A | 6/1995 | Dower et al. |
| 5,436,850 A | 7/1995 | Eisenberg et al. |
| 5,447,851 A | 9/1995 | Beutler et al. |
| 5,474,981 A | 12/1995 | Leder et al. |
| 5,506,337 A | 4/1996 | Summerton et al. |
| 5,516,637 A | 5/1996 | Huang et al. |
| 5,519,134 A | 5/1996 | Acevedo et al. |
| 5,525,735 A | 6/1996 | Gallop et al. |
| 5,530,101 A | 6/1996 | Queen et al. |
| 5,539,083 A | 7/1996 | Cook et al. |
| 5,545,806 A | 8/1996 | Lonberg et al. |
| 5,549,974 A | 8/1996 | Holmes |
| 5,557,535 A | 9/1996 | Srinivasan et al. |
| 5,565,332 A | 10/1996 | Hoogenboom et al. |
| 5,569,588 A | 10/1996 | Ashby et al. |
| 5,569,825 A | 10/1996 | Lonberg et al. |
| 5,571,698 A | 11/1996 | Ladner et al. |
| 5,573,920 A | 11/1996 | Randle |
| 5,580,717 A | 12/1996 | Dower et al. |
| 5,585,089 A | 12/1996 | Queen et al. |
| 5,593,853 A | 1/1997 | Chen et al. |
| 5,595,756 A * | 1/1997 | Bally et al. .................. 424/450 |
| 5,601,819 A | 2/1997 | Wong et al. |
| 5,605,793 A | 2/1997 | Stemmer |
| 5,622,929 A | 4/1997 | Willner et al. |
| 5,624,821 A | 4/1997 | Winter et al. |
| 5,625,126 A | 4/1997 | Lonberg et al. |

(Continued)

FOREIGN PATENT DOCUMENTS

EP   0 239 400   9/1987
EP   0 367 166   5/1990

(Continued)

OTHER PUBLICATIONS

Vajdos et al. (J Mol Biol. Jul. 5, 2002;320(2):415-28 at 416).*

(Continued)

*Primary Examiner* — Brian J Gangle
*Assistant Examiner* — Andrea McCollum
(74) *Attorney, Agent, or Firm* — Knobbe, Martens, Olson & Bear, LLP

(57) ABSTRACT

Embodiments provided herewith relate to methods and compositions for treating or preventing cancer. More particularly, several embodiments are drawn to treating or preventing malignant mesothelioma with antagonists of high-mobility group box 1 (HMGB1).

13 Claims, 49 Drawing Sheets

(56) References Cited

U.S. PATENT DOCUMENTS

| | | |
|---|---|---|
| 5,633,425 A | 5/1997 | Lonberg et al. |
| 5,648,260 A | 7/1997 | Winter et al. |
| 5,658,727 A | 8/1997 | Barbas et al. |
| 5,658,759 A | 8/1997 | Bebbington |
| 5,661,016 A | 8/1997 | Lonberg et al. |
| 5,677,425 A | 10/1997 | Bodmer et al. |
| 5,698,426 A | 12/1997 | Huse |
| 5,714,350 A | 2/1998 | Co et al. |
| 5,733,743 A | 3/1998 | Johnson et al. |
| 5,750,753 A | 5/1998 | Kimae et al. |
| 5,780,225 A | 7/1998 | Wigler et al. |
| 5,789,208 A | 8/1998 | Sharon |
| 5,807,715 A | 9/1998 | Morrison et al. |
| 5,811,238 A | 9/1998 | Stemmer et al. |
| 5,814,318 A | 9/1998 | Lonberg et al. |
| 5,821,047 A | 10/1998 | Garrard et al. |
| 5,827,739 A | 10/1998 | Wilson et al. |
| 5,830,721 A | 11/1998 | Stemmer et al. |
| 5,834,252 A | 11/1998 | Stemmer et al. |
| 5,837,458 A | 11/1998 | Minshull et al. |
| 5,869,046 A | 2/1999 | Presta et al. |
| 5,873,052 A | 2/1999 | Sharaf |
| 5,879,936 A | 3/1999 | Bebbington et al. |
| 5,880,972 A | 3/1999 | Horlbeck |
| 5,884,230 A | 3/1999 | Srinivasan et al. |
| 5,885,573 A | 3/1999 | Bluestone et al. |
| 5,885,779 A | 3/1999 | Sadowski et al. |
| 5,885,793 A | 3/1999 | Griffiths et al. |
| 5,888,738 A | 3/1999 | Hendry |
| 5,916,771 A | 6/1999 | Hori et al. |
| 5,939,598 A | 8/1999 | Kucherlapati et al. |
| 5,969,108 A | 10/1999 | McCafferty et al. |
| 5,981,216 A | 11/1999 | Kenten et al. |
| 6,087,186 A | 7/2000 | Cargill et al. |
| 6,121,022 A | 9/2000 | Presta et al. |
| 6,165,745 A | 12/2000 | Ward et al. |
| 6,184,223 B1 | 2/2001 | Kahn et al. |
| 6,194,551 B1 | 2/2001 | Idusogie et al. |
| 6,277,375 B1 | 8/2001 | Ward |
| 6,335,163 B1 | 1/2002 | Sharon |
| 6,350,861 B1 | 2/2002 | Co et al. |
| 6,448,223 B1 | 9/2002 | Tracey et al. |
| 6,465,422 B1 | 10/2002 | Schmidt et al. |
| 6,468,533 B1 | 10/2002 | Tracey et al. |
| 6,555,651 B2 | 4/2003 | Stern et al. |
| 6,737,056 B1 | 5/2004 | Presta |
| 6,821,505 B2 | 11/2004 | Ward |
| 7,485,697 B2 | 2/2009 | Yamamoto et al. |
| 7,732,400 B2 | 6/2010 | Stern et al. |
| 2003/0060410 A1 | 3/2003 | Tracey et al. |
| 2003/0144201 A1 | 7/2003 | Tracey et al. |
| 2003/0190311 A1 | 10/2003 | Dall'Acqua et al. |
| 2004/0002587 A1 | 1/2004 | Watkins et al. |
| 2004/0005316 A1 | 1/2004 | Tracey et al. |
| 2004/0110833 A1 | 6/2004 | Fink et al. |
| 2004/0136979 A1 | 7/2004 | Bianchi et al. |
| 2004/0242481 A1 | 12/2004 | Bianchi et al. |
| 2006/0099207 A1* | 5/2006 | Wu .............. C07K 16/24 424/133.1 |
| 2006/0111287 A1* | 5/2006 | Bianchi ................ 514/12 |
| 2006/0188883 A1* | 8/2006 | Murray et al. .......... 435/6 |
| 2007/0286858 A1 | 12/2007 | Clancy et al. |
| 2008/0261258 A1 | 10/2008 | Smith et al. |
| 2008/0311122 A1 | 12/2008 | Wu et al. |
| 2009/0003640 A1 | 1/2009 | Burnett |
| 2009/0148453 A1* | 6/2009 | Newman et al. ........ 424/139.1 |
| 2009/0221542 A1 | 9/2009 | Wang et al. |
| 2010/0061987 A1 | 3/2010 | Wu et al. |
| 2010/0104589 A1 | 4/2010 | Govindan et al. |
| 2010/0129379 A1* | 5/2010 | Carpenter .......... A61K 9/0019 424/158.1 |
| 2010/0143349 A1 | 6/2010 | Hufton et al. |
| 2010/0152239 A1 | 6/2010 | Ulloa et al. |
| 2011/0091928 A1 | 4/2011 | Tamai et al. |
| 2011/0104174 A1 | 5/2011 | Strakhova et al. |
| 2014/0170685 A1 | 6/2014 | Yang et al. |

FOREIGN PATENT DOCUMENTS

| | | |
|---|---|---|
| EP | 0 396 387 | 11/1990 |
| EP | 0 413 622 | 2/1991 |
| EP | 0 439 095 | 7/1991 |
| EP | 0 519 596 | 12/1992 |
| EP | 0 592 106 | 4/1994 |
| EP | 1 176 195 | 1/2002 |
| WO | WO 84/03564 | 9/1984 |
| WO | WO 86/05807 | 10/1986 |
| WO | WO 88/07089 | 9/1988 |
| WO | WO 89/01036 | 2/1989 |
| WO | WO 89/12624 | 12/1989 |
| WO | WO 90/02809 | 3/1990 |
| WO | WO 91/00360 | 1/1991 |
| WO | WO 91/06570 | 5/1991 |
| WO | WO 91/09967 | 7/1991 |
| WO | WO 91/10737 | 7/1991 |
| WO | WO 91/10741 | 7/1991 |
| WO | WO 91/14438 | 10/1991 |
| WO | WO 91/19735 | 12/1991 |
| WO | WO 92/00091 | 1/1992 |
| WO | WO 92/01047 | 1/1992 |
| WO | WO 92/05793 | 4/1992 |
| WO | WO 92/08495 | 5/1992 |
| WO | WO 92/08802 | 5/1992 |
| WO | WO 92/18619 | 10/1992 |
| WO | WO 92/22324 | 12/1992 |
| WO | WO 93/11236 | 6/1993 |
| WO | WO 93/15199 | 8/1993 |
| WO | WO 93/15200 | 8/1993 |
| WO | WO 93/17715 | 9/1993 |
| WO | WO 93/20242 | 10/1993 |
| WO | WO 93/21232 | 10/1993 |
| WO | WO 93/25788 | 12/1993 |
| WO | WO 94/02935 | 2/1994 |
| WO | WO 95/15982 | 6/1995 |
| WO | WO 95/20401 | 8/1995 |
| WO | WO 96/04388 | 2/1996 |
| WO | WO 96/33735 | 10/1996 |
| WO | WO 96/34096 | 10/1996 |
| WO | WO 97/00271 | 1/1997 |
| WO | WO 97/33899 | 9/1997 |
| WO | WO 97/34631 | 9/1997 |
| WO | WO 97/34911 | 9/1997 |
| WO | WO 98/01879 | 1/1998 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 99/23105 | 5/1999 |
| WO | WO 99/54342 | 10/1999 |
| WO | WO 99/58572 | 11/1999 |
| WO | WO 00/42072 | 7/2000 |
| WO | WO 01/77137 | 10/2001 |
| WO | WO 02/060919 | 8/2002 |
| WO | WO 02/074337 | 9/2002 |
| WO | WO 03/035835 | 5/2003 |
| WO | WO 03/075957 | 9/2003 |
| WO | WO 2004/009618 | 1/2004 |
| WO | WO 2004/029207 | 4/2004 |
| WO | WO 2006/024547 | 3/2006 |
| WO | WO 2011/030334 | 3/2011 |
| WO | WO 2012/170740 | 12/2012 |

OTHER PUBLICATIONS

Brown et al. (J Immunol. May 1996;156(9):3285-91 at 3290 and Tables 1 and 2).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Guido et al (Curr Med Chem. 2008;15(1):37-46).*

(56) References Cited

OTHER PUBLICATIONS

Clark et al (J. Med. Chem., 2014, 57 (12), pp. 5023-5038).*
Ma (Modern Drug Discovery 2004, 7(6)).*
Bonovas et al (Anticancer Research. 28: 1857-1866 (2008)).*
Merler et al (Scand J Work Environ Health 1997;23(2):83-92).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
NCBI database entry for HMGB1 (downloaded Nov. 2, 2014 from http://www.ncbi.nlm.nih.gov/gene?term=(hmgb1[gene])%20 AND%20(Homo%20sapiens[orgn])%20AND%20alive [prop]%20NOT%20newentry[gene]&sort=weight).*
Neri (Anticancer Research. 32: 1005-1014 (2012).*
Guo et al (Cancer Biol Ther. May 2008;7(5):750-7. Epub May 20, 2008).*
Jube et al (Cancer Res Apr. 15, 2011 71; 2600).*
U.S. Appl. No. 08/081,577, filed Jun. 21, 1993, Campbell et al.
Alegre et al., 'A Non-Activating Humanized Anti-CD3 Monoclonal Antibody Retains Immunosuppressive Properties In Vivo', 1994, Transplantation 57:1537-1543.
Allen, F. H., et al., 'The Cambridge Crystallographic Data Centre: Computer-Based Search, Retrieval, Analysis and Display of Information', Acta Crystallogr., B35: 2331-2339 (1979).
Arnon et al., 'Monoclonal Antibodies for Immunotargeting of Drugs in Cancer Therapy', in Monoclonal Antibodies and Cancer Therapy, Reisfeld et al. (eds.), pp. 243-56 (Alan R. Liss, Inc. 1985).
Armour et al., 'Recombinant human IgG molecules lacking Fcγ receptor I binding and monocyte triggering activites', 1999, Eur J Immunol 29:2613-2624.
Armstrong et al., 'A Pahse I Study of Chemically Synthesized Verotoxin (Shiga-like Toxin) Pk-Trisaccharide Receptors Attached to Chromosorb for Preventing Hemolytic-Uremic Syndrome', J. Infectious Diseases 171:1042-1045 (1995).
Ashkenazi et al., 'Protection against endotoxic shock by a tumor necrosis factor receptor immunoadhesin', 1991, Proc. Natl. Acad. Sci. USA 88: 10535-10539.
Ausubel et al., 'Short Protocols in Molecular Biology', (eds.), Current Protocols in Molecular Biology, John Wiley & Sons, NY (1995).
Baldwin et al. (eds.), "Analysis, Results, and Future Prospective of the Therapeutic Use of Radiolabeled Antibody in Cancer Therapy", in Monoclonal Antibodies for Cancer Detection and Therapy, pp. 303-316 (Academic Press 1985).
Bao, J., 'Capillary electrophoretic immunoassays', Chromatogr. B. Biomed. Sci. 699:463-80 (1997).
Baum, 'Solid-phase synthesis of benzodiazepines', C&EN, benzodiazepines, Jan. 18, 1993, p. 33.
Bebbington et al., The use of vectors based on gene amplification for the expression of cloned genes in mammalian cells in DNA cloning, vol. 3. (Academic Press, New York, 1987.
Bertino et al, 'Matinib mesylate enhances therapeutic effects of gemcitabine in human malignant mesothelioma xenografts', Clin Cancer Res. 2008;14(2):541-548.
Better et al., 'Escherichia coli Secretion of an Active Chimeric Antibody Fragment', Science 240:1041-1043 (1988).
Bianchi, 'DAMPs, PAMPs and alarmins: all we need to know about danger', ME (2007), J Leukoc Biol 81: 1-5; 13-15.
Bitter et al., 'Vectors for Expression of Cloned Genes', Methods in Enzymol. 153:51-544 (1987).
BLAST and Gapped BLAST programs, the default parameters of the respective programs (e.g., BLASTN). See http://www.ncbi.nlm.nih.gov, as available on Apr. 10, 2002.
Bocchetta M, et al., "Human mesothelial cells are unusually susceptible to simian virus 40-mediated transformation and asbestos cocarcinogenicity," Proc Natl Acad Sci USA. 2000; 97:10214-10219.

Campbell et al., 'Phosphonate Ester Synthesis Using a Modified Mitsunobu Condensation', 1994, J. Org. Chem., 59:658.
Carbone M. et al., (2006) 'The pathogenesis of mesothelioma', (Translated from eng) Semin Diagn Pathol 23(1):56-60 (in eng).
Carrell et al., 'New promise in combinatorial chemistry: synthesis, characterization, and screening of small-molecule libraries in solution', Chem Biol. 2:171-183, 1995.
Chen et al., '"Analogous" Organic Synthesis of Small-Compound Libraries: Validation of Combinatorial Chemistry in Small-Molecule Synthesis', 1994, J. Amer. Chem. Soc., 116:2661.
Chien et al., 'The two-hybrid system: A method to identify and clone genes for proteins that interact with a protein of interest', Proc. Natl. Acad. Sci. USA 88:9578-9582 (1991).
Cho, et al., 'An Unnatural Biopolymer', 1993 Science 261:1303-1305.
Choe N, et al., 'Pleural Macrophage Recruitment and Activation in Asbestos in Asbestos-induced Pleural Injury', (1997) Pleural macrophage recruitment and activation in asbestos-induced pleural injury. (Translated from eng) Environ Health Perspect 105 Suppl 5:1257-1260 (in eng).
Clackson et al., 'Making antibody fragments using phage display libraries', Nature 352: 624-628, 1991.
Cockett et al., 'High Level Expression of Tissue Inhibitor of Metalloproteinases in Chinese Hamster Ovary Cells Using Glutamine Synthetase Gene Amplification', Bio/Technology 8:2 (1990).
Colbere-Garapin et al., 'A New Dominant Hybrid Selective Marker for Higher Eukaryotic Cells', J. Mol. Biol. 150:1 (1981).
Crouse et al., 'Expression and amplification of engineered mouse dihydrofolate reductase minigenes', Mol. Cell. Biol. 3:257 (1983).
Denardo et al., 'Comparison of 1,4,7,10-tetraazacylododecane-N, N', NΔ,N'Δ-tetraacetic acid (DOTA)-peptide-ChL6, a novel immunoconjugate with catabolizable linker, to 2-iminothiolane-2-[p-(bromoacetannido)benzyl]-DOTA-ChL6 in breast cancer xenografts', 1998, Clin Cancer Res 4:2483.
Dracopoli et al., 'Vectors for Gene Therapy', (eds), Current Protocols in Human Genetics, John Wiley & Sons, NY (1994), Chapter 12.
Dracopoli et al., 'Delivery Systems for Gene Therapy', (eds), Current Protocols in Human Genetics, John Wiley & Sons, NY (1994), Chapter 13.
Duncan et al, 'Localization of the binding site for the human high-affinity Fc receptor on IgG', 1988, Nature 332:563-564.
Erickson et al., 'Design, Activity, and 2.8 Å Crystal Structure of a C2 Symmetric Inhibitor Complexed to HIV-1 Protease', Science 249:527-533 (1990).
Fell et al., 'Genetic construction and characterization of a fusion protein consisting of a chimeric F(ab') with specificity for carcinomas and human IL-2', 1991, J. Immunol. 146:2446-2452.
Fetrow et al., 'Method for Prediction of Protein Function from Sequence using the Sequence-to-Structure-to-Function Paradigm with Application to Glutaredoxins/Thioredoxins and T1 Ribonucleases', J. Mol. Biol. 281: 949-968 (1998).
Fetrow et al., 'Functional Analysis of the Escherichia coli Genome Using the Sequence-to-Structureto-Function Paradigm: Identification of Proteins Exhibiting the Glutaredoxin/Thioredoxin in Disulfide Oxidoreductase Activity', J. Mol. Biol. 282:703-711 (1998).
Field et al., 'A novel genetic system to detect protein-protein interactions', Nature 340:245-246 (1989).
Fink MP, 'Ethyl Pyruvate: A Novel Treatment for Sepsis', Curr Drug Targets. 2007;8(4):515-8.
Foecking et al., 'Powerful and versatile enhancer-promoter unit for mammalian expression vectors', Gene 45:101 (1986).
Furka, 'General method for rapid synthesis of multicomponent peptide mixtures', 1991, Int. J. Pept. Prot. Res., 37:487-493.
Garnett, 'Targeted drug conjugates: principles and progress,' 2002, Adv Drug Deliv Rev 53:171.
Gentz et al., 'Bioassay for trans-activation using purified human immunodeficiency virus tat-encoded protein: Trans-activation requires mRNA synthesis', Proc. Natl. Acad. Sci. USA 86:821-824 (1989).
Ghetie et al., 'Increasing the serum persistence of an IgG fragment by random mutagenesis', 1997, Nat. Biotech. 15:637-40.

(56) References Cited

OTHER PUBLICATIONS

Gillies et al., 'High-level expression of chimeric antibodies using adapted cDNA variable region cassettes', (1989) *J. Immunol. Methods* 125:191-202.
Gillies et al., 'Antibody-targeted interleukin 2 stimulates T-cell killing of autologous tumor cells', 1992, PNAS 89:1428-1432.
Greenspan et al., 'Idiotypes: structure and immunogenicity', *FASEB J.* 7(5):437-444; (1989).
Hagihara et al., 'Vinylogous Polypeptides: An Alternative Peptide Backbone', 1992, J. Amer. Chem. Soc., 114:6568.
Hammerling, et al., 'Monoclonal Antibodies and T-Cell Hybridomas', 563-681 (Elsevier, N.Y., 1981).
Hansson, et al., 'Evolution of Differential Substrate Specificities in Mu Class Glutathione Transferases Probed by DNA Shuffling', 1999, J. Mol. Biol. 287:265-76.
Harayama, 'Artifical evolution by DNA shuffling', 1998, Trends Biotechnol. 16(2): 76-82.
Harlow et al., 'Antibodies: A Laboratory Manual', (Cold Spring Harbor Laboratory Press, 2nd ed. 1988).
Haugland, 'Handbook of Fluorescent Probes and Research Chemicals', (1996).
Hellstrom et al., 'Antibodies for Drug Delivery', in Controlled Drug Delivery (2nd Ed.), Robinson et al. (eds.), pp. 623-53 (Marcel Dekker, Inc. 1987).
Hirschmann et al., 'Nonpeptidal Peptidomimetics with a β-D-Glucose Scaffolding. A Partial Somatostatin Agonist Bearing a Close Structural Relationship to a Potent, Selective Substance P Antagonist', 1992, J. Amer. Chem. Soc., 114:9217-9218.
HMGB1 Elisa Kit Instructions, IBL International, in 9 pages, dated Jan. 7, 2011.
Hobbs et al., '"Diversomers": An approach to nonpeptide, nonoligomeric checmical diversity', 1993, Proc. Natl. Acad. Sci. USA, 90:6909-6913.
Hodgson, 'Data-Directed Drug Design', *Bio. Technology* 9:19-21 (1991).
Houghton et al., 'Generation and use of synthetic peptide combinatorial libraries for basic research and drug discovery', 1991, Nature, 354:84-88.
Hruby, et al., 'Emerging approaches in the molecular design of receptor-selective peptide ligands: conformational, topographical and dynamic considerations', 1990 *Biochem J* 268(2):249-262.
Huston et al., 'Protein Engineering of Single-Chain Fv Analogs and Fusion Proteins', Methods in Enzymology 203:46-88 (1991).
Hutchins et al., 'Improved biodistribution, tumor targeting, and rediced immunogenicity in mice with a y4 variant of Campath-1H', 1995, Proc Natl. Acad Sci USA 92:11980-11984.
Idusogie et al, 'Mapping of the C1q Binding Site on Rituxan, a Chimeric Antibody with a human IgG1 Fc', 2000, J Immunol 164:4178-4184.
Idusogie et al, 'Engineered Antibodies with Increased Activity to Recruit Complement', 2001, J Immunol 166:2571-2575.
Inouye & Inouye, 'Up-promoter mutations in the *Ipp* gene of *Escherichia coil*', Nucleic Acids Res. 13:3101-3109 (1985).
International Search Report and Written Opinion dated Jan. 29, 2013 in Application No. PCT/US2012/041428.
International Search Report and Written Opinion dated Feb. 1, 2013 in Application No. PCT/US2012/041430.
Jefferis et al, 'Recognition sites on human IgG for Fcy receptors : the role of glycosylation', 1995, Immunol Lett. 44:111-117.
Jefferis et al, 'Modulation of FcyR and human complement actication by IgG3-core oligosaccharide interactions', 1996, Immunol Lett 54:101-104.
Jefferis et al, 'Interaction sites on human IgG-Fc for FcyR : current models', 2002, Immunol Lett 82:57-65.
Jespers et al., 'Guiding the Selection of Human Antibodies from Phage Display Repertoires to a Single Epitope of an Antigen', *Bio/technology* 12:899-903 (1988).
Jones et al., 'Replacing the complementarity-determining regions in a human antibody with those from a mouse', *Nature* 321:522-525, 1986.

Karlin et al., 'Applications and statistics for multiple high-scoring segments in molecular sequences', Proc. Natl. Acad. Sci. USA, 90:5873-5877 (1993).
Kohler, 'Immunoglobulin chain loss in hybridoma lines', *Proc. Natl. Acad. Sci. USA* 77:2197 (1980).
Kostelny et al., 'Formation of a Bispecific Antibody by the Use of Leucine Zippers', J. Immunol. 148:1547-1553 (1992).
Lam K.S., 'Application of combinatorial library methods in cancer research and drug discvoery', *Anticancer Drug Res.*, 12:145-167 (1997).
Leanna et al., 'The reverse two-hybrid system: a genetic scheme for selection against specific protein/protein ineractions', *Nucl. Acid Res.* 24:3341-3347 (1996).
Liang et al., 'Parallel Synthesis and Screening of a sSolid Phase Carbohydrate Library', 1996, Science, 274-1520-1522.
Liu et al., 'High-Mobility Group Box 1-Mediated Matrix Metalloproteinase-9 Expression in Non-Small Cell Lung Cancer Contributes to Tumor Cell Invasiveness', (Am. J. Respir Cell Mol. Biol. 2010 vol. 43, p. 530-538).
Lipinski et al., 'Experimental and computational approaches to estimate solubility and permeability in drug discovery and development settings', Adv. Drug Delivery Rev. 23:3-25, 1997.
Logan et al., 'Adenovirus tripartite leader sequence enhances translation of mRNAs late after infection', *Proc. Natl. Acad. Sci. USA* 81:355-359 (1984).
Lonberg et al., 'Human Antibodies from Transgenic Mice', *Int. Rev. Immunol.* 13:65-93 (1995).
Lorenzo et al., 'PCR-Based Method for the Introduction of Mutations in Genes Cloned and Expressed in Vaccinia Virus', 1998, Biotechniques 24(2): 308-313.
Lowman HB, 'Bacteriophage Display and Discovery of Peptide Leads for Drug Development', *Annu. Rev. Biophys. Biomol. Struct.* 26:401-424 (1997).
Lowy et al., 'Isolation of Transforming DNA: Cloning the Hamster aprt Gene', *Cell* 22:817 (1980).
Lund et al., 'Human FcyRI and FcyRII Interact with Distinct but Overlapping Sites on Human IfG1', 1991, J. Immunol. 147:2657-2662.
Lund et al, 'Multiple Binding Sites on the CH2 Domain of IgG for Mouse FcyR11', 1992, Mol Immunol 29:53-59.
Lund et al., 'Oligosaccharide-protein interactions in IgG can modulate recognition by Fcy receptors' 1995, Faseb J 9:115-119.
Lund et al, 1996, 'Multiple Interactions of IgG with Its Core Oligosaccharide Can Modulate Recognition by Complement and Human Fcy Receptor I and Influence the SYnthesis of Its Oligosaccharide Chains1', J Immunol 157:4963-4969.
Marks et al., 'By-Passing Immunization: Building High Affinity Human Antibodies by Chain Shuffling', *Biotechnology* 10:779-783, 1992.
Mathis G., 'Probing Molecular Interactions with Homogeneous Techniques Based on Rare Earth Cryptates and Fluorescence Energy Transfer', *Clin. Chem.* 41:139-147 (1995).
McCafferty et al., 'Phage antiboides: filamentous phage displaying antibody variable domains', *Nature* 348:552-554, 1990.
Moore, W.J., Physical Chemistry, 4th Edition, Prentice-Hall, N.J. (1972).
Morgan et al., 'Human Gene Therapy', *Ann. Rev. Biochem.* 62:191-217 (1993).
Morgan, et al. 'Chapter 26. Approaches to the Discovery of Non-Peptide Ligands for Peptide Receptors and Peptidases', 1989 *Ann Rep Med Chem* 24:243-252.
Morrison, 'Transfectomas Provide Novel Chimeric Antibodies', *Science* 229:1202 (1985).
Mulligan, 'Selection for animal cells that express the *Escherichia coli* gene coding for xanthine-guanine phosphoribosyltransferase', *Science* 260:926-932 (1993).
Mulligan et al., 'The Basic Science of Gene Therapy', *Proc. Natl. Acad. Sci. USA* 78:2072 (1981).
Mullinax et al., 'Expression of a Heterodimeric Fab Antibody Protein in One Cloning Step', *BioTechniques* 12(6):864-869 (1992).
Naramura et al., 'Mechanisms of cellular cytotoxicity mediated by a recombinant antibody-IL2 fusion protein against human melanoma cells', 1994, Immunol. Lett. 39:91-99.

(56) References Cited

OTHER PUBLICATIONS

Nissinoff, J., 'Idiotypes: Concepts and Applications', Immunol. 147(8):2429-2438 (1991).
O'Hare et al., 'Transformation of mouse fibroblasts to methotrexate resistance by a recombinant plasmid expressing a prokaryotic dihydrofolate reductase', Proc. Natl. Acad. Sci. USA 78:1527 (1981).
Ol et al., 'Chimeric Antibodies', BioTechniques 4:214 (1986).
Office Action dated May 13, 2014 in U.S. Appl. No. 14/123,722.
Office Action dated Nov. 24, 2014 in U.S. Appl. No. 14/123,722.
Padlan, 'A Possible Procedure for Reducing the Immunogenicity of Antibody Variable Domains While Preserving Their Ligand-Binding Properties', Molecular Immunology 28(4/5):489-498 (1991).
Parra et al., 'Tissue inhibitor of metalloproteinase-1 is increased in the saphenofemoral junction of patients with varices in the leg', J. Vasc. Surg. 28:669-675 (1998).
Patten et al., 'Applications of DNA shuffling to pharmaceuticals and vaccines', 1997, Curr. Opinion Biotechnol. 8:724-33.
Peterson et al., 'Enzymatic Cleavage of Peptide-Linked Radiolabels from Immunoconjugates', 1999, Bioconjug Chem 10:553.
Phizicky et al., 'Protein-protein interactions: methods for detection and anlysis', Microbiol. Rev. 59:94-123 (1995).
Presta et al., 'Engineering therapeutic antibodies for improved function', 2002, Biochem Soc Trans 30:487-490.
Proudfoot, 'Transcriptional interference and termination between duplicated α-globin gene constructs suggests a novel mechanism for gene regualtion', Nature 322:562 (1986).
Quinlan TR et al., (1994) Oxygen radicals and asbestos-mediated disease. (Translated from eng) Environ Health Perspect 102 Suppl 10:107-110 (in eng).
Reddy et al, 'Elimination of Fc Receptor-Dependent Effector Functions of a Modified IgG4 Monoclonal Antibody to Human CD4', 2000, J Immunol 164:1925-1933.
Pennington, 'Solid-Phase Synthesis of Peptides Containing the CH2NH Reduced Bond Surrogate', 1994 Meth Mol Bio 35:241-247.
Riechmann et al., 'Reshaping human antibodies for therapy', Nature 332:323 (1988).
Roguska. et al., 'Humanization of murine monoclonal antibodies through variable domain resurfacing', PNAS 91:969-973 (1994).
Rongen et al., 'Liposomes and immunoassays', J. Immunol. Methods 204:105-133 (1997).
Ruther et al., 'Easy identification of cDNA clones', EMBO J. 2:1791 (1983).
Santerre et al., 'Expression of prokaryotic genes for hygromycin B and G418 resistance as dominant-selection markers in mouse L cells', Gene 30:147 (1984).
Sawai et al., 'Direct Production of the Fab Fragment Derived From the Sperm Immobilizing Antibody Using Polymerase Chain Reaction and cDNA Expression Vectors', AJRI 34:26-34 (1995).
Schaffer et al., 'Improving the accuracy of PSI-BLAST protein database searches with composition-based statistics and other refinements', Nucleic Acids Res., 29:2994-3005 (2001).
Schmalzing et al., 'Capillary electrophoresis based immunoassays: A critical review', Electrophoresis 18:2184-93 (1997).
Schneider, 'MSI Offers Drug Discovery Software', Genetic Engineering News December: p. 20 (1998).
Self et al., 'Advances in immunoassay technology', Curr. Opin. Biotechnol. 7:60-65 (1996).
Shields et al., 'High Resolution Mapping of the Binding Site on Human IgG1 for FcgRI, FcgRII, FcgRIII, and FcRn and Design of IgG1 Variants with Improved Binding to the FcgR', 2001, J Biol Chem 276:6591-6604.
Shields, R. L. et al., 'Lack of Fucose on Human IgG1 N-Linked Oligosaccharide Improves Binding to Human Fc RIII and Antibody-dependent Cellular Toxicity', (2002) J. Biol. Chem. 277:26733-26740.
Shu et al., 'Secretion of a single-gene-encdoed immunoglobulin from myeloma cells', PNAS 90:7995-7999 (1993).
Sitia G et al., (2007), "Treatment with HMGB1 inhibitors diminishes CTL-induced liver disease in HBV transgenic mice," J Leukoc Biol 81: 100-7.
Skerra et al., 'Assembly of a Functional Immunoglobllllin Fv Fragment in Escherichia coli', Science 240:1038-1040 (1988).
Sowdhamini et al., 'Structural and functional analogy between pneumolysin and proaerolysin', Protein Engineering 10:207, 215 (1997).
Studnicka et al., 'Human-engineered monoclonal antibodies retain full specific binding activity by preserving non-CDR complementaritu-modulation residues', Protein Engineering 7(6):805-814 (1994).
Szybalska & Szybalski, 'Genetics of Human Cell Lines, IV. DNA-Mediated Heritable Transformation of a Biochemical Trait', Proc. Natl. Acad. Sci. USA 48:202 (1992).
Takahashi et al., 'Human Fas ligand: gene structure, chromosomal location and species specificity', Int. Immunol., 6:1567-1574 (1994).
Tempest et al., 'Reshaping A Human Monoclonal Antibody to Inhibit Human Respiratory Syncytial Virus Infection In Vivo', Biotechnology 9:266-273, 1991.
Thorpe et al., "The Preparation and Cytotoxic Properties of Antibody-Toxin Conjugates", Immunol. Rev. 62:119-58 (1982).
Tietze et al., 'Domino reactions for library synthesis of small molecules in combinatorial chemistry', Curr. Opin. Chem. Biol. 2:363-371, 1998.
Tolstoshev, 'Gene Therapy, concepts, Current Trials and Future Directions', Ann. Rev. Pharmacol. Toxicol. 32:573-596 (1993).
Tutt, et al., 'Trispecific F(ab')3 Derivatives That Use Cooperative Signaling Via the TCR/CD3 Complex and CD2 to Activate and Reidirect Resting Cytotoxic T Cells', J. Immunol. 147:60-69 (1991).
Ulloa L, et al., High-mobility group box 1 (HMGB1) protein: friend and foe. Cytokine Growth Factor Rev. 2006;17:189-201.
Umana et al. 'Engineered glycoforms of an antineuro-blastoma IgG1 with optimized antibody-dependent cellular cytotoxic activity', (1999) Nat. Biotech. 17:176-1.
Van Heeke et al., 'Expression of Human Asparagine Synthetase in Escherichia coli', J. Biol. Chem. 24:5503-5509 (1989).
Van Holde, K.E., 'X-Ray Diffraction', Physical Biochemistry, Prentice-Hall, N.J. pp. 221-239 (1971).
Vaughn et al., 'Human Antibodies with Sub-nanomolar Affinities Isolated from a Large Non-immunized Phage Display Library', 1996, Nature Biotechnology, 14(3):309-314.
Vie et al., 'Human fusion proteins between interleukin 2 and IgM heavy chain are cytotoxic for cells expressing the interleukin 2 receptor', 1992, Proc. Natl. Acad. Sci. USA 89:11337-11341.
Weinstein, B., 'Peptide Backcone Modifications: A Structure-Activity Analysis of Peptides Containing Amide Bond Surrogates, Conformational Constraints, and Rela', 1983 Chemistry & Biochemistry of Amino Acids, Peptides and Proteins vol. 7, pp. 267-357, Marcel Dekker, Inc., New York.
Wells, 'Systematic Mutational Analyses of Protein-Protein Interfaces', Methods in Enzymol. 202:390-411 (1991).
Wendling, P., "Erionite Deposits in Western U.S. Raise Concern", Rheumatology News, Feb. 2011.
Wigler et al., 'Transfer of Purified Herpes Vuris Thymidine Kinase Gene to Cultured Mouse Cells', Cell 11:223 (1977).
Wigler et al., 'Transformation of mammalian cells with an amplifiable dominant-acting gene', Proc Natl. Acad. Sci. USA 77:357 (1980).
Wilson et al., 'The Structure of an Antigenic Determinant in a Protein', Cell 37:767 (1984).
Wu and Wu, 'Delivery systems for gene therapy', Biotherapy 3:87-95 (1991).
Xu et al., 'In Vitro Characterization of Five Humanized OKT3 Effector Function Variant Antibodies', 2000, Cell Immunol 200:16-26.
Yang H, et al., 'Programmed necrosis induced by asbestos in human mesothelial cells causes high-mobility group box 1 protein release and resultant inflammation', Proc Natl Acad Sci USA. 2010;107(28)12611-12616.

(56) References Cited

OTHER PUBLICATIONS

Yang H, et al., 'TNF-α inhibits asbestos-induced cytotoxicity via a NF-κB-dependent pathway, a possible mechanism for asbestos-induced oncogenesis.', *Proc Natl Aced Sci USA.* 2006; 103(27):10397-10402.

Young KH, 'Yeast Two-Hybrid: So Many Interactions, (in) So Little Time . . . ', *Biol. Reprod.* 58:302-311 (1998).

Zheng et al., 'Administration of Noncytolytic IL-10/Fc in Murine Models of Lipopolysaccharide-Induced Septic Shock and Allogeneic Islet Transplantation', 1995, J. Immunol. 154:5590-5600.

Zimmerman et al., 'A Triglyceride Linker Improves Tumor Uptake and Biodistributions of 67-Cu-Labeled Anti-Neuroblastoma Mab chCE7 F9ab')2 Fragments', 1999, Nucl Med Biol 26:943.

Notice of Allowance dated Sep. 17, 2015 in U.S. Appl. No. 14/123,722.

Abraham, D.J., "Burger's Medicinal & Chemistry Drug Discovery, Sixth Edition", Wiley-Interscience, 946 pages, Jun. 14, 1998.

Huttunen et al., "Amphoterin as an extracellular regulator of cell motility: from discovery to disease", Journal of Internal Medicine, vol. 255, pp. 351-366, 2004.

Kriegler, M., "Gene Transfer and Expression—A Laboratory Manual", M Stockton Press, 248 pages, 1990.

Polak, J.M., "Introduction to Immunocytochemistry, Second Edition", BIOS Scientific Publishers, Springer, 77, pages, 1997.

Tibech, Trends in Biotech, Elsevier Science Publishers Ltd. (UK), vol. 11, pp. 156-215, May 1993.

Thorpe, P.E., "Antibody Carriers of Cytotoxic Agents in Cancer Therapy: A Review", Drug Targeting Laboratory, Imperial Cancer Research Fund, pp. 475-506, 1985.

* cited by examiner

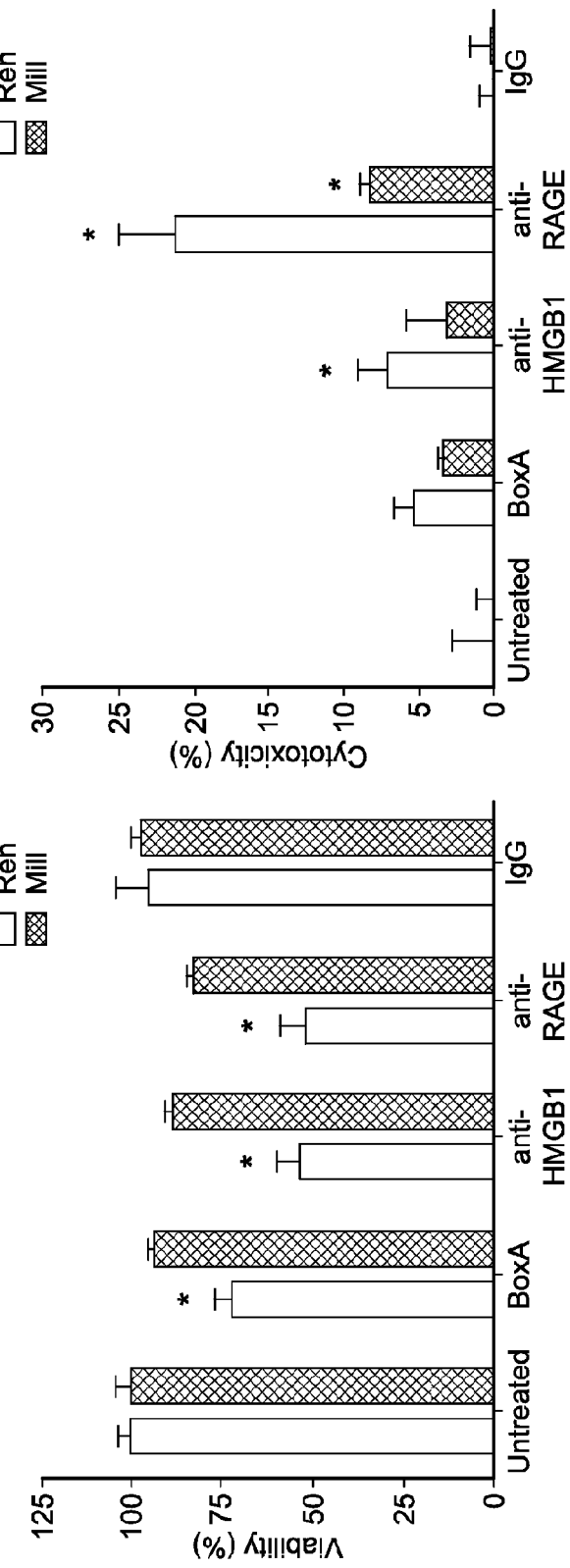
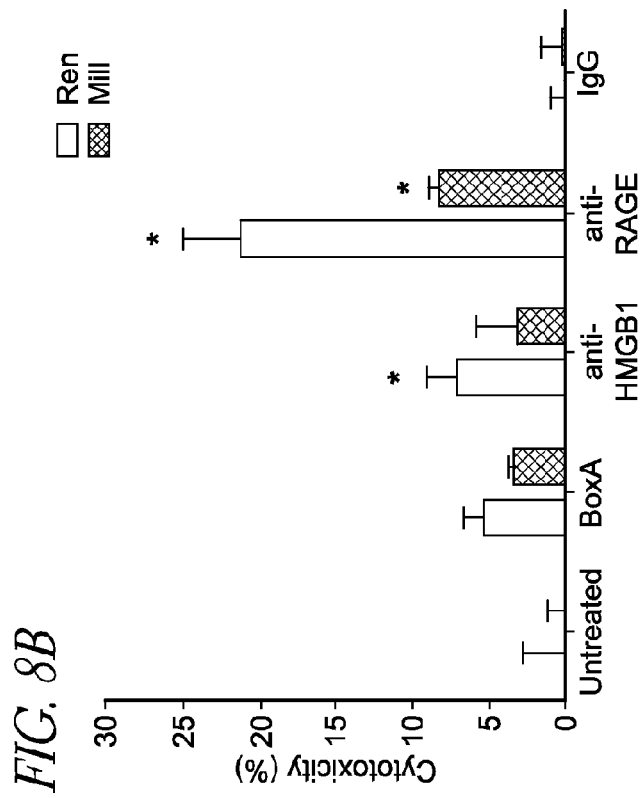
FIG. 8B
FIG. 8A

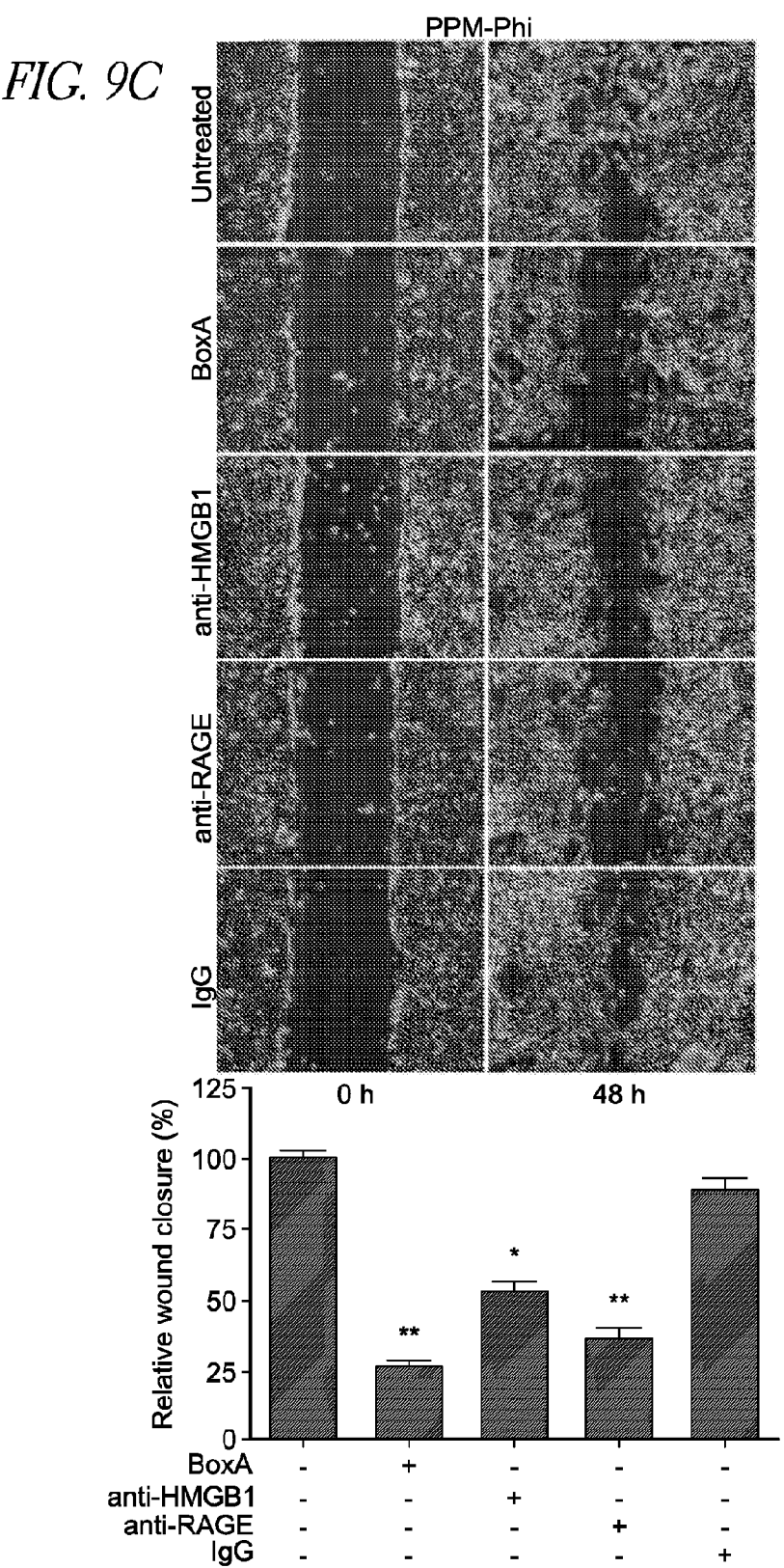

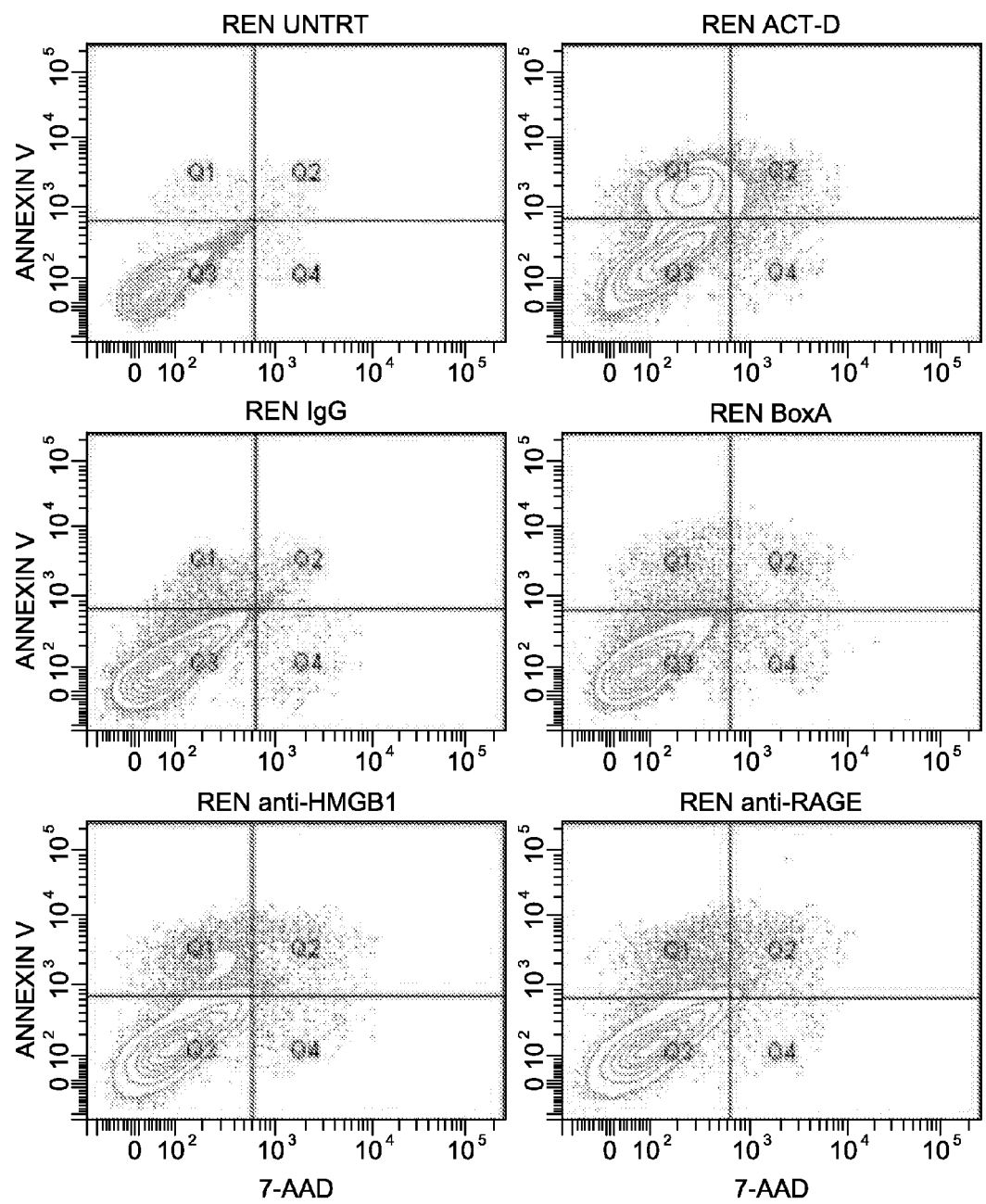

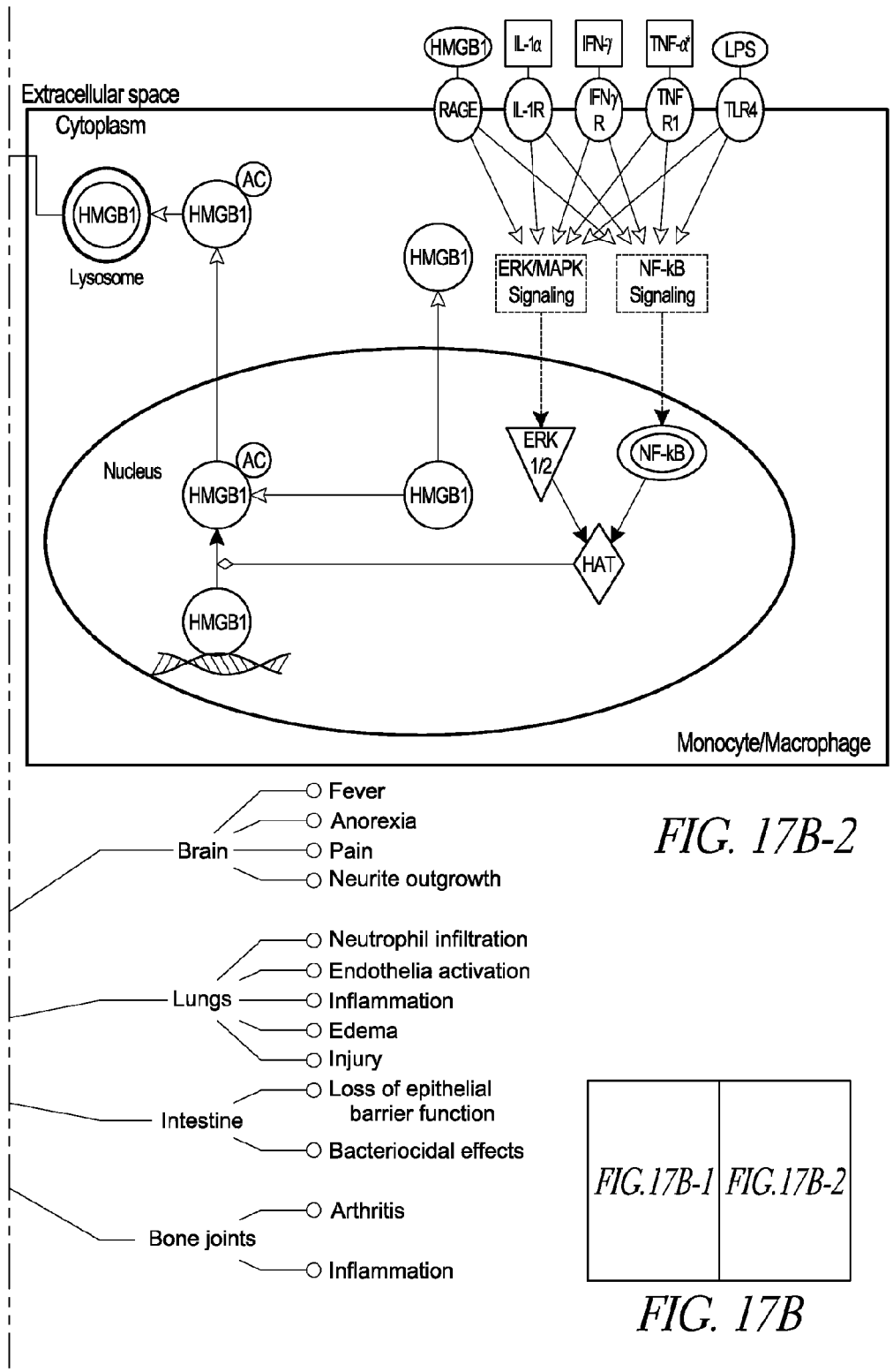

TREATMENT AND PREVENTION OF CANCER WITH HMGB1 ANTAGONISTS

REFERENCE TO RELATED APPLICATIONS

This application is the U.S. National Phase of International Application PCT/US2012/041430, filed Jun. 7, 2012, and claims priority to U.S. Provisional Application No. 61/494,340, filed Jun. 7, 2011 and 61/502,275, filed Jun. 28, 2011. Each of the priority applications is hereby incorporated by reference in its entirety.

The present application is being filed along with a Sequence Listing in electronic format. The Sequence Listing is provided as a file Sequence_Listing-UOH_045NP.TXT, created and last modified on Jan. 10, 2014, which is 4,742 bytes in size. The information in the electronic format of the Sequence Listing is incorporated herein by reference in its entirety.

STATEMENT REGARDING FEDERALLY SPONSORED R&D

This invention was made with Government support under Grant No. R01 CA160715 awarded by the National Institutes of Health. The Government has certain rights in this invention.

FIELD

This application relates generally to the field of cancer biology, prevention, and treatment. Embodiments provided herein relate to methods and compositions for treating or preventing cancer. More particularly, several embodiments are drawn to treating or preventing malignant mesothelioma with antagonists of HMGB1.

BACKGROUND

In the US, asbestos causes ~2-3,000 malignant mesothelioma (MM) deaths/year, and contributes to an even larger number of lung carcinomas because asbestos has a synergistic carcinogenic effect with cigarette smoke. The latency of 30-50 years from the time of exposure to tumor development could potentially allow time for intervention to block the presently unclear mechanism(s) that trigger asbestos-induced carcinogenesis (Carbone M & Bedrossian C W (2006) The pathogenesis of mesothelioma. (Translated from eng) Semin Diagn Pathol 23(1):56-60 (in eng)).

Asbestos refers to a family of mineral fibers that includes crocidolite, often considered the most oncogenic type. Since asbestos does not induce malignant transformation of primary human mesothelial cells (HM) directly, indirect mechanisms of carcinogenesis have been investigated. Inhaled asbestos fibers become entrapped in the lung and some migrate through the lymphatics to the pleura.

Indeed, cancer often arises in the setting of chronic inflammation and it has been suggested that asbestos-induced inflammation might be somehow linked to asbestos carcinogenesis (Quinlan T R, Marsh J P, Janssen Y M, Borm P A, & Mossman B T (1994) Oxygen radicals and asbestos-mediated disease. (Translated from eng) Environ Health Perspect 102 Suppl 10:107-110 (in eng); Choe N, et al. (1997) Pleural macrophage recruitment and activation in asbestos-induced pleural injury. (Translated from eng) Environ Health Perspect 105 Suppl 5:1257-1260 (in eng)).

The mechanisms that trigger the chronic inflammatory response seen in the lungs of asbestos-exposed individuals and in many MM patients are unknown. Macrophages play an important role in this process by releasing mutagenic reactive oxygen species (ROS) and cytokines that support inflammation. Among these cytokines, TNF-α has been identified as a critical mediator of the pathogenesis of asbestos-related disease. TNF-α has been linked to tumor promotion, to fibrosis and asbestosis, to asbestos carcinogenesis and to MM.

Asbestos is cytotoxic. Most HM exposed to asbestos die within 24-48 hrs. The mechanisms of asbestos-induced HM cell death and the possible link between cytotoxicity and carcinogenesis is unclear.

SUMMARY

In one embodiment, a method of treating cancer in a subject includes administering to a subject having cancer an effective amount of an antibody, preferably a monoclonal antibody specific for HMGB1 or the receptor for advanced glycation end products (RAGE) sufficient to treat the cancer in the subject. In one aspect, the effective amount of the monoclonal antibody is sufficient to reduce growth of the cancer. In another aspect, the effective amount of the monoclonal antibody is sufficient to enhance survival of the subject. In a further aspect, the monoclonal antibody is capable of reducing or inhibiting asbestos-induced transformation of a mesothelial cell. In an additional aspect, the monoclonal antibody is capable of reducing or inhibiting motility of a malignant mesothelioma cell assayed by wound healing. Yet in another aspect, the monoclonal antibody is capable of reducing or inhibiting anchorage independent growth of a malignant mesothelioma cell. In a further aspect, the monoclonal antibody is capable of inducing cytotoxicity of a malignant mesothelioma cell. In an additional aspect, the monoclonal antibody comprises a human constant region. Still in an additional aspect, the monoclonal antibody comprises a human variable region. In a further aspect, the monoclonal antibody is chimeric and comprises a human constant region and a mouse variable region. In another aspect, the monoclonal antibody has neutralizing activity against HMGB1 or RAGE. In an additional aspect, the cancer comprises a solid tumor. In the same aspect, the cancer is malignant mesothelioma. In a further aspect, the subject is human.

Another embodiment relates to a method of treating cancer in a subject including administering to a subject having cancer an effective amount of a BoxA polypeptide comprising the amino acid sequence of SEQ ID NO:3 or a variant thereof having at least 85% identity, wherein the effective amount of the BoxA polypeptide or variant thereof is sufficient to treat the cancer in the subject. In one aspect, the effective amount of the polypeptide is sufficient to reduce growth of the cancer. In another aspect, the effective amount of the polypeptide is sufficient to enhance survival of the subject. In a further aspect, the polypeptide is capable of reducing or inhibiting asbestos-induced transformation of a mesothelial cell. In an additional aspect, the polypeptide is capable of reducing or inhibiting motility of a malignant mesothelioma cell assayed by wound healing. Further in another aspect, the polypeptide is capable of reducing or inhibiting anchorage independent growth of a malignant mesothelioma cell. In an additional aspect, the polypeptide is capable of reducing or inducing cytotoxicity of a malignant mesothelioma cell. In yet another aspect, the cancer comprises a solid tumor. In the same aspect, the cancer can be, for example, malignant mesothelioma. In a further aspect, the subject is human.

A further embodiment is drawn to a method of treating cancer in a subject, which method, for example, can include providing or administering to a subject having cancer an effective amount of at least one anti-inflammatory compound sufficient to treat the cancer in the subject. In one aspect, the effective amount of the compound is sufficient to reduce growth of the cancer. In another aspect, the effective amount of the compound is sufficient to enhance survival of the subject. In an additional aspect, the cancer may be or may include, a solid tumor. In a further aspect, the cancer can be or include a malignant mesothelioma. In an additional aspect, the subject can be a human. In some aspects the subject can be a non-human mammal, for example, a rodent such as a mouse, a rat, a Guinea Pig and the like. In some other aspects the non-human mammal can be a rabbit or a dog, for example. In an another aspect, the anti-inflammatory drug can be, for example, aspirin. In yet a further aspect, the anti-inflammatory drug can be, for example, ethyl pyruvate.

An additional embodiment relates to a method of preventing or reducing the incidence of cancer in a subject, the method can including for example, providing or administering to a subject suspected of being at risk for developing cancer an effective amount of an antibody, preferable a monoclonal antibody specific for HMGB1 or RAGE, where the amount is sufficient to prevent, reduce and/or delay in the subject the development of cancer. In one aspect, the subject can be suspected of being at risk for developing malignant mesothelioma and the effective amount of the monoclonal antibody can be, for example, sufficient to prevent the subject from developing malignant mesothelioma. In another aspect, the subject can be, for example, suspected of being at risk for developing malignant mesothelioma has been exposed to asbestos. In some aspects the subject can be suspected of being at risk due to having been exposed to asbestos. In a further aspect, the effective amount of the antibody is sufficient to delay the development of malignant mesothelioma in the subject. In yet a further aspect, the antibody can be capable of reducing or inhibiting asbestos-induced transformation of a mesothelial cell. In an additional aspect, the monoclonal antibody can be capable of reducing or inhibiting motility of a malignant mesothelioma cell assayed by wound healing. Yet in another aspect, the monoclonal antibody can be capable of reducing or inhibiting anchorage independent growth of a malignant mesothelioma cell. In a further aspect, the antibody can be capable of inducing cytotoxicity of a malignant mesothelioma cell. In an additional aspect, the antibody can include a human constant region. Still in an additional aspect, the antibody may include a human variable region. In a further aspect, the antibody may be chimeric and can include, for example, a human constant region and a mouse variable region. In another aspect, the monoclonal antibody can have neutralizing activity against HMGB1 or RAGE. In an additional aspect, the cancer may include a solid tumor. In the same aspect, the cancer can be, for example, a malignant mesothelioma. In a further aspect, the subject can be a human. In some aspects, the subject can be a non-human animal, for example a non-human mammal. The non-human mammal can be for example, a rodent, a primate, a canine, a lagomorph and the like. For example, the animal can be a rat, a mouse, a Guinea Pig, a rabbit, a dog, a chimpanzee and the like.

Another embodiment relates to a method of preventing cancer in a subject, the method including, for example, providing or administering to a subject suspected of being at risk for developing cancer an effective amount of a BoxA polypeptide comprising the amino acid sequence of SEQ ID NO:3 or a variant thereof having at least 85% identity, wherein the effective amount of the BoxA polypeptide or variant thereof is sufficient to prevent or reduce or delay the incidence of cancer in the subject. In one aspect, the subject can be, for example, suspected of being at risk for developing malignant mesothelioma and the effective amount of the polypeptide can be sufficient to prevent the subject from developing malignant mesothelioma. In another aspect, the subject suspected of being at risk for developing the cancer, for example, malignant mesothelioma, has been exposed to asbestos. In a further aspect, the effective amount of the polypeptide can be sufficient to delay the development of malignant mesothelioma in the subject. Yet in another aspect, the effective amount of the polypeptide can be capable of reducing or inhibiting asbestos-induced transformation of a mesothelial cell.

A further embodiment is drawn to a method of preventing cancer in a subject, the method including, for example, providing or administering to a subject suspected of being at risk for developing cancer an effective amount of at least anti-inflammatory drug sufficient to prevent the subject from developing cancer. In one aspect, the subject can be suspected of being at risk for developing malignant mesothelioma and the effective amount of the drug can be, for example, an amount sufficient to prevent the subject from developing malignant mesothelioma. In a further aspect, the subject suspected of being at risk for developing cancer, for example, malignant mesothelioma has been exposed to asbestos. Yet in an additional aspect, the cancer can include a solid tumor. Still in a further aspect, the cancer can be, for example, malignant mesothelioma. In another aspect, the subject can be human. In some aspects, the subject can be a non-human animal, for example a non-human mammal. The non-human mammal can be for example, a rodent, a primate, a canine, a lagomorph and the like. For example, the animal can be a rat, a mouse, a Guinea Pig, a rabbit, a dog, a chimpanzee and the like. In an additional aspect, the anti-inflammatory drug can be, for example, aspirin. In yet a further aspect, the anti-inflammatory drug can be, for example, ethyl pyruvate.

An additional embodiment relates to methods of screening for an HMGB1 antagonist capable of treating cancer including administering a candidate HMGB1 antagonist to an immunodeficient mouse having cancer and identifying the candidate antagonist as capable of treating cancer when the growth of the cancer is reduced or the survival of the mouse is extended compared to control. In one aspect, the candidate HMGB1 antagonist is antibody specific for HMGB1 or RAGE, a BoxA polypeptide comprising the amino acid sequence of SEQ ID NO:3 or a variant thereof having at least 85% identity, or an anti-inflammatory drug. In another aspect, the cancer is mesothelioma.

A further embodiment relates to a method of screening for an HMGB1 antagonist capable of preventing cancer including administering a candidate HMGB1 antagonist to an immunodeficient mouse, providing cancer cells to the mouse, and identifying the candidate HMGB1 antagonist as capable of preventing cancer when the onset of tumor formation is delayed or the growth of tumors is reduced compared to control. In one aspect, the candidate HMGB1 antagonist is antibody specific for HMGB1 or RAGE, a BoxA polypeptide comprising the amino acid sequence of SEQ ID NO:3 or a variant thereof having at least 85% identity, or an anti-inflammatory drug. In another aspect, the cancer is mesothelioma.

BRIEF DESCRIPTION OF THE DRAWINGS

FIG. 2 shows expression of the HMGB1 receptors TLR2 and TLR4 in MM cells.

FIG. 3 shows HMGB1 inhibitors hinder asbestos-induced HM transformation.

FIG. 5 shows HMGB1 is an autocrine mitogen and chemotactic agent in MM cells.

FIG. 6 shows HMGB1 is an autocrine mitogen and chemotactic agent in MM cells.

FIG. 7 shows HMGB1 is an autocrine mitogen and chemotactic agent in MM cells.

FIG. 8 shows MM cells require HMGB1 for survival and migration. FIG. 8A is a graph representing a viability assay showing that inhibition of HMGB1 by BoxA or anti-HMGB1 or anti-RAGE antibodies substantially decreased the viability of REN but had mild effects on PPM-Mill cells. FIG. 8B is a graph representing a cytotoxicity assay showing that anti-HMGB1 and anti-RAGE antibodies induced substantial cytotoxicity (P<0.05) in REN, but mild cytotoxicity in PPM-Mill cells compared with untreated controls.

FIG. 9 shows MM cells require HMGB1 for survival and migration. FIG. 9C shows that wound closure time of PPM-Phi cells was significantly increased by all HMGB1 antagonists.

FIG. 10 shows inhibition of HMGB1 disrupts MM cells anchorage-independent growth.

FIG. 11 shows anti-HMGB1 monoclonal antibody reduced tumor growth and enhanced survival in a mouse model of MM.

FIG. 13 shows aspirin inhibits outgrowth of REN human MM cells.

DETAILED DESCRIPTION

Figure 1A:
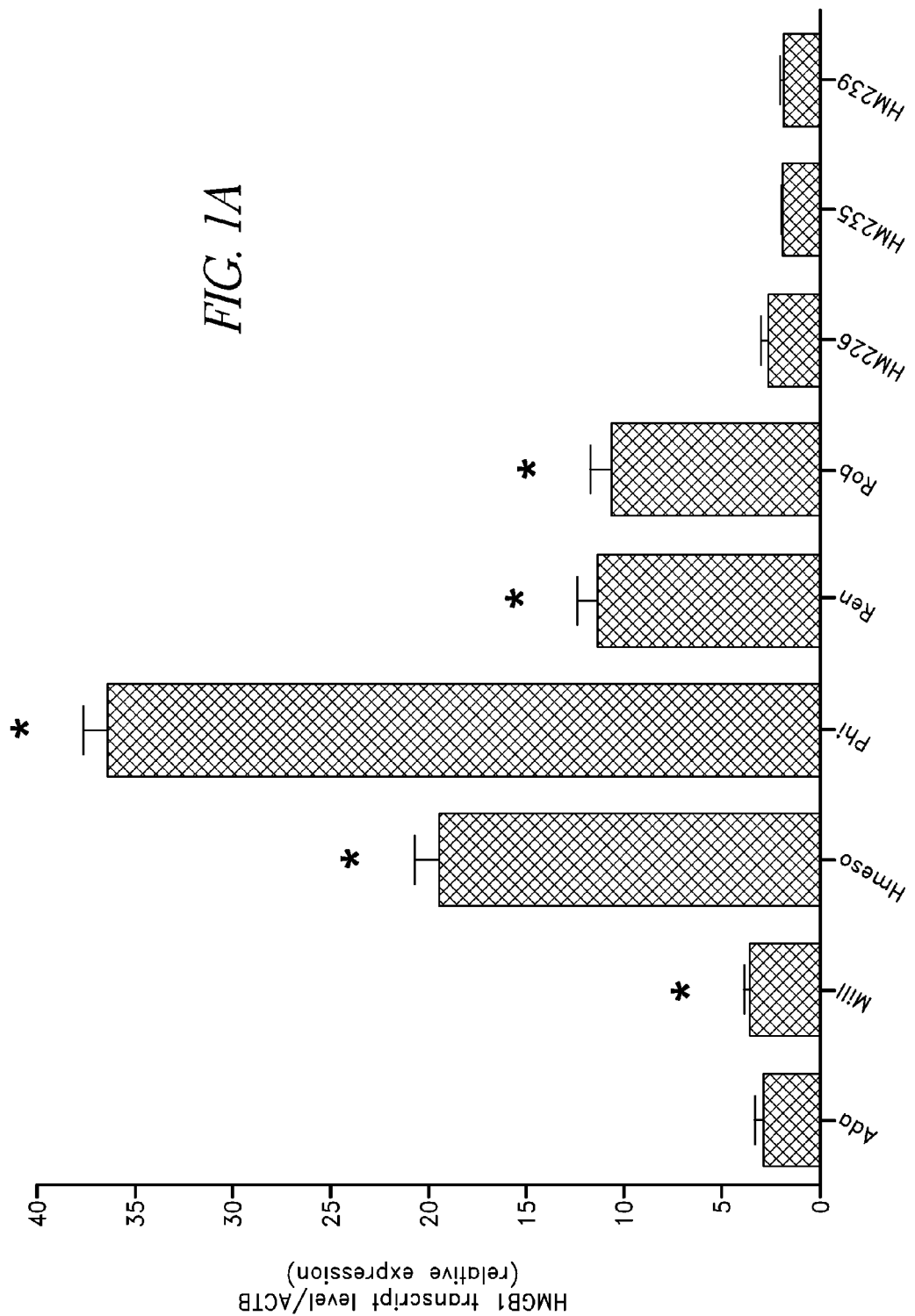
FIG. 1A is a graph showing qPCR measurements of HMGB1 mRNA transcript levels.

Embodiments provided herein generally are drawn to methods and compositions for treating, reducing or preventing cancer with antagonists of the High Mobility Group Box 1 (HMGB1) protein. Some embodiments relate to methods and compositions for treating cancer with certain anti-inflammatory agents. Also, some embodiments relate to the surprising and unexpected discovery that certain cancers of the lung, including for example, malignant mesothelioma can be treated or prevented with antagonists of the HMGB1 and with anti-inflammatory agents. Still further embodiments relate to methods of screening for or identifying such antagonists.

HMGB1 is a damage associate molecular pattern (DAMP) molecule and a mediator of chronic inflammation (Bianchi M E (2007) DAMPs, PAMPs and alarmins: all we need to know about danger. J Leukoc Biol 81: 1-5; 13-15; which is incorporated herein by reference in its entirety). HMGB1 is actively secreted by macrophages and dendritic cells (DCs) and passively released by cells undergoing necrosis. HMGB1 is a nuclear protein, but can be detected in the cytoplasm of cells undergoing necrosis and in cells that actively secrete HMGB1, such as macrophages. HMGB1 binds to the Receptor for Advanced Glycation Endproducts (RAGE) and to the Toll-like Receptors (TLRs) 2 and 4, which are responsible for inflammatory responses. The activation of RAGE by HMGB1 induces tumor cell proliferation, migration, and invasion. HMGB1 induces migration in certain cell types.

Methods of Preventing Cancer

Several embodiments provided herein relate to methods of preventing cancer by providing or administering to a subject an effective amount of a HMGB1 antagonist described herein. The term "preventing" as used herein refers to prophylactically providing or administering a HMGB1 antagonist to a subject not having cancer and prior to the subject developing cancer. As used with respect to preventing cancer, the term "effective amount" refers to an amount of HMGB1 antagonist administered to the subject sufficient to partially or completely prevent or delay the occurrence of cancer. The term "partially" encompasses the notion that a HMGB1 antagonist can prevent cancer by delaying the onset or development of cancer in a subject who would otherwise have developed cancer sooner in the absence of HMGB1 antagonist administration. The term "partially" also encompasses the notion that administration of a HMGB1 antagonist in a subject not having cancer can prevent the severity of cancer that may thereafter develop, for example, in terms of size, aggressiveness, malignancy, metastatic potential, genomic instability, gene mutation, or responsiveness of the cancer to therapy. The term "completely" with respect to preventing cancer means that the subject not having cancer remains cancer-free for a given period of time after administration of a HMGB1 antagonist provided herein.

As used herein, "subject" includes organisms which are capable of suffering from a cancer, such as human and non-human animals. Preferred animals include human subjects. The term "non-human animals" includes all vertebrates, e.g., mammals, e.g., rodents, e.g., mice, rats, and non-human primates, e.g., sheep, dog, cow, chickens, amphibians, reptiles, etc. The term "administration" or "administering" includes routes of introducing a HMGB1 antagonist to perform its intended function.

Methods of Treating Cancer

Several embodiments provided herein relate to methods of treating cancer by administering to a subject having cancer an effective amount of a HMGB1 antagonist described herein. As used herein, the term "treating" refers to performing actions that lead to amelioration of the cancers referred to herein or of the symptoms accompanied therewith to a significant extent. The combination of said actions is encompassed by the term "treatment." Amelioration of a cancer includes but is not limited to reducing in the number of cancer cells in a subject or reducing the number of cancer cells at a specific site in the body of a subject. Said treatment as used herein also includes an entire restoration of the health with respect to the cancers referred to herein. It is to be understood that treatment as used in accordance with embodiments provided herein may not be effective in all subjects to be treated. However, a statistically significant portion of subjects suffering from a cancer referred to herein can be successfully treated. Whether a portion is statistically significant can be determined without by a person of ordinary skill in the art using various well known statistic evaluation tools, e.g., determination of confidence intervals, p-value determination, Student's t-test, Mann-Whitney test, etc.

As used with respect to treating cancer, the term "effective amount" refers to an amount of HMGB1 antagonist sufficient to treat cancer, which can be measured by a number of different parameters including, but not limited to, reduction in the size of a tumor in a subject having cancer, reduction in the growth rate or proliferation rate of a tumor in a subject having cancer, preventing metastasis or reducing the extent of metastasis, or extending the survival of a subject having cancer compared to control. Methods of detecting and quantifying tumor size, proliferation rate, metastasis and survival are known in the art. Thus, for example, an effective amount can be a dose in the ranges set forth below in the section entitled "dosages."

Cancer

Examples of cancers that can be treated or prevented by administering HMGB1 antagonists described herein include, but are not limited to, mesothelioma (e.g. malignant mesothelioma), an acute lymphoblastic leukemia, an acute myeloid leukemia, an adrenocortical carcinoma, an aids-related lymphoma, an anal cancer, an appendix cancer, an astrocytoma, an atypical teratoid, a basal cell carcinoma, a bile duct cancer, a bladder cancer, a brain stem glioma, a breast cancer, a burkitt lymphoma, a carcinoid tumor, a cerebellar astrocytoma, a cervical cancer, a chordoma, a chronic lymphocytic leukemia, a chronic myelogenous leukemia, a colorectal cancer, a craniopharyngioma, an endometrial cancer, an ependymoblastoma, an ependymoma, an esophageal cancer, an extracranial germ cell tumor, an extragonadal germ cell tumor, an extrahepatic bile duct cancer, a gallbladder cancer, a gastric cancer, a gastrointestinal stromal tumor, a gestational trophoblastic tumor, a hairy cell leukemia, a head and neck cancer, a hepatocellular cancer, a hodgkin lymphoma, a hypopharyngeal cancer, a hypothalamic and visual pathway glioma intraocular melanoma, a kaposi sarcoma, a laryngeal cancer, a medulloblastoma, a medulloepithelioma, a melanoma, a merkel cell carcinoma, a mouth cancer, a multiple endocrine neoplasia syndrome, a multiple myeloma, a mycosis fungoides, a nasal cavity and paranasal sinus cancer, a nasopharyngeal cancer, a neuroblastoma, a non-hodgkin lymphoma, a non-small cell lung cancer, an oral cancer, an oropharyngeal cancer, an osteosarcoma, an ovarian cancer, an ovarian epithelial cancer, an ovarian germ cell tumor, an ovarian low malignant potential tumor, a pancreatic cancer, a papillomatosis, a paranasal sinus and nasal cavity cancer, a parathyroid cancer, a penile cancer, a pharyngeal cancer, a pheochromocytoma, a pituitary tumor, a pleuropulmonary blastoma, a primary central nervous system lymphoma, a prostate cancer, a rectal cancer, a renal cell cancer, a retinoblastoma, a rhabdomyosarcoma, a salivary gland cancer, a sézary syndrome, a small cell lung cancer, a small intestine cancer, a soft tissue sarcoma, a squamous cell carcinoma, a squamous neck cancer, a testicular cancer, a throat cancer, a thymic carcinoma, a thymoma, a thyroid cancer, an urethral cancer, an uterine sarcoma, a vaginal cancer, a vulvar cancer, a waldenstrom macroglobulinemia, or a Wilms tumor.

In several embodiments, the cancer to be prevented or treated can be mesothelioma. As used herein, the terms mesothelioma and malignant mesothelioma (MM) can be used interchangeably. Human malignant mesothelioma (MM) is an aggressive and rapidly lethal cancer often associated with exposure to asbestos. Prognosis is poor, due to late-stage diagnosis and resistance to current therapies. Human malignant mesothelioma (MM) arises from the neoplastic transformation of mesothelial cells lining the pleural peritoneal and (rarely) pericardial cavities, and from the tunica vaginalis testis. MM has been linked to occupational and environmental exposure to asbestos, causing about 3,000 deaths per year in the U.S. and over 100,000 deaths per year worldwide. In the US, the incidence of MM is stable since 1994; the incidence of MM is increasing in Europe and in rapidly industrializing countries, such as India and China, where the use of asbestos is rising dramatically. MM is a very aggressive cancer, usually diagnosed at later stages, and is refractory to most therapeutic modalities, leading to poor prognosis and a median survival from diagnosis of 8-12 months.

Several embodiments provided herein are drawn to the discovery that various HMGB1 antagonists can prevent transformation of human mesothelial cells and thus prevent mesothelioma. Accordingly, in several embodiments, a method of preventing mesothelioma includes administering to a subject suspected of being at risk for developing mesothelioma an effective amount of a HMGB1 antagonist described herein sufficient to delay the onset or completely prevent the development of mesothelioma. For example, the subject can be associated with exposure to asbestos and therefore suspected of being at risk for developing mesothelioma.

Several embodiments provided herein are drawn to the discovery that various HMGB1 antagonists can reduce mesothelioma growth in vivo. Accordingly, in several embodiments, a method of treating mesothelioma includes providing or administering to a subject having mesothelioma an effective amount of a HMGB1 antagonist described herein sufficient to treat the mesothelioma.

HMGB1 Antagonists

Several types of HMGB1 antagonists are known in the art and can be used in embodiments provided herein relating to prevention or treatment of cancer, such as mesothelioma. Examples of HMGB1 antagonists that can be used in the embodiments of the present application include but are not limited to the several classes and specific members described below.

1. Anti-HMGB1 Antibodies

Provided herein are methods of preventing or treating cancer, such as mesothelioma, in a subject including administering an effective amount of an anti-HMGB1 antibody to the subject. Several anti-HMGB1 antibodies have been described and are known in the art and can be used in the methods provided herein. For example, numerous high affinity antibodies that specifically bind HMGB1 and antigenic fragments thereof are described in U.S. Patent Application Publication No. 2010/0061987, which is herein incorporated by reference in its entirety. Such antibodies disclosed therein are non-limiting examples of suitable anti-HMGB1 antibodies that can be used in embodiments for preventing or treating cancer provided in this application. For instance, antibodies designated therein as G2, G4 (ATCC# PTA-6258), G9, G12, G16, G20, G34, G35, S2 (ATCC# PTA-6142), S6 (ATCC# PTA-6143), S10, S12, S14, S16, S17, and E11 are examples of known anti-HMGB 1 antibodies that can be used in embodiments provided herein.

Additional examples of suitable anti-HMGB1 antibodies are described in U.S. Patent Application Publication No. 2009/0148453, which is herein incorporated by reference in its entirety. For instance, monoclonal antibodies designated therein as 6E6 HMGB1 mAb, 2E11 HMGB1mAb, 6H9 HMGB1 mAb, 10D4 HMGB1 mAb, 2G7 HMGB1 mAb, 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, and 4A10 HMGB1 mAb can be used in embodiments provided herein.

Furthermore, several anti-HMGB1 antibodies that can be used in embodiments provided herein are commercially available from vendors including Abbiotec (e.g., cat #s 252233, 252169, 250508), Abcam (e.g., HAP 46.5), AbD Serotec (e.g., P09429), Abgent (e.g., AT2384a), Abnova (e.g, H00003146-AP 45), ABR (e.g., KS1), Acris Antibodies GmbH (e.g., J2E1), AdipoGen (e.g., GIBY-1-4), ARP American Research Products (e.g. J2E1), Assay Biotech (e.g. C10316), Enzo Life Sciences, Aviva Systems Biology (e.g., ARP38110_T100), Biorbyt (e.g., orb27349), Cell Signalling Technology (e.g. 3935S), DiaPro Diagnostics (e.g., 010910) eBioscience (e.g., 14-9900-80), EMD Millipore (e.g., 07-584, MABE148), Epitomics (e.g., S0476), GeneTex (e.g., EPR3506, EPR3507), GenWay Biotech (e.g., 18-003-42680), Immuno-Biological Laboratories (e.g., IBAHM0915), LifeSpan BioSciences (e.g., LS-C36810-50), MBL International (e.g., 4C9), Novus Biologicals (e.g., H00003146), Origene Technologies (e.g., TA301448), Proteintech Group (e.g., 10829-1-AP), R&D Systems (e.g., 115603), Santa Cruz Biotechnology (e.g., J2E1), Sigma-Aldrich (e.g., SAB2101049, SAB4501401, WH0003146M8, SAB1403925, AV35646, AV38110, H9539, H9664), Pierce Antibodies (e.g., PA1-16926; MA1-20338, MA1-90941, etc.), and United States Biological (e.g., H6202-03).

High affinity antibodies of various embodiments can specifically bind a polypeptide comprising or alternatively consisting of a human HMGB1 polypeptide (SEQ ID NO:1 or SEQ ID NO:2; See Table 1). Full-length HMGB1 polypeptides of human and other animals are well known in the art (see, e.g., US20040005316; U.S. Pat. Nos. 6,468,533 and 6,448,223, which are incorporated herein by reference in their entireties).

TABLE 1

Human HMGB1 amino acid sequence (GenBank Acc. No.
NP_002119, all of the information of which is
incorporated herein by reference in its entirety)
(SEQ ID NO: 1)

MGKGDPKKPRGKMSSYAFFVQTCREEHKKKHPDASVNFSEFSKKCSERWK
TMSAKEKGKFEDMAKADKARYEREMKTYIP PKGETKKKFKDPNAPK
RPPSAFFLFCSEYRPKIKGEHPGLSIGDVAKKLGEMWNNTAADDKQPYE
KKAAKLKEKYEKDIAAYRAKGKPDAAKKGVVKAEKSKKKKEEEEDEEDE
EDEEEEEDEEDEDEEE DDDDE

Human HMGB1 amino acid sequence (GenBank ACC. NO.
AAA64970, all of the information of which is
incorporated herein by reference in its entirety)
(SEQ ID NO: 2)

MGKGDPKKPTGKMSSYAFFVQTCREEHKKKHPDASVNFSEFSKKCSERWK
TMSAKEKGKFEDMAKADKARYEREMKTYIPPKGETKKKFKDPNAPKRLPS
AFFLFCSEYRPKIKGEHPGLSIGDVAKKLGEMWNNTAADDKQPYEKKAAK
LKEKYEKDIAAYRAKGKPDAAKKGVVKAEKSKKKKEEEEDEEDEEDEEEE
EDEEDEEDEE DDDDE

In several embodiments, the antibodies that can specifically bind HMGB1 and antigenic fragments thereof can be humanized or human antibodies.

In several embodiments, antibodies can specifically bind HMGB1 and antigenic fragments thereof with a dissociation constant or $K_d$ ($k_{off}/k_{on}$) of less than $10^{-5}$M, or of less than $10^{-6}$M, or of less than $10^{-7}$M, or of less than $10^{-8}$ M, or of less than $10^{-9}$M, or of less than $10^{-10}$ M or of less than $10^{-11}$ M, or of less than $10^{-12}$ M, or of less than $10^{-13}$ M.

In another embodiment, the antibody can bind to HMGB1 and/or antigenic fragments thereof with a $K_{off}$ of less than $1 \times 10^{-3}$ s$^{-1}$. In other embodiments, the antibody binds to HMGB1 and antigenic fragments thereof with a $K_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^1$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$.

In another embodiment, the antibody binds to HMGB1 and/or antigenic fragments thereof with an association rate constant or $k_{on}$ rate of at least $10^{-5}$ M$^-$s$^{-1}$, at least $5 \times 10^{-5}$M$^{-1}$s$^{-1}$, at least $10^{-6}$M$^{-1}$s$^{-1}$, at least $5 \times 10^{-6}$M$^{-1}$s$^{-1}$, at least $10^{-7}$M$^{-1}$s$^{-1}$, at least $5 \times 10^{-7}$M$^{-1}$s$^{-1}$, or at least $10^{-8}$M$^{-1}$s$^{-1}$, or at least $10^{-9}$M$^{-1}$s$^{-1}$.

The high affinity antibodies include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. Any of the compositions of matter listed in this paragraph can be used in any of the methods described herein.

An additional nonexclusive embodiment includes high affinity antibodies that have certain preferred biochemical characteristics such as a particular isoelectric point (pI) or melting temperature (Tm).

In one embodiment, the high affinity antibodies have a pI ranging from 5.5 to 9.5. In one embodiment, the high affinity antibodies of several embodiments have a Tm ranging from about 65° C. to about 120° C.

In various embodiments, antibodies (and fragments thereof) that specifically bind HMGB1 with high affinity which have been deposited with the American Type Culture Collection can be used in the embodiments described herein (10801 University Boulevard, Manassas, Va. 20110-2209) and assigned ATCC Deposit Nos. PTA-6142 (Deposited Aug. 4, 2004), PTA-6143 (Deposited Aug. 4, 2004), PTA-6259 (Deposited Oct. 19, 2004) and PTA-6258 (Deposited Oct. 19, 2004) (also referred to herein as "S2", "S6", "S16", and "G4", respectively).

Other embodiments include particular antibodies (and fragments thereof) that specifically bind HMGB1 with high affinity and comprise at least one of the variable regions disclosed in U.S. Patent Application Publication No. 2010/0061987, which is incorporated herein by reference in its entirety. Antibodies having at least one, at least two, at least three, at least four at least five or at least 6 of the CDRs of the antibodies disclosed therein can be used in embodiments of the present application. Antibodies having at least one, at least two, at least three, at least four, at least five, or all six of the CDRs of the deposited antibodies can be used in various embodiments of the present application.

Further, any antibody that specifically binds the same epitope as the anti-HMGB1 antibodies disclosed in U.S. Patent Application Publication No. 2010/0061987 (incorporated herein by reference in its entirety) can be used in various embodiments. It is contemplated that these antibodies will bind the same epitope as the deposited antibodies with at least equal affinity, or better affinity, or less affinity.

As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. The antibodies of several embodiments provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992); each of which is incorporated herein by reference in its entirety.

Other antibodies specifically contemplated are "oligoclonal" antibodies. As used herein, the term "oligoclonal" antibodies" refers to a predetermined mixture of distinct monoclonal antibodies. Methods for generating oligoclonal antibodies are known in the art. See, e.g., "Examples Section", example 1, PCT publication WO 95/20401; U.S. Pat. Nos. 5,789,208 and 6,335,163; each of which is incorporated herein by reference in its entirety. In certain embodiments, oligoclonal antibodies consist of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618, which is incorporated herein by reference in its entirety). Oligoclonal antibodies are particularly useful when it is desired to target multiple epitopes on a single target molecule (e.g., HMGB1). Those skilled in the art will know or can determine what type of antibody or mixture of antibodies is applicable for an intended purpose and desired need. In particular, antibodies of several embodiments include immunoglobulin molecules and immunologically active portions of immunoglobulin molecules, i.e., molecules that contain an antigen binding site that specifically binds to an HMGB1 antigen (e.g., one or more complementarity determining regions (CDRs) of an anti-HMGB1 antibody). It is also specifically contemplated that the antibodies of several embodiments include immunoglobulin molecules and immunologically active portions of immunoglobulin molecules, i.e., molecules that contain an antigen binding site that specifically binds to an HMGB1 antigen (e.g., one or more complementarity determining regions (CDRs) of an anti-HMGB1 antibody). The immunoglobulin molecules of several embodiments can be of any type (e.g., IgG, IgE, IgM, IgD, IgA and IgY), class (e.g., IgG1, IgG2, IgG3, IgG4, IgA1 and IgA2) or subclass of immunoglobulin molecule Immunoglobulins may have both a heavy and light chain. An array of IgG, IgE, IgM, IgD, IgA, and IgY heavy chains may be paired with a light chain of the kappa or lambda forms.

The antibodies of embodiments provided herein also encompass immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" include full length antibodies and Fc variants thereof comprising Fc regions, or fragments thereof, comprising at least one novel amino acid residue described herein fused to an immunologically active fragment of an immunoglobulin or to other proteins as described herein. Such variant Fc fusions include but are not limited to, scFv-Fc fusions, variable region (e.g., VL and VH)-Fc fusions, scFv-scFv-Fc fusions Immunoglobulin molecules can be of any type (e.g., IgG, IgE, IgM, IgD, IgA and IgY), class (e.g., IgG1, IgG2, IgG3, IgG4, IgA1 and IgA2) or subclass.

Antibodies of several embodiments also encompass those that have half-lives (e.g., serum half-lives) in a mammal, (e.g., a human), of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311 and discussed in more detail below); each of which is incorporated herein by reference in its entirety.

In one embodiment, the antibodies may comprise modifications/substations and/or novel amino acids within their Fc domains such as, for example, those disclosed in Ghetie et al., 1997, Nat. Biotech. 15:637-40; Duncan et al, 1988, Nature 332:563-564; Lund et al., 1991, J. Immunol. 147: 2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. No. 10/370,749 and PCT Publications WO 94/2935; WO 99/58572; WO 00/42072; WO 02/060919, WO 04/029207; each of which is incorporated herein by reference in its entirety. Other modifications/substitutions of the Fc domain will be readily apparent to one skilled in the art.

Antibodies can comprise modifications/substations and/or novel amino acid residues in their Fc regions can be generated by numerous methods well known to one skilled in the art. Non-limiting examples include, isolating antibody coding regions (e.g., from hybridoma) and making one or more desired substitutions in the Fc region of the isolated antibody coding region. Alternatively, the variable regions of an antibody may be subcloned into a vector encoding an Fc region comprising one or modifications/substations and/ or novel amino acid residues.

Antibodies of several embodiments may also be modified to alter glycosylation, again to alter one or more functional properties of the antibody.

In various embodiments, the glycosylation of the antibodies can be modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861; each of which is incorporated herein by reference in its entirety.

Additionally or alternatively, an antibody of several embodiments can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342; each of which is incorporated herein by reference in its entirety.

The antibodies of several embodiments can be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387; each of which is incorporated herein by reference in its entirety.

Antibodies provided herein can include derivatives that are modified, i.e., by the covalent attachment of any type of molecule to the antibody such that covalent attachment does not prevent the antibody from binding an HMGB1 polypeptide or fragment thereof and/or generating a desired response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In several embodiments, the high affinity antibodies specifically bind a polypeptide comprising, or alternatively consisting of (or consisting essentially of) an HMGB1 polypeptide having at least 60% identity, or at least 70% identity, or at least 80% identity, at least 85% identity, at least 90% identity, at least 95% identity, or at least at least 97% identity, or at least 99% identity, or 100% identity to the human HMGB1 polypeptide of SEQ ID NO:1 or 2.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. When utilizing BLAST and Gapped BLAST programs, the default parameters of the respective programs (e.g., BLASTN) can be used. Accessible on the world wide web at www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Several embodiments include particular antibodies (and fragments thereof) that bind HMGB1 with high affinity and are designated "S2", "S6", "S16" and "G4," which have been deposited under the Budapest Treaty with the American Type Culture Collection (ATCC, 10801 University Boulevard, Manassas, Va. 20110-2209) and assigned ATCC Deposit Nos. PTA-6142, PTA-6143, PTA-6259 and PTA-6258, respectively, which are incorporated herein by reference in their entireties.

Several embodiments include particular antibodies designated 6E6 HMGB1 mAb, 2E11 HMGB1 mAb, 6H9 HMGB1 mAb, 10D4 HMGB1 mAb, 2G7 HMGB1 mAb, 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, and 4A10 HMGB1 mAb as described in U.S. Patent Application Publication No. 2009/0148453, which is incorporated herein by reference in its entirety.

Several embodiments also encompass variants of the above described known antibodies comprising one or more amino acid residue substitutions in the variable light ($V_L$) domain and/or variable heavy ($V_H$) domain. Several embodiments also encompass variants of the above described known antibodies with one or more additional amino acid residue substitutions in one or more $V_L$CDRs and/or one or more $V_L$CDRs. The antibody generated by introducing substitutions in the $V_H$ domain, $V_H$ CDRs, $V_L$ domain and/or $V_L$CDRs of the above described known antibodies can be tested in vitro and in vivo, for example, for its ability to bind to HMGB1 (by, e.g., immunoassays including, but not limited to ELISAs and BIACORE assay), or for its ability to inhibit HMGB1-induced cytokine release, prevent or treat cancer as described herein.

In other embodiments, antibodies can have at least one, at least two, at least three, at least four, at least five, or at least six of the CDRs of the known antibodies described above.

Various embodiments include antibodies that specifically bind to HMGB1 comprising derivatives of the $V_H$ domains, $V_H$ CDRs, $V_L$ domains, or $V_L$ CDRs described in U.S. Patent Application Publication Nos. 2010/0061987 and 2009/0148453 (incorporated herein in their entireties) that specifically bind to HMGB1. Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis are routinely used to generate amino acid substitutions. In one embodiment, the $V_H$ and/or $V_L$ CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions in the relative to the original $V_H$ and/or $V_L$ CDRs. In another embodiment, the $V_H$ and/or $V_L$ CDRs derivatives have conservative amino acid substitutions (e.g. supra) are made at one or more predicted non-essential amino acid residues (i.e., amino acid residues which are not critical for the antibody to specifically bind to HMGB1). Alternatively, mutations can be introduced randomly along all or part of the $V_H$ and/or $V_L$ CDR coding sequence, such as by saturation mutagenesis, and the resultant mutants can be screened for biological activity to identify mutants that retain activity. Following mutagenesis, the encoded antibody can be expressed and the activity of the antibody can be determined.

Several embodiments also encompass antibodies that specifically bind to HMGB1 or a fragment thereof, said antibodies comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of any of the known above described antibodies.

Various embodiments further encompass antibodies that specifically bind to HMGB1 or a fragment thereof, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the known above described antibodies. The determination of percent identity of two amino acid sequences can be determined by any method known to one skilled in the art, including BLAST protein searches.

Another embodiment includes the introduction of conservative amino acid substitutions in any portion of an anti-HMGB1 antibody described herein. It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 2.

TABLE 2

Families of Conservative Amino Acid Substitutions

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

The term "conservative amino acid substitution" also refers to the use of amino acid analogs or variants.

Methods of Generating Antibodies

High affinity antibodies or fragments that specifically bind to an HMGB1 polypeptide can be identified, for example, by immunoassays, BIACORE assay, or other techniques known to those of skill in the art.

The antibodies of several embodiments may be generated by any suitable method known in the art. Polyclonal antibodies to an antigen-of-interest can be produced by various procedures well known in the art. For example, an HMGB1 polypeptide can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981); each of which is incorporated herein by reference in its entirety. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. A "monoclonal antibody" may comprise, or alternatively consist of, two proteins, i.e., a heavy and a light chain.

Methods for producing and screening for specific antibodies using hybridoma technology are routine and well known in the art. In a non-limiting example, mice can be immunized with a HMGB1 polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a HMGB1 polypeptide. Ascites fluid, which generally contains high levels of antibodies, can be generated by immunizing mice with positive hybridoma clones.

Accordingly, several embodiments provide methods of generating monoclonal antibodies as well as antibodies produced by the method comprising culturing a hybridoma cell secreting an antibody wherein the hybridoma is generated by fusing splenocytes isolated from a mouse immunized with a HMGB1 antigen with myeloma cells and then screening the hybridomas resulting from the fusion for hybridoma clones that secrete an antibody able to bind a HMGB1 polypeptide.

Antibody fragments which recognize specific epitopes may be generated by known techniques. For example, Fab and F(ab')2 fragments of several embodiments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of various embodiments can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of several embodiments include those disclosed in PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988); each of which is incorporated herein by reference in its entirety.

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., *PNAS* 90:7995-7999 (1993); and Skerra et al., *Science* 240:1038-1040 (1988); each of which is incorporated herein by reference in its entirety.

For some uses, including in vivo use of antibodies in humans and in vitro detection assays, it may be desirable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397; each of which is incorporated herein by reference in its entirety. Humanized antibodies are antibody molecules from non-human species antibody that bind the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988); each of which is incorporated herein by reference in its entirety). Antibodies can be humanized using a variety of techniques known in the art including, for example, CDR-grafting (EP 239,400; PCT publication WO 91/09967; U.S. Pat. Nos. 5,225,539; 5,530,101; and 5,585,089; each of which is incorporated herein by reference in its entirety), veneering or resurfacing (EP 592,106; EP 519,596; Padlan, Molecular Immunology 28 (4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332); each of which is incorporated herein by reference in its entirety.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a HMGB1 polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995), which is incorporated herein by reference in its entirety. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; each of which is incorporated herein by reference in its entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988), which is incorporated herein by reference in its entirety).

Further, antibodies to HMGB1 polypeptides can, in turn, be utilized to generate anti-idiotype antibodies that "mimic" HMGB1 polypeptides using techniques well known to those skilled in the art (See, e.g., Greenspan & Bona, *FASEB J.* 7(5):437-444; (1989) and Nissinoff, *J. Immunol.* 147(8): 2429-2438 (1991); each of which is incorporated herein by reference in its entirety).

In several embodiments, antibodies provided herein are used therapeutically in vivo. Accordingly, the antibody can be modified to make it less immunogenic in the individual. For example, if the individual is human the antibody can be "humanized" where the complementarity determining region(s) of the antibody is transplanted into a human antibody (for example, as described in Jones et al., *Nature* 321:522-525, 1986; and Tempest et al., *Biotechnology* 9:266-273, 1991), which is incorporated herein by reference in its entirety.

Phage display technology can also be utilized to select antibody genes with binding activities towards the polypeptide either from repertoires of PCR amplified v-genes of lymphocytes from humans screened for possessing anti-B box antibodies or from naive libraries (McCafferty et al., *Nature* 348:552-554, 1990; and Marks, et al., *Biotechnology* 10:779-783, 1992, which is incorporated herein by reference in its entirety). The affinity of these antibodies can also be improved by chain shuffling (Clackson et al., *Nature* 352: 624-628, 1991, which is incorporated herein by reference in its entirety).

The choice of polypeptide to be used for the generation can be readily determined by one skilled in the art. Polypeptides may be chosen such that the antibody generated will not significantly cross-react or specifically bind to another member of the HMG protein family. Alternatively, polypeptides which share a large degree of homology between two or more members of the HMG protein family may be used for the generation of an antibody that can specifically bind (i.e., cross-react) with multiple members of the HMG protein family (e.g., HMGB1 and HMG2).

Methods of Producing Antibodies

The antibodies of several embodiments can be produced by any method known in the art for the synthesis of antibodies, in particular, by chemical synthesis or preferably, by recombinant expression techniques.

Recombinant expression of an antibody or fragment, derivative or analog thereof, (e.g., a heavy or light chain of an antibody or a single chain antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Various embodiments thus provide replicable vectors comprising a nucleotide sequence encoding an antibody molecule, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464; each of which is incorporated herein by reference in its entirety) and the variable domain of the antibody may be cloned into such a vector for expression of the entire heavy or light chain.

The expression vector is transferred to a host cell by conventional techniques and the transfected cells are then cultured by conventional techniques to produce an antibody. Thus, several embodiments include host cells containing a polynucleotide encoding an antibody, or a heavy or light chain thereof, or a single chain antibody, operably linked to a heterologous promoter. Vectors encoding both the heavy and light chains may be co-expressed in the host cell for expression of the entire immunoglobulin molecule, as detailed below.

A variety of host-expression vector systems may be utilized to express the antibody molecules described herein. Such host-expression systems represent vehicles by which the coding sequences of interest may be produced and subsequently purified, but also represent cells which may, when transformed or transfected with the appropriate nucleotide coding sequences, express an antibody molecule in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, 3T3, PerC6 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)). Also see, e.g., U.S. Pat. Nos. 5,827,739, 5,879,936, 5,981,216, and 5,658,759; each of which is incorporated herein by reference in its entirety.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), which is incorporated herein by reference in its entirety, in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)), each of which is incorporated herein by reference in its entirety; and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA* 81:355-359 (1984), which is incorporated herein by reference in its entirety). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987), which is incorporated herein by reference in its entirety).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, NS0, Per.C6 and in particular, breast cancer cell lines such as, for example, BT483, Hs578T, HTB2, BT20 and T47D, and normal mammary gland cell lines such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Proc Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 Clinical Pharmacy 12:488-505; Wu and Wu, Biotherapy 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, 1993, *TIB TECH* 11(5): 155-215); and hygro, which confers resistance to hygromycin (Santerre et al., *Gene* 30:147 (1984), each of which is incorporated herein by reference in its entirety). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), each of which is incorporated herein by reference in its entirety.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987), which is incorporated herein by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983), which is incorporated herein by reference in its entirety).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:562 (1986); Kohler, *Proc. Natl. Acad. Sci. USA* 77:2197 (1980), which is incorporated herein by reference in its entirety). The coding sequences for the heavy and light chains may comprise cDNA or genomic DNA.

Once an antibody molecule has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies or fragments thereof can be fused to heterologous polypeptide sequences described herein or otherwise known in the art, to facilitate purification.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), which is incorporated herein by reference in its entirety, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984), which is incorporated herein by reference in its entirety) and the "flag" tag.

The antibodies described herein include derivatives that are modified (e.g., by the covalent attachment of any type of molecule to the antibody). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. EP 413, 622, each of which is incorporated herein by reference in its entirety. Embodiments provided herein encompass the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

Various embodiments encompass the use of antibodies or fragments thereof recombinantly fused or chemically conjugated (including both covalent and non-covalent conjugations) to a heterologous protein or polypeptide (or fragment thereof, specifically to a polypeptide of at least 10, at least 20, at least 30, at least 40, at least 50, at least 60, at least 70, at least 80, at least 90 or at least 100 amino acids) to generate fusion proteins. In some embodiments, the antibodies or fragments thereof can be recombinantly fused or chemically conjugated (including both covalent and non-covalent conjugations) to a heterologous protein or polypeptide (or fragment thereof, specifically to a polypeptide of at least about 10, at least about 20, at least about 30, at least about 40, at least about 50, at least about 60, at least about 70, at least about 80, at least about 90 or at least about 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, each of which is incorporated herein by reference in its entirety.

Several embodiments include formulations comprising heterologous proteins, peptides or polypeptides fused or conjugated to antibody fragments. For example, the heterologous polypeptides may be fused or conjugated to a Fab fragment, Fd fragment, Fv fragment, F(ab)2 fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341, each of which is incorporated herein by reference in its entirety.

Additional fusion proteins, e.g., of antibodies that specifically bind HMGB1 or fragments thereof (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313, each of which is incorporated herein by reference in its entirety. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to a C/CLP may be recombined with one or more components, motifs, sections, parts, domains, fragments, etc. of one or more heterologous molecules.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, which is incorporated herein by reference in its entirety, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767, which is incorporated herein by reference in its entirety) and the "flag" tag.

Various embodiments further encompass antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900, which is incorporated herein by reference in its entirety, for metal ions which can be conjugated to antibodies for use as diagnostics. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include but are not limited to, $^{125}$I, $^{131}$I, $^{111}$In or $^{99}$Tc, in addition positron emitting metals using various positron emission tomographies, nonradioactive paramagnetic metal ions, and molecules that are radiolabelled or conjugated to specific radioisotopes can be conjugated to the antibodies described herein.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publications WO 03/075957, which is incorporated herein by reference in its entirety.

The conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567-1574 (1994)), VEGI (See, International Publication No. WO 99/23105), each of which is incorporated herein by reference in its entirety, CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.* 62:119-58 (1982), each of which is incorporated herein by reference in its entirety.

The antibodies can be conjugated to other polypeptides. Methods for fusing or conjugating antibodies to polypeptide moieties are known in the art. See, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337, each of which is incorporated herein by reference in its entirety. The fusion of an antibody to a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171. Alternatively, an antibody can be conjugated to a second antibody to form an antibody heteroconjugate as described by Segal in U.S. Pat. No. 4,676,980, each of which is incorporated herein by reference in its entirety.

2. Anti-RAGE Antibodies

Provided herein are methods of preventing or treating cancer, such as mesothelioma, in a subject including administering an effective amount of an anti-RAGE antibody to the subject.

The Receptor for Advanced Glycation Endproducts (RAGE) is a multi-ligand receptor of the immunoglobulin superfamily. Extracellular domain of RAGE includes one N-terminal V-type and two C2-type immunoglobulin domains usually termed C1 and C2. Ligands of RAGE include HMGB1. The activation of RAGE by HMGB1 induces tumor cell proliferation, migration, and invasion (Ulloa L, Messmer D. High-mobility group box 1 (HMGB1) protein: friend and foe. *Cytokine Growth Factor Rev.* 2006; 17:189-201; Huttunen H J, Rauvala H. Amphoterin as an extracellular regulator of cell motility: from discovery to disease. *J Intern Med.* 2004; 255:351-366), each of which is incorporated herein by reference in its entirety.

Several anti-RAGE antibodies have been described and are known in the art and can be used in the methods provided herein. For example, numerous high affinity antibodies that specifically bind RAGE and antigenic fragments thereof are described in US Patent Application Publication No. 2011/0104174, which is herein incorporated by reference in its entirety. Such antibodies disclosed therein are non-limiting examples of suitable anti-RAGE antibodies that can be used in embodiments for preventing or treating cancer provided in this application. Also, several humanized anti-RAGE antibodies are described in US Patent Application Publication Nos. 2010/0143349 and 2007/0286858, which are both herein incorporated by reference in their entirety. Anti-RAGE antibodies can be produced, modified, and conjugated as described above using known techniques.

3. Box a Polypeptide Antagonists, Soluble RAGE Polypeptide Antagonists, and Heparin Polypeptide Antagonists Provided herein are methods of preventing or treating cancer, such as mesothelioma, in a subject including administering an effective amount of a Box A polypeptide, fragment, or variant thereof to the subject. The human HMGB1 Box A polypeptide has the amino acid sequence: (PTG-KMSSYAFFVQTCREEHKKKHPDASVNFSEFSKKC-SERWKTMSAKEKGKFEDM AKADKARYEREMKTY-IPPKGET) (SEQ ID NO: 3).

Structural function analysis of HMGB1-truncated mutants has revealed that the Box A domain of HMGB1 competitively displaces the binding of HMGB1 to macrophages, specifically antagonizing HMGB1 activities. Administration of Box A rescues mice from sepsis even when treatment has been initiated as late as 24 hours after surgical induction of sepsis. HMGB1 antagonists or inhibitors selected from the group of antibodies or antibody fragments that bind to an HMGB1 protein, HMGB1 gene antisense sequences and HMGB1 receptor antagonists are known and disclosed in U.S. Pat. No. 6,468,533, International PCT Application Publication No. WO 02/074337 and US Patent Application No. 2003/0144201, which are each herein incorporated by reference in their entirety and can be used in the embodiments described herein. International PCT Patent Application Publication WO 2006/024547, herein incorporated by reference in its entirety, discloses polypeptide variants of the HMGB1 Box A, or of biologically active fragments of HMGB1 Box A, which are obtained through systematic mutations of single amino acids of the wild-type HMGB1 Box-A protein.

Several embodiments provided herein include the Box A polypeptide and variants or fragments thereof that have HMGB1 antagonistic activity. For example, a variants or fragment of Box A having HMGB1 antagonistic activity can have at least about 60% identity, at least about 70% identity, at least about 80% identity, at least about 85% identity, at least about 90% identity, at least about 95% identity, at least about 97% identity, or at least 99% identity to the Box A polypeptide amino acid sequence (SEQ ID NO:3), or any percent identity in between any two of the aforementioned percentages. In several embodiments, variants or fragments of Box A polypeptide can include conservative amino acid substitutions as explained above. Furthermore, any Box A polypeptide, fragment, or variant thereof can be modified as a peptidomimetic as described below.

Provided herein are methods of preventing or treating cancer, such as mesothelioma, in a subject including administering an effective amount of a soluble RAGE polypeptide, fragment, or variant thereof to the subject. Examples of soluble RAGE polypeptides that can be used in several embodiments for preventing or treating cancer include, but are not limited, to those described in U.S. Pat. No. 6,465,422; U.S. Pat. No. 7,732,400, U.S. Pat. No. 6,555,651, and U.S. Pat. No. 7,485,697, each of which is herein incorporated by reference in its entirety. Without being bound by theory, it is contemplated that soluble RAGE polypeptides provided herein can inhibit the function of the HMGB1-RAGE interaction. In several embodiments, variants or fragments of soluble RAGE polypeptides can include conservative amino acid substitutions as explained above. Furthermore, any soluble RAGE polypeptide, fragment, or variant thereof can be modified as a peptidomimetic as described below.

Provided herein are methods of preventing or treating cancer, such as mesothelioma, in a subject including administering an effective amount of a heparin polypeptide, fragment, derivative, or variant thereof to the subject. Examples of heparin polypeptides, fragments, derivatives, or variants thereof that can be used in several embodiments for preventing or treating cancer include, but are not limited, to those described in U.S. Patent Application Publication No. 2009/003640, which is herein incorporated by reference in its entirety. Non-limiting examples of a heparin polypeptide derivative that can be used in several embodiments include desulfated heparin, such as heparin desulfated at the 2-O and/or 3-O positions (ODSH). Without being bound by theory, it is contemplated that heparin polypeptides provided herein, such as ODSH, can inhibit the function of the HMGB1-RAGE interaction. In several embodiments, variants or fragments of heparin polypeptides can include conservative amino acid substitutions as explained above. Furthermore, any heparin polypeptide, fragment, or variant thereof can be modified as a peptidomimetic as described below.

Provided herein are methods of preventing or treating cancer, such as mesothelioma, in a subject including administering an effective amount of an agent that disrupts the HMGB1-RAGE interaction to the subject. In some embodiments, such agent can be a small chemical molecule. In other embodiments, the agent can be an antibody or a polypeptide. Examples of such agents include, but are not limited to, the soluble RAGE polypeptides and heparin polypeptides described above. Polypeptide agents that disrupt the HMGB1-RAGE interaction can be modified as a peptidomimetic as described below.

a. Terminal Modifications

Those of skill in the art recognize that a variety of techniques are available for constructing peptidomimetics with the same or similar desired biological activity as the corresponding peptide compound but with more favorable activity than the peptide with respect to solubility, stability, and susceptibility to hydrolysis and proteolysis. See, for example, Morgan, et al. 1989 Ann Rep Med Chem 24:243-252, which is incorporated herein by reference in its entirety. The following describes methods for preparing peptidomimetics modified at the N-terminal amino group, the C-terminal carboxyl group, and/or changing one or more of the amido linkages in the peptide to a non-amido linkage. It is understood that two or more such modifications can be coupled in one peptidomimetic structure (for example, modification at the C-terminal carboxyl group and inclusion of a —CH2-carbamate linkage between two amino acids in the peptide).

1). N-Terminal Modifications

The peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —NHCH3 or —NH(CH3)2), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (See, for example, Murray, et al. 1995 Burger's Medicinal Chemistry and Drug Discovery 5th ed., Vol. 1, Manfred E. Wolf, ed., John Wiley and Sons, Inc., which is incorporated herein by reference in its entirety) Specifically, the N-terminal amino group can then be reacted as follows:

(a) to form an amide group of the formula RC(O)NH— where R is as defined above by reaction with an acid halide [for example, RC(O)Cl] or symmetric anhydride. Typically, the reaction can be conducted by contacting about equimolar or excess amounts (for example, about 5 equivalents) of an acid halide to the peptide in an inert diluent (for example, dichloromethane) preferably containing an excess (for example, about 10 equivalents) of a tertiary amine, such as diisopropylethylamine, to scavenge the acid generated during reaction. Reaction conditions are otherwise conventional (for example, room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (for example, about 5 equivalents) can be employed and the amino group is converted to the succinimide by methods well known in the art including the use of an excess (for example, ten equivalents) of a tertiary amine such as diisopropylethylamine in a suitable inert diluent (for example, dichloromethane). See, for example, Wollenberg, et al., U.S. Pat. No. 4,612,132 which is incorporated herein by reference in its entirety. It is understood that the succinic group can be substituted with, for example, C2-C6 alkyl or —SR substituents which are prepared in a conventional manner to provide for substituted succinimide at the N-terminus of the peptide. Such alkyl substituents are prepared by reaction of a lower olefin (C2-C6) with maleic anhydride in the manner described by Wollenberg, et al., supra and —SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ—Cl (i.e., benzyloxycarbonyl chloride) or a substituted CBZ—Cl in a suitable inert diluent (for example, dichloromethane) preferably containing a tertiary amine to scavenge the acid generated during the reaction;

(d) to form a sulfonamide group by reaction with an equivalent amount or an excess (for example, 5 equivalents) of R—S(O)2Cl in a suitable inert diluent (dichloromethane) to convert the terminal amine into a sulfonamide where R is as defined above. Preferably, the inert diluent contains excess tertiary amine (for example, ten equivalents) such as diisopropylethylamine, to scavenge the acid generated during reaction. Reaction conditions are otherwise conventional (for example, room temperature for 30 minutes);

(e) to form a carbamate group by reaction with an equivalent amount or an excess (for example, 5 equivalents) of R—OC(O)Cl or R—OC(O)OC6H4-p-NO2 in a suitable inert diluent (for example, dichloromethane) to convert the terminal amine into a carbamate where R is as defined above. Preferably, the inert diluent contains an excess (for example, about 10 equivalents) of a tertiary amine, such as diisopropylethylamine, to scavenge any acid generated during reaction. Reaction conditions are otherwise conventional (for example, room temperature for 30 minutes); and (f) to form a urea group by reaction with an equivalent amount or an excess (for example, 5 equivalents) of R—N=C=O in a suitable inert diluent (for example, dichloromethane) to convert the terminal amine into a urea (i.e., RNHC(O)NH—) group where R is as defined above. Preferably, the inert diluent contains an excess (for example, about 10 equivalents) of a tertiary amine, such as diisopropylethylamine. Reaction conditions are otherwise conventional (for example, room temperature for about 30 minutes).

2). C-Terminal Modifications

In preparing peptidomimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, for example, methanol. Side chain protecting groups are then removed in the usual fashion by treatment with hydrogen fluoride to obtain the desired ester.

In preparing peptidomimetics wherein the C-terminal carboxyl group is replaced by the amide —C(O)NR3R4, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH2). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR1 where R and R1 are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH2Cl2), dimethyl formamide (DMF) mixtures. The cyclic peptide is then formed by internal displacement of the activated ester with the N-terminal amine Internal cyclization as opposed to polymerization can be enhanced by use of very dilute solutions. Such methods are well known in the art.

One can also cyclize the peptides, or incorporate a desamino or descarboxy residue at the termini of the peptide, so that there is no terminal amino or carboxyl group, to decrease susceptibility to proteases or to restrict the conformation of the peptide. C-terminal functional groups of the compounds of various embodiments include amide, amide lower alkyl, amide di(lower alkyl), lower alkoxy, hydroxy, and carboxy, and the lower ester derivatives thereof, and the pharmaceutically acceptable salts thereof.

b. Backbone Modifications

Other methods for making peptide derivatives are described in Hruby, et al. 1990 *Biochem J* 268(2):249-262, incorporated herein by reference. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan, et al. 1989 *Ann Rep Med Chem* 24:243-252, incorporated herein by reference. These techniques include replacing the peptide backbone with a backbone composed of phosphonates, amidates, carbamates, sulfonamides, secondary amines, and N-methylamino acids.

Peptidomimetics wherein one or more of the peptidyl linkages [—C(O)NH—] have been replaced by such linkages as a —CH$_2$-carbamate linkage, a phosphonate linkage, a —CH$_2$-sulfonamide linkage, a urea linkage, a secondary amine (—CH$_2$NH—) linkage, and an alkylated peptidyl linkage [—C(O)NR$^6$— where R$^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —CH$_2$-carbamate linkage (—CH$_2$OC(O)NR—), then the carboxyl (—COOH) group of a suitably protected amino acid is first reduced to the —CH$_2$OH group which is then converted by conventional methods to a —OC(O)Cl functionality or a para-nitrocarbonate —OC(O)O—C$_6$H$_4$-p-NO$_2$ functionality. Reaction of either of such functional groups with the free amine or an alkylated amine on the N-terminus of the partially fabricated peptide found on the solid support leads to the formation of a —CH$_2$OC(O)NR— linkage. For a more detailed description of the formation of such —CH$_2$-carbamate linkages, see Cho, et al. 1993 *Science* 261:1303-1305.

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a —CH$_2$-sulfonamide linkage can be achieved by reducing the carboxyl (—COOH) group of a suitably protected amino acid to the —CH$_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH2-S(O)$_2$Cl functional group which replaces the carboxyl group of the otherwise suitably protected amino acid. Use of this suitably protected amino acid analogue in peptide synthesis provides for inclusion of a —CH$_2$S(O)$_2$NR— linkage, which replaces the amido linkage in the peptide thereby providing a peptidomimetic. For a more complete description on the conversion of the carboxyl group of the amino acid to a —CH$_2$S(O)$_2$Cl group, see, for example, Weinstein, B., 1983 *Chemistry & Biochemistry of Amino Acids, Peptides and Proteins* Vol. 7, pp. 267-357, Marcel Dekker, Inc., New York, which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —CH$_2$NH— linkage replaces the amido linkage in the peptide can be prepared by employing, for example, a suitably protected dipeptide analogue wherein the carbonyl bond of the amido linkage has been reduced to a CH$_2$ group by conventional methods. For example, in the case of diglycine, reduction of the amide to the amine will yield after deprotection H$_2$NCH$_2$CH$_2$NHCH$_2$COOH which is then used in N-protected form in the next coupling reaction. The preparation of such analogues by reduction of the carbonyl group of the amido linkage in the dipeptide is well known in the art (see, for example, M. W. Remington 1994 *Meth Mol Bio* 35:241-247, which is incorporated herein by reference in its entirety).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One example of a tertiary amine is diisopropylethylamine which is typically employed in about 10-fold excess. The reaction results in incorporation into the peptidomimetic of an amino acid analogue having a non-peptidyl linkage. Such substitution can be repeated as desired such that from zero to all of the amido bonds in the peptide have been replaced by non-amido bonds.

Such peptides or peptidomimetics described above can have a length of less than 10, less than 11, less than 12, less than 13, less than 14, less than 15, less than 20, less than 25, less than 30, less than 35, less than 40, less than 45, less than 50, less than 75, less than 100, less than 200, less than 300, less than 400 or less than 500 residues. Accordingly, a variant or fragment of Box A having HMGB1 antagonistic activity can have at least about 60% identity, at least about 70% identity, at least about 80% identity, at least about 85% identity, at least about 90% identity, at least about 95% identity, at least about 96% identity, at least about 97% identity, at least about 98% identity, or at least 99% identity to the Box A polypeptide amino acid sequence (SEQ ID NO:3), or any percent identity in between any two of the aforementioned percentages, with respect to any of the aforementioned peptide or peptidomimetic lengths.

4. Anti-Inflammatory Compounds

Several embodiments provided herein are drawn to the discovery that administration of anti-inflammatory drugs can inhibit transformation of human mesothelial cells and thus prevent mesothelioma. Also several embodiments relate to the discovery that administration of anti-inflammatory drugs can reduce tumor growth in vivo. As such, several embodiments provided herein relate to methods of preventing or treating cancer, such as mesothelioma, in a subject including administering an effective amount of an anti-inflammatory compound to the subject.

Examples of anti-inflammatory drugs suitable for use in various embodiments include, but are not limited to, non-steroidal anti-inflammatory drugs (NSAIDs) such as salicylates, for example, aspirin, pyrazolone derivatives, for example, phenylbutazone, onyphenbutazone, antipyrine, aminopyrine, dipyrone and apazone, indomethacin, sulindac, fenamates, for example, mefenamic, meclofenamic, flufenamic, tolfenamic and etofenamice acids, aryl acetic acid and propionic acid compounds, for example, 2-(p-isobutylphenyl)propionic acid (generic name ibuprofen), alpha-methyl-4-(2-thienylcarbonyl)benzene acetic acid (generic name suprofen), 4,5-diphenyl-2-oxazole propionic acid (generic name oxprozin), rac-6-chloro-alphamethyl-carbazole-2-acetic acid (generic name carprofen), 2-(3-phenyloxyphenyl)-propionic acid, the calcium salt dihydrate thereof (these compounds being referred to generically as fenoprofen and fenoprofen calcium), 2-(6-methoxy-2-naphthyl)propionic acid (generic name naproxen, the generic name of the sodium salt is naproxen sodium), 4-(1,3-dihydro-1-oxo-2H-isoindol-2-yl)-a-methylbenzene acetic acid (generic name indoprofen), 2-(3-benzoylphenyl)propionic acid (generic name ketoprofen), and 2-(2-fluoro-4-biphenylyl)propionic acid (generic name flurbiprofen), and 1-5-(4-methylbenzoyl)-1H-pyrrole-2-acetic acid (generic name tolmetin). Non-steroidal anti-inflammatory drugs also include, for example, sodium 5-(4-chlorobenzoyl)-1,4-dimethyl-1H-pyrrole-2-acetate dihydrate (generically referred to as zomepirac sodium), 4-hydroxy-2-methyl-N-(2-pyridyl-2H-1,2-benzothiazine-3-carboxamide-1,1-di-oxide (generic name piroxicam), 2',4'-difluoro-4-hydroxy-3-biphenylcarboxylic acid (generic name diflunisal), or 1-isopropyl-7-methyl-4-phenyl-2(1H)-quinozolinone (generic name proquazone), phenylacetic acid derivatives, for example, diclofenac, etodolac and nabumetone.

In several embodiments, methods of preventing or treating cancer, such as mesothelioma, in a subject include administering an effective amount of an aspirin to the subject.

Additional examples of anti-inflammatory drugs suitable for use in various embodiments include, but are not limited to, esters of an alpha-ketoalkanoic acid, for example, a C$_3$-C$_8$ straight-chained or branched alpha-ketoalkanoic acid ester. Examples include alpha-keto-butyrate, alpha-ketopentanoate, alpha-keto-3-methyl-butyrate, alpha-keto-4-methyl-pentanoate or alpha-keto-hexanoate. A variety of groups are suitable for the ester position of the molecule, e.g., alkyl, aralkyl, alkoxyl, carboxyalkyl, glyceryl or dihydroxy acetone. Specific examples include ethyl, propyl, butyl, carboxymethyl, acetoxymethyl, carbethoxymethyl and ethoxymethyl. An example of a suitable alkyl ester is ethyl ester. Thiolesters (e.g., wherein the thiol portion is cysteine or homocysteine) are also included. Further suitable examples include ethyl pyruvate, propyl pyruvate, carboxymethyl pyruvate, acetoxymethyl pyruvate, carbethoxymethymethyl pyruvate, ethoxymethyl pyruvate, ethyl alpha-keto-butyrate, ethyl alpha-keto-pentanoate, ethyl alpha-keto-3-methyl-butyrate, ethyl alpha-keto-4-methyl-pentanoate, or ethyl alpha-keto-hexanoate.

In several embodiments, methods of preventing or treating cancer, such as mesothelioma, in a subject include administering an effective amount of ethyl pyruvate to the subject. Ethyl pyruvate has been shown to prevent HMGB1 secretion (Fink M P. Ethyl pyruvate: a novel treatment for sepsis. Curr Drug Targets. 2007; 8(4):515-8, which is incorporated herein by reference in its entirety).

Combinations of HMGB1 Antagonists

In several embodiments, any of the above described HMGB1 antagonists can be used in combination the methods of preventing or treating cancer, such as mesothelioma. For example, in some embodiments, a method of preventing or treating cancer includes administering at least two of any of the HMGB1 antagonists selected from the group consisting of: anti-HMGB1 antibody, anti-RAGE antibody, BoxA polypeptide antagonist, and anti-inflammatory compound. In some embodiments, a method of preventing or treating cancer includes administering at least two of any of the HMGB1 antagonists selected from the group consisting of: anti-HMGB1 antibody, BoxA polypeptide antagonist, aspirin, and ethyl pyruvate.

Combinations with Other Chemotherapeutic Agents

Some embodiments relate to combination treatment and/or adjunct therapies for treating a cancer, such as for example, malignant mesothelioma. For example, the cancer such as malignant mesothelioma can be treated with an effective combination of any of the treatments and therapies described herein (e.g., anti-HMGB1 antibody, other protein or antagonist; BoxA polypeptide; anti-inflammatory, including aspirin, etc.). In some aspects, a patient suffering from or susceptible to malignant mesothelioma can be treated with a chemotherapeutic suitable for treating or preventing the cancer (e.g., malignant mesothelioma) in combination with or the other therapies described herein. Non-limiting examples of chemotherapeutics that can be used for combination and adjunct therapies for malignant mesothelioma include Cisplatin, Gemcitabine, ALIMTA chemotherapeutic, Carboplatin, ONCONASE chemotherapeutic, NAVELBINE chemotherapeutic, and the like. The chemotherapeutics can be administered in any suitable dosage that is effective to treat the cancer or reduce the cancer, including in their approved dosages, for example. In some aspects the other therapies can be the adjunct therapies that are used alone or in combination with the chemotherapeutic. In some aspects they can be used as adjunct therapies where the chemotherapy does not satisfactorily or completely resolve the cancer. In other aspects the chemotherapeutic can be the adjunct therapy.

Rational Drug Design

HMGB1 can be a therapeutic target in a variety of cancers. For example, HMGB1 can be therapeutically targeted in any cancer selected from the group consisting of: melanoma, epithelial cancer, squamous cell cancer, small cell lung cancer, non-small cell lung cancer, glioma, hepatocellular (liver) carcinoma, thyroid tumor, a leukemia, gastric (stomach) cancer, prostate cancer, breast cancer, ovarian cancer, bladder cancer, lung cancer, glioblastoma, endometrial cancer, kidney cancer, colon cancer, ovarian cancer, hepatocellular cancer, pancreatic cancer, esophageal carcinoma, head and neck cancers, esophageal cancer, lymphoma, mesothelioma, sarcomas, carcinomas, biliary (cholangiocarcinoma), small bowel adenocarcinoma, pediatric malignancies and epidermoid carcinoma. Thus, several embodiments relate to rational drug design to target HMGB1.

Rational drug design involving polypeptides requires identifying and defining a first peptide with which the designed drug is to interact, and using the first target peptide to define the requirements for a second peptide. With such requirements defined, one can find or prepare an appropriate peptide or non-peptide that meets all or substantially all of the defined requirements. Thus, one goal of rational drug design is to produce structural or functional analogs of biologically active polypeptides of interest or of small molecules with which they interact (e.g., agonists, antagonists, null compounds) in order to fashion drugs that are, for example, more or less potent forms of the ligand. (See, e.g., Hodgson, *Bio. Technology* 9:19-21 (1991), which is herein incorporated by reference in its entirety). An example of rational drug design is shown in Erickson et al., *Science* 249:527-533 (1990), which is herein incorporated by reference in its entirety. Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573; and 5,888,738; each of which is herein incorporated by reference in its entirety).

The use of molecular modeling as a tool for rational drug design and combinatorial chemistry has dramatically increased due to the advent of computer graphics. In some embodiments, software is used to compare regions of HMGB1 and molecules that interact with HMGB1 (collectively referred to as "binding partners"—e.g., anti-HMGB1 antibodies), and fragments or derivatives of these molecules with other molecules, such as peptides, peptidomimetics, and chemicals, so that therapeutic interactions can be predicted and designed. (See Schneider, *Genetic Engineering News* December: page 20 (1998), Tempczyk et al., *Molecular Simulations Inc. Solutions* April (1997) and Butenhof, *Molecular Simulations Inc. Case Notes* (August 1998) for a discussion of molecular modeling; each of which is herein incorporated by reference in its entirety).

For example, the protein sequence of an HMGB1 or binding partner, or domains of these molecules (or nucleic acid sequence encoding these polypeptides or both), can be entered onto a computer readable medium for recording and manipulation. It will be appreciated by those skilled in the art that a computer readable medium having these sequences can interface with software that converts or manipulates the sequences to obtain structural and functional information, such as protein models. That is, the functionality of a software program that converts or manipulates these sequences includes the ability to compare these sequences to other sequences or structures of molecules that are present on publicly and commercially available databases so as to conduct rational drug design.

The HMGB1 or binding partner polypeptide or nucleic acid sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment.

As a starting point to rational drug design, a two or three dimensional model of a polypeptide of interest is created (e.g., HMGB1, or a binding partner). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221-239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, 4$^{th}$ Edition, Prentice-Hall, N.J. (1972), which is herein incorporated by reference in its entirety).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850, which is herein incorporated by reference in its entirety). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052). Conventional homology modeling techniques have been used routinely to build models of proteases and antibodies. (Sowdhamini et al., *Protein Engineering* 10:207, 215 (1997), which is herein incorporated by reference in its entirety). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

Additionally, the techniques described above can be supplemented with techniques in molecular biology to design models of the protein of interest. For example, a polypeptide of interest can be analyzed by an alanine scan (Wells, Methods in Enzymol. 202:390-411 (1991), which is herein incorporated by reference in its entirety) or other types of site-directed mutagenesis analysis.

Once a model of the polypeptide of interest is created, it can be compared to other models so as to identify new members of the HMGB1 family and binding partners. By starting with the amino acid sequence or protein model of HMGB1 or a binding partner, for example, molecules having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences).

Accordingly, the protein sequence corresponding to an HMGB1 or a binding partner or a fragment or derivative of these molecules can be compared to known sequences on a protein basis. Protein sequences corresponding to an HMGB1, or a binding partner or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences are compared to publicly known amino acid sequences of Swissprot using BLASTX with the parameter E=0.001. The molecules identified as members of the family of HMGB1 or candidate binding partners desirably have at least 35% homology and preferably have 40%, 45%, 50% or 55% or greater homology to HMGB1.

In another embodiment, computer modeling and the sequence-to-structure-to-function paradigm is exploited to identify more members of the HMGB1 family candidate binding partners. By this approach, first the structure of an HMGB1 or a candidate binding partner having a known response in a characterization assay is determined from its sequence using a threading algorithm, which aligns the sequence to the best matching structure in a structural database. Next, the protein's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703-711 (1998) and Fetrow and Skolnick, *J. Mol. Biol.* 281: 949-968 (1998); each of which is herein incorporated by reference in its entirety.

By a similar approach, a candidate binding partner can be identified and manufactured as follows. First, a molecular model of one or more molecules that are known to interact with HMGB1 or portions of these molecules that interact with an HMGB1 are created using one of the techniques discussed above or as known in the art. Next, chemical libraries and databases are searched for molecules similar in structure to the known molecule. That is, a search can be made of a three dimensional data base for non-peptide (organic) structures (e.g., non-peptide analogs, and/or dipeptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., *Acta Crystallogr., B*35: 2331-2339 (1979), which is herein incorporated by reference in its entirety. The identified candidate binding partners that interact with HMGB1 can then be analyzed in a functional assay and new molecules can be modeled after the candidate binding partners that produce a desirable response. By cycling in this fashion, libraries of molecules that interact with HMGB1 and produce a desirable or optimal response in a functional assay can be selected.

By another approach, protein models of binding partners that interact with an HMGB1 can be made by the methods described above and these models can be used to predict the interaction of new molecules. Once a model of a binding partner is identified, the active sites or regions of interaction can be identified. Such active sites might typically be ligand binding sites. The active site can be identified using methods known in the art including, for example, from the amino acid sequences of peptides, from the nucleotide sequences of nucleic acids, or from study of complexes of the HMGB1 with a ligand. In the latter case, chemical or X-ray crystallographic methods can be used to find the active site by finding where on the HMGB1 the complexed ligand is found (e.g. protein-protein module). Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

Finally, having determined the structure of the active site of the known binding partner, either experimentally, by modeling, or by a combination, candidate binding partners can be identified by searching databases containing compounds along with information on their molecular structure. Such a search seeks compounds having structures that match the determined active site structure and that interact with the groups defining the active site. Such a search can be manual, but is preferably computer assisted. One program that allows for such analysis is Insight II having the Ludi module. Further, the Ludi/ACD module allows a user access to over 65,000 commercially available drug candidates (MDL's Available Chemicals Directory) and provides the ability to screen these compounds for interactions with the protein of interest.

Alternatively, these methods can be used to identify improved binding partners from an already known binding partner. The composition of the known binding partner can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Once candidate binding partners have been identified, desirably, they are analyzed in a functional assay. Further cycles of modeling and functional assays can be employed to more narrowly define the parameters needed in a binding partner. Each binding partner and its response in a functional assay can be recorded on a computer readable media and a database or library of binding partners and respective responses in a functional assay can be generated. These databases or libraries can be used by researchers to identify important differences between active and inactive molecules so that compound libraries are enriched for binding partners that have favorable characteristics. The section below describes several HMGB1 functional assays that can be used to characterize new HMGB1 family members and candidate binding partners.

HMGB1 Characterization Assays

The term "HMGB1 characterization assay" or "HMGB1 functional assay" or "functional assay" the results of which can be recorded as a value in a "HMGB1 functional profile", include assays that directly or indirectly evaluate the presence of an HMGB1 nucleic acid or protein in a cell and HMGB1 activity, ability to interact with another molecule, and/or modulate activity.

Some functional assays involve binding assays that utilize multimeric agents. One form of multimeric agent concerns a manufacture comprising an HMGB1, hybrid, binding partner, or fragment thereof disposed on a support. These multimeric agents provide the HMGB1, hybrid, binding partner, or fragment thereof in such a form or in such a way that a sufficient affinity is achieved. A multimeric agent having an HMGB1, hybrid, or binding partner or fragment thereof is obtained by joining the desired polypeptide to a macromolecular support. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An HMGB1, hybrid, or binding partner or fragment thereof can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the HMGB1, hybrid, or binding partner or fragment thereof by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, an HMGB1, hybrid, or binding partner or fragment thereof can be covalently bound to carriers including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the HMGB1, hybrid, or binding partner or fragment thereof. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Furthermore, in some embodiments, a liposome or lipid bilayer (natural or synthetic) is contemplated as a support and HMGB1, hybrids, or binding partners are attached to the membrane surface or are incorporated into the membrane by techniques in liposome engineering. By one approach, liposome multimeric supports comprise an HMGB1, hybrid, or binding partner that is exposed on the surface. A hydrophobic domain can be joined to the HMGB1, hybrid, or binding partner so as to facilitate the interaction with the membrane. Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and CHROMOSORB carrier (Johns-Manville Products, Denver Co.). Ligand conjugated CHROMOSORB carrier (Synsorb-Pk) has been tested in humans for the prevention of hemolytic-uremic syndrome and was reported as not presenting adverse reactions. (*Armstrong et al. J Infectious Diseases* 171:1042-1045 (1995), which is herein incorporated by reference in its entirety). For some embodiments, a "naked" carrier (i.e., lacking an attached binding partner) that has the capacity to attach an HMGB1 or binding partner in the body of a organism is administered. By this approach, a "prodrugtype" therapy is envisioned in which the naked carrier is administered separately from the HMGB1 or binding partner and, once both are in the body of the organism, the carrier and the HMGB1 or binding partner are assembled into a multimeric complex.

The insertion of linkers, such as linkers (e.g., "λ linkers" engineered to resemble the flexible regions of λ phage) of an appropriate length between the HMGB1, hybrid, or binding partner and the support are also contemplated so as to encourage greater flexibility of the HMGB1, hybrid, or binding partner and thereby overcome any steric hindrance that can be presented by the support. The determination of an appropriate length of linker that allows for an optimal cellular response or lack thereof, can be determined by screening the HMGB1, hybrids, or binding partners with varying linkers in the assays detailed in the present disclosure.

A composite support comprising more than one type of HMGB1, hybrid, or binding partner is also envisioned. A "composite support" can be a carrier, a resin, or any macromolecular structure used to attach or immobilize two or more different binding partners or HMGB1. In some embodiments, a liposome or lipid bilayer (natural or synthetic) is contemplated for use in constructing a composite support and HMGB1 or binding partners are attached to the membrane surface or are incorporated into the membrane using techniques in liposome engineering.

As above, the insertion of linkers, such as λ linkers, of an appropriate length between the HMGB1 or binding partner and the support is also contemplated so as to encourage greater flexibility in the molecule and thereby overcome any steric hindrance that can occur. The determination of an appropriate length of linker that allows for an optimal cellular response or lack thereof, can be determined by screening the HMGB1 or binding partners with varying linkers in the assays detailed in the present disclosure.

In other Embodiments, the multimeric and composite supports discussed above can have attached multimerized HMGB1, hybrids, or binding partners so as to create a "multimerized-multimeric support" and a "multimerized-composite support", respectively. A multimerized ligand can, for example, be obtained by coupling two or more binding partners in tandem using conventional techniques in molecular biology. The multimerized form of the HMGB1, hybrid, or binding partner can be advantageous for many applications because of the ability to obtain an agent with a higher affinity for HMGB1, for example. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized binding partner or HMGB1 or hybrid and the support can encourage greater flexibility and limit steric hindrance presented by the support. The determination of an appropriate length of linker can be determined by screening the HMGB1, hybrids, and binding partners with varying linkers in the assays detailed in this disclosure.

Thus, several approaches to identify agents that interact with an HMGB1, employ HMGB1 or a fragment thereof joined to a support. Once the support-bound HMGB1 is obtained, for example, candidate binding partners are contacted to the support-bound HMGB1 and an association is determined directly (e.g., by using labeled binding partner) or indirectly (e.g., by using a labeled antibody directed to the binding partner). Candidate binding partners are identified as binding partners by virtue of the association with the support-bound HMGB1. The properties of the binding partners are analyzed and derivatives are made using rational drug design and combinatorial chemistry. Candidate binding partners can be obtained from random chemical or peptide libraries but, preferably, are rationally selected. For example, monoclonal antibodies that bind to an HMGB1 can be created and the nucleic acids encoding the VH and VL domains of the antibodies can be sequenced. These sequences can then be used to synthesize peptides that bind to HMGB1. Further, peptidomimetics corresponding to these sequences can be created. These molecules can then be used as candidate binding partners.

Additionally, a cell based approach can be used characterize new HMGB1 family members or HMGB1 hybrids or to rapidly identify binding partners that interact with an HMGB1 and, thereby, modulate activity. Preferably, molecules identified in the support-bound HMGB1 assay described above are used in the cell based approach, however, randomly generated compounds can also be used.

Other HMGB1 characterization assays take advantage of techniques in molecular biology that are employed to discover protein:protein interactions. One method that detects protein-protein interactions in vivo, the two-hybrid system, is described in detail for illustration only and not by way of limitation. Other similar assays that can be adapted to identify binding partners include:

the two-hybrid systems (Field & Song, *Nature* 340:245-246 (1989); Chien et al., *Proc. Natl. Acad. Sci. USA* 88:9578-9582 (1991); and Young K H, *Biol. Reprod.* 58:302-311 (1998), all references herein expressly incorporated by reference);

reverse two-hybrid system (Leanna & Hannink, *Nucl. Acid Res.* 24:3341-3347 (1996), herein incorporated by reference);

repressed transactivator system (Sadowski et al., U.S. Pat. No. 5,885,779), herein incorporated by reference);

phage display (Lowman H B, *Annu. Rev. Biophys. Biomol. Struct.* 26:401-424 (1997), herein incorporated by reference); and GST/HIS pull down assays, mutant operators (Granger et al., WO 98/01879) and the like (See also Mathis G., *Clin. Chem.* 41:139-147 (1995); Lam K. S. *Anticancer Drug Res.*, 12:145-167 (1997); and Phizicky et al., *Microbiol. Rev.* 59:94-123 (1995), all references herein expressly incorporated by reference).

An adaptation of the system described by Chien et al., 1991, Proc. Natl. Acad. Sci. USA, 88:9578-9582, herein incorporated by reference), which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding an HMGB1 or fragment thereof, and the other plasmid consists of nucleotides encoding the transcription activator protein's activation domain fused to a cDNA encoding an unknown protein that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, HMGB1 can be used as the bait gene product. Total genomic or cDNA sequences are fused to the DNA encoding an activation domain. This library and a plasmid encoding a hybrid of a bait gene encoding the HMGB1 product fused to the DNA-binding domain are cotransformed into a yeast reporter strain, and the resulting transformants are screened for those that express the reporter gene. For example, and not by way of limitation, a bait gene sequence encoding an HMGB1 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait HMGB1 are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait HMGB1 gene-GAL4 fusion plasmid into a yeast strain which contains a lacZ gene driven by a promoter which contains GAL4 activation sequence. A cDNA encoded protein, fused to GAL4 transcriptional activation domain that interacts with bait HMGB1 gene product will reconstitute an active GAL4 protein and thereby drive expression of the lacZ gene. Colonies that express lacZ can be detected and the cDNA can then be purified from these strains, and used to produce and isolate the binding partner by techniques routinely practiced in the art.

Identification of Binding Agents

Further contemplated is the use of the polypeptides of the embodiments disclosed herein, or the polynucleotides encoding these polypeptides, to screen for molecules which modify the activities of the polypeptides of the embodiments disclosed herein. Such a method would include contacting the polypeptide of the embodiments disclosed herein with a selected compound(s) suspected of having antagonist or agonist activity, and assaying the activity of these polypeptides following binding.

Embodiments disclosed herein relate to screening therapeutic compounds by using the HMGB1 polypeptides described herein in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the embodiments disclosed herein.

Thus, the embodiments disclosed herein provide methods of screening for drugs or any other agents which affect activities mediated by HMGB1 polypeptides described herein. These methods comprise contacting such an agent with a polypeptide of the embodiments disclosed herein or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the embodiments disclosed herein.

Another technique for drug screening provides high throughput screening for compounds having suitable binding affinity to the polypeptides of the embodiments disclosed herein, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the embodiments disclosed herein and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This embodiments disclosed herein also contemplates the use of competitive drug screening assays in which neutralizing antibodies capable of binding HMGB1 polypeptides specifically compete with a test compound for binding to the polypeptides or fragments thereof. In this manner, the antibodies are used to detect the presence of any peptide which shares one or more antigenic epitopes with a polypeptide of the embodiments disclosed herein.

HMGB1 polypeptides, immunogenic fragments, or oligopeptides thereof can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the embodiments disclosed herein provides a method for screening or assessing a plurality of compounds for their specific binding affinity with a HMGB1 polypeptide, or a bindable peptide fragment, of this embodiments disclosed herein, comprising providing a plurality of compounds, combining the HMGB1 polypeptide, or a bindable peptide fragment, with each of a plurality of compounds for a time sufficient to allow binding under suitable conditions and detecting binding of the HMGB1 polypeptide or peptide to each of the plurality of test compounds, thereby identifying the compounds that specifically bind to the HMGB1 polypeptide or peptide.

Methods of identifying compounds that modulate the activity of the HMGB1 polypeptides are provided by the embodiments disclosed herein and comprise combining a potential or candidate compound or drug modulator of immunoglobulin biological activity with an HMGB1 polypeptide or peptide and measuring an effect of the candidate compound or drug modulator on the biological activity of the HMGB1 polypeptide or peptide. Such measurable effects include, for example, physical binding interaction.

Another method of identifying compounds that modulate the biological activity of the HMGB1 polypeptides of the embodiments disclosed herein comprises combining a potential or candidate compound or drug modulator with a host cell that expresses the HMGB1 polypeptide and measuring an effect of the candidate compound or drug modulator on the biological activity of the HMGB1 polypeptide. The host cell can also be capable of being induced to express the HMGB1 polypeptide, e.g., via inducible expression. Physiological effects of a given modulator candidate on the HMGB1 polypeptide can also be measured. Thus, cellular assays for particular immunoglobulin modulators may be either direct measurement or quantification of the physical biological activity of the HMGB1 polypeptide, or they may be measurement or quantification of a physiological effect. Such methods preferably employ a HMGB1 polypeptide as described herein, or an overexpressed recombinant HMGB1 polypeptide in suitable host cells containing an expression vector as described herein, wherein the HMGB1 polypeptide is expressed, overexpressed, or undergoes upregulated expression.

Another aspect of the embodiments disclosed herein relates to a method of screening for a compound that is capable of modulating the biological activity of a HMGB1 polypeptide, comprising providing a host cell containing an expression vector harboring a nucleic acid sequence encoding a HMGB1 polypeptide or fragment thereof determining the biological activity of the expressed HMGB1 polypeptide or fragment in the absence of a modulator compound; contacting the cell with the modulator compound and determining the biological activity of the expressed HMGB1 polypeptide or fragment in the presence of the modulator compound. In such a method, a difference between the activity of the HMGB1 polypeptide or fragment in the presence of the modulator compound and in the absence of the modulator compound indicates a modulating effect of the compound.

Chemical Libraries and Drug Screening

Any chemical compound can be employed as a potential modulator or ligand in the assays according to the embodiments disclosed herein. Compounds tested as immunoglobulin modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies can be used for the detection of modulators of HMGB1. Such high throughput screening methods can involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37:487-493; and Houghton et al., 1991, Nature, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90:6909-6913), vinylogous polypeptides (Hagihara et al., 1992, J. Amer. Chem. Soc., 114:6568), nonpeptidal peptidomimetics with glucose scaffolding (Hirschmann et al., 1992, J. Amer. Chem. Soc., 114:9217-9218), analogous organic synthesis of small compound libraries (Chen et al., 1994, J. Amer. Chem. Soc., 116:2661), oligocarbamates (Cho et al., 1993, Science, 261:1303), and/or peptidyl phosphonates (Campbell et al., 1994, J. Org. Chem., 59:658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14(3):309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; each of which is herein incorporated by reference in its entirety, and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

One embodiment provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

Various embodiments disclosed herein relate to screening and small molecule (e.g., drug) detection assays which involve the detection or identification of small molecules that can bind to a HMGB1 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

Any method known in the art for selecting and synthesizing small molecule libraries for screening is contemplated for use in various embodiments disclosed herein. Small molecules to be screened are advantageously collected in the form of a combinatorial library. For example, libraries of drug-like small molecules, such as beta-turn mimetic libraries and the like, may be purchased from for example CHEMDIV library, Pharmacopia or Combichem or synthesized and are described in Tietze and Lieb, Curr. Opin. Chem. Biol. 2:363-371, 1998; Carrell et al., Chem Biol. 2:171-183, 1995; U.S. Pat. Nos. 5,880,972, 6,087,186 and 6,184,223, the disclosures of which are hereby incorporated by reference.

Any of these libraries known in the art are suitable for screening, as are random libraries or individual compounds. In general, hydrophilic compounds are preferred because they are more easily soluble, more easily synthesized, and more easily compounded. Compounds having an average molecular weight of about 500 often are most useful, however, compounds outside this range, or even far outside this range also may be used. Generally, compounds having c logP scores of about 5.0 are preferred, however the methods are useful with all types of compounds. Simple filters like Lipinski's "rule of five" have predictive value and may be used to improve the quality of leads discovered by this inventive strategy by using only those small molecules which are bioavailable. See Lipinski et al., Adv. Drug Delivery Rev. 23:3-25, 1997.

Combinatorial chemistry small molecule "libraries" can be screened against drug targets. These collections provide an excellent source of novel, readily available leads. For example, CHEMDIV library uses more than 800 individual chemical cores, a unique Building Block Library, and proprietary chemistry in designing its Diversity Collections (small molecule libraries) to assemble 80,000-100,000 compounds a year. CombiLab lead library sets of 200-400 compounds also can be produced as a follow-up. In addition, CHEMDIV library's compounds are designed to ensure their similarity to drugs adjusted according to proprietary algorithms of "drug-likeness definitions" (group similarity and advanced neural net approaches), and a variety of intelligent instruments for ADME&T (Absorption, Distribution, Metabolism, Excretion and Toxicity) properties prediction, such as partition coefficient, solubility, dissociation coefficients, and acute toxicity.

Directed synthesis of new small molecule libraries can provide a variety of compounds structurally related to the initial lead compound which may be screened to choose optimal structures. Preferably, a library of compounds is selected that are predicted to be "drug-like" based on properties such as pKa, log P, size, hydrogen bonding and polarity. The inventive multi-step approach which yields high affinity peptides in the first step, and small molecules in a subsequent step reduces the number of artificial hits by eliminating the lower affinity small molecules that would be selected and have to be assayed in a normal high throughput screening method.

To purify a HMGB1 polypeptide or peptide to measure a biological binding or ligand binding activity, the source may be a whole cell lysate that can be prepared by successive freeze-thaw cycles (e.g., one to three) in the presence of standard protease inhibitors. The HMGB1 polypeptide may be partially or completely purified by standard protein purification methods, e.g., affinity chromatography using specific antibody described infra, or by ligands specific for an epitope tag engineered into the recombinant HMGB1 polypeptide molecule, also as described herein. Binding activity can then be measured as described.

Various embodiments relate to compounds that are identified according to the methods described herein, and which modulate or regulate the biological activity or physiology of HMGB1 polypeptides. It is contemplated that such modulatory compounds may be employed in treatment and therapeutic methods for treating a condition that is associated with the novel HMGB1 polypeptides by administering to a subject in need of such treatment a therapeutically effective amount of the compound identified by the methods described herein.

Screening HMGB1 Antagonists for Prevention or Treatment of Cancer

Several embodiments relate to screening HMGB1 antagonists for ability to prevent or treat cancer. Any of the HMGB1 antagonists described herein or identified with approaches, for example, as described above relating to identification of HMGB1 binding agents and drugs can be used in embodiments to screen whether such antagonists can prevent or treat cancer.

In various embodiments, any of the HMGB1 antagonists described herein or identified with approaches, for example, as described above relating to identification of HMGB1 binding agents and drugs can be used in embodiments to screen whether such antagonists can prevent or treat malignant mesothelioma (MM) in an in vivo model of MM.

In several embodiments, any of the HMGB1 antagonists described herein or identified with approaches, for example, as described above relating to identification of HMGB1 binding agents and drugs can be administered to a mouse before or after the mouse is injected with MM cells. The effect of the HMGB1 antagonist in preventing or treating mesothelioma can be screened by determining whether such antagonists prevent the MM cells from forming tumors in the mouse for a given amount of time post-administration, delay the onset of tumor formation, reduce the growth of tumors that form from the injected MM cells, and/or extend the survival of the mouse.

In various embodiments, any of the HMGB1 antagonists described herein or identified with approaches, for example, as described above relating to identification of HMGB1 binding agents and drugs can be used in embodiments to screen whether such antagonists can prevent or treat malignant mesothelioma (MM) in vitro. For example, any of the HMGB1 antagonists described herein or identified with approaches, for example, as described above relating to identification of HMGB1 binding agents and drugs can be incubated with MM cells in vitro and assayed for cytotoxic effect, ability to inhibit anchorage-independent growth, or ability to inhibit MM cell motility. Also, any of the HMGB1 antagonists described herein or identified with approaches, for example, as described above relating to identification of HMGB1 binding agents and drugs can be incubated with human mesothelial cells (HM) treated with asbestos to determine whether such antagonists can inhibit asbestos-induced transformation of the HM cells. Examples of protocols for the in vitro and in vivo screening methods include but are not limited to those described in detail below in the Examples section.

Administration and Pharmaceutical Forms

The HMGB1 antagonists can be administered in a variety of ways and pharmaceutical forms in the embodiments provided herein for preventing or treating cancer. As such, provided herein are several compositions drawn to pharmaceutical compositions comprising the HMGB1 antagonists described herein and a pharmaceutically acceptable carrier or diluent depending on the route and form of administration.

Examples of routes of administration that may be used include injection (subcutaneous, intravenous, parenterally, intraperitoneally, intrathecal), or oral routes. The pharmaceutical preparations may be given by forms suitable for each administration route. For example, these preparations can be administered in tablets or capsule form, by injection or orally. The injection can be bolus or can be continuous infusion. The HMGB1 antagonists can be administered alone, or in conjunction with either another agent or agents known in the art for treating cancer or with a pharmaceutically-acceptable carrier, or both.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN surfactant, polyethylene glycol (PEG).

The compositions may be in the "pharmaceutical form" of tablets, capsules, powders, granules, lozenges, liquid or gel preparations. Tablets and capsules for oral administration may be in a form suitable for unit dose presentation and may contain conventional excipients. Examples of these are: binding agents such as syrup, acacia, gelatin, sorbitol, tragacanth, and polyvinylpyrrolidone; fillers such as lactose, sugar, maize-starch, calcium phosphate, sorbitol or glycine; tableting lubricants, such as magnesium stearate, silicon dioxide, talc, polyethylene glycol or silica; disintegrants, such as potato starch; or acceptable wetting agents, such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

Solid dosage forms for oral administration include capsules, tablets, pills, powders, and granules. In such solid dosage forms, the HMGB1 antagonist can be admixed with at least one inert pharmaceutically acceptable carrier such as sucrose, lactose, or starch. Such dosage forms can also comprise, as is normal practice, additional substances other than inert diluents, for example, lubricating agents such as magnesium stearate. In the case of capsules, tablets, and pills, the dosage forms may also comprise buffering agents. Tablets and pills can additionally be prepared with enteric coatings known in the art.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

The HMGB1 antagonists described herein can also be administered parenterally. The phrases "parenteral administration" and "administered parenterally" as used herein includes, for example, modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. Parenteral administration can include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

For parenteral administration, the HMGB1 antagonists can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin Liposomes and nonaqueous vehicles such as fixed oils may also be used. The vehicle or lyophilized powder may contain additives that maintain isotonicity (for example, sodium chloride, mannitol) and chemical stability (for example, buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions described herein can be administered as a single dose or in multiple doses; administered either as individual therapeutic agents or in combination with other therapeutic agents; and combined with conventional therapies, which may be administered sequentially or simultaneously.

Dosages

The effective amount of any HMGB1 antagonist described herein sufficient to prevent or treat cancer can be administered in a dosage of about 1 μg/kg, 50 μg/kg, 100 μg/kg, 150 μg/kg, 200 μg/kg, 250 μg/kg, 300 μg/kg, 350 μg/kg, 400 μg/kg, 500 μg/kg, 550 μg/kg, 600 μg/kg, 700 μg/kg, 800 μg/kg, 900 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 75 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 425 mg/kg, 450 mg/kg, 475 mg/kg, 500 mg/kg, 750 mg/kg, 1000 mg/kg, or any number in between any two of the aforementioned dosages (mass of the HMGB1 antagonist (e.g. anti-HMGB1 antibody, anti-RAGE antibody, Box A polypeptide, anti-inflammatory compound)/mass of subject).

In another embodiment, the effective amount of any HMGB1 antagonist described herein sufficient to prevent or treat cancer can be administered as a fixed dosage irrespective of the subject's mass. For example, the effective amount of the HMGB1 antagonist can be a fixed dose of about 1 μg, 50 μg, 75 μg, 100 μg, 150 μg, 200 μg, 250 μg, 300 μg, 350 μg, 400 μg, 500 μg, 550 μg, 600 μg, 700 μg, 800 μg, 900 μg, 1 mg, 5 mg, 10 mg, 15 mg, 20 mg, 25 mg, 30 mg, 35 mg, 40 mg, 45 mg, 50 mg, 75 mg, 100 mg, 200 mg, 300 mg, 400 mg, 500 mg, 600 mg, 700 mg, 800 mg, 900 mg, 1000 mg, 1250 mg, 1500 mg, 1750 mg, 2000 mg, 2250 mg, 2500 mg, 2750 mg, 3000 mg, 3500 mg, 4000 mg, 4500 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500 mg, 10,000 mg, or any number in between any two of the aforementioned fixed doses.

While the present invention has been described in some detail for purposes of clarity and understanding, one skilled in the art will appreciate that various changes in form and detail can be made without departing from the true scope of the invention.

EXAMPLES

Having generally described embodiments drawn to methods of preventing or treating cancer, such as mesothelioma, in a subject including administering a HMGB1 antagonist to the subject, a further understanding can be obtained by reference to certain specific examples which are provided herein for purposes of illustration only, and are not intended to be limiting.

Example 1

HMGB1 and RAGE are Both Upregulated in MM Cells

The expression of HMGB1 and its receptors RAGE, TLR2 and TLR4 in a panel of 8 MM cell lines and 8 distinct primary HM cultures were investigated. Primary human mesothelial cells (HM) were obtained from pleural effusions of eight different patients, pathologically diagnosed free of malignancy at the Queen's Medical Center, Honolulu, Hi. HM were characterized by calretinin, pancytokeratin, and carcinoembryonic antigen (CEA) immunostaining, as previously described (Bocchetta M, et al., "Human mesothelial cells are unusually susceptible to simian virus 40-mediated transformation and asbestos cocarcinogenicity," *Proc Natl Acad Sci USA*. 2000; 97:10214-10219), which is herein incorporated by reference in its entirety. HM were cultured in Dulbecco's Modified Eagle Medium (DMEM) (Mediatech Inc., Manassas, Va.) containing 20% fetal bovine serum (FBS) (Gibco, Carlsbad, Calif.) and penicillin-streptomycin (100 units/ml penicillin G and 100 μg/ml streptomycin sulfate) (GIBCO), and were used between second and fifth passages. THP-1 human monocytes (ATCC, Manassas, Va.) were differentiated into macrophages by phorbol 12-myristate 13-acetate (TPA). The pleural malignant mesothelioma (MM) cell lines were established from surgically resected human MM specimens and used comparatively in our studies. REN cells were provided by Dr. Steven Albelda (University of Pennsylvania, Philadelphia, Pa.), while all other cell lines used in this study were provided by Dr. Harvey I. Pass (NYU School of Medicine, New York, N.Y.). MM cells were maintained in DMEM containing 10% FBS. All cells were cultured at 37° C. in a humidified atmosphere with 5% $CO_2$ and grown to approximately 80-90% confluency. REN/luc luminescent cells were derived from REN cells that were transduced with the lentiviral vector pRRL.sin.PPT.CMV expressing luciferase.

Quantitative real-time PCR (qRT-PCR) revealed that in 7 out of 8 MM cell lines the amounts of HMGB1 transcripts were significantly higher compared to HM. Briefly, total RNA from MM and HM cells was isolated using RNEASY kit (Qiagen, Valencia, Calif.) and treated with RNase-free DNase. For each sample, 3 μg of total RNA was reverse transcribed by using the First-Strand cDNA synthesis kit (Ferment as, Canada). β-actin housekeeping gene was used as the internal control for normalization. PCR amplifications for HMGB1, RAGE, TLR2, TLR4 and β-actin were performed in triplicates, by standard procedures, in 25 μl total reaction volumes using the SYBR dye green master PCR mix (Applied Biosystems, Carlsbad, Calif.) with the GeneAmp 5700 sequence detection system (PerkinElmer-Applied Biosystems). The following primers from the QUANTITECT kit Primer Assay method (Qiagen) were used: Hs_AGER_1_SG (QT00000119), Hs_HMGB1_1_SG (QT01002190), Hs_TLR4_2_SG (QT01670123), and Hs_TLR2_1_SG (200) (QT00236131). Amplifications were performed in triplicates and assayed twice. A large degree of variability was observed: PPM-Ada and PPM-Mill cells expressed relatively low levels of HMGB1 transcripts, while in REN and PPM-Phi cells the amount of HMGB1 transcripts exceeded by 6 and 20 times those found in primary HM cells (FIG. 1A).

HMGB1 protein expression and compartmentalization was evaluated by Western blotting by cell fractionation. Briefly, MM and HM cells were lysed and the cytoplasmic and nuclear fractions separated using the protein extraction kit from Active Motif (Carlsbad, Calif.), according to the manufacturer's instructions. Protein concentrations were determined using the BCA method (Thermo Scientific, Fremont, Calif.) and 50 μg of protein lysate from each sample were separated on NUPAGE gel Novex 4-12% Bis-Tris mini gels (Invitrogen, Carlsbad, Calif.) and transferred to HYBOND membrane-C Extra nitrocellulose membranes (Amersham Biosciences, UK). The membranes were blocked in Tris-buffered saline containing 0.05% TWEEN surfactant 20 (TBST) and 5% skim milk at RT for 2 hours; then probed with the primary antibody at 4° C. overnight; mouse monoclonal anti-HMGB1 (1:1000), rabbit polyclonal anti-RAGE (1:1000), mouse monoclonal anti-TLR2 (1:250) and goat polyclonal anti-TLR4 (1:250) were all from Abcam. Anti-a-Tubulin (1:5000; Calbiochem, San Diego, Calif.) and anti-Lamin B (1:1000; Abcam) were used as loading controls for the cytoplasmic and nuclear fractions, respectively. After probing with the primary antibodies, the membranes were washed four times with TBST and incubated with the appropriate horseradish peroxidase-conjugated secondary antibody (Pierce, Rockford, Ill.) at RT for 1 hour. The signal was detected by enhanced chemiluminescence (Pierce). Experiments were performed three times.

Figure 1B:
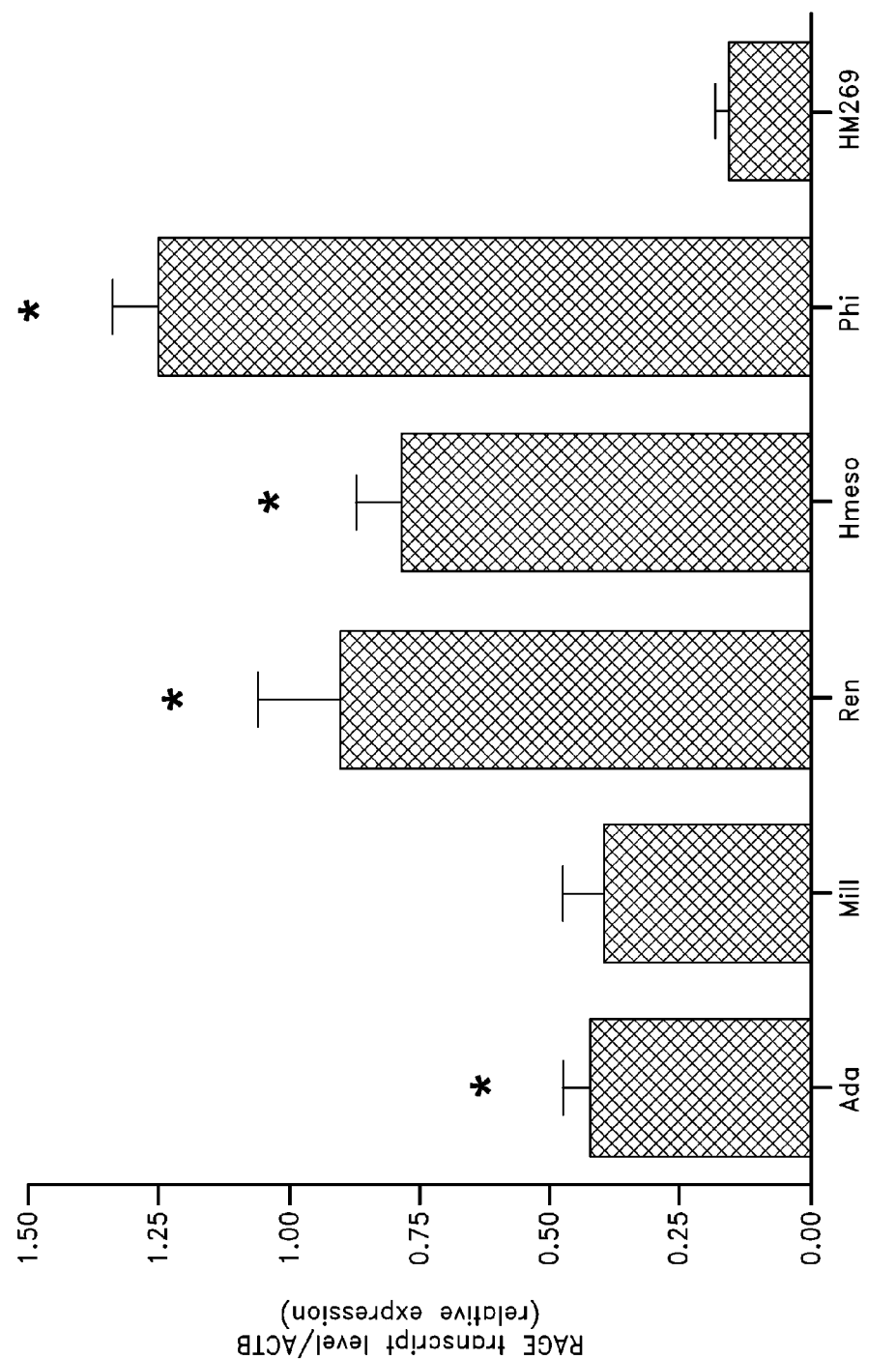
FIG. 1B is a graph showing qPCR measurements of RAGE mRNA transcript levels.
Figure 1C:
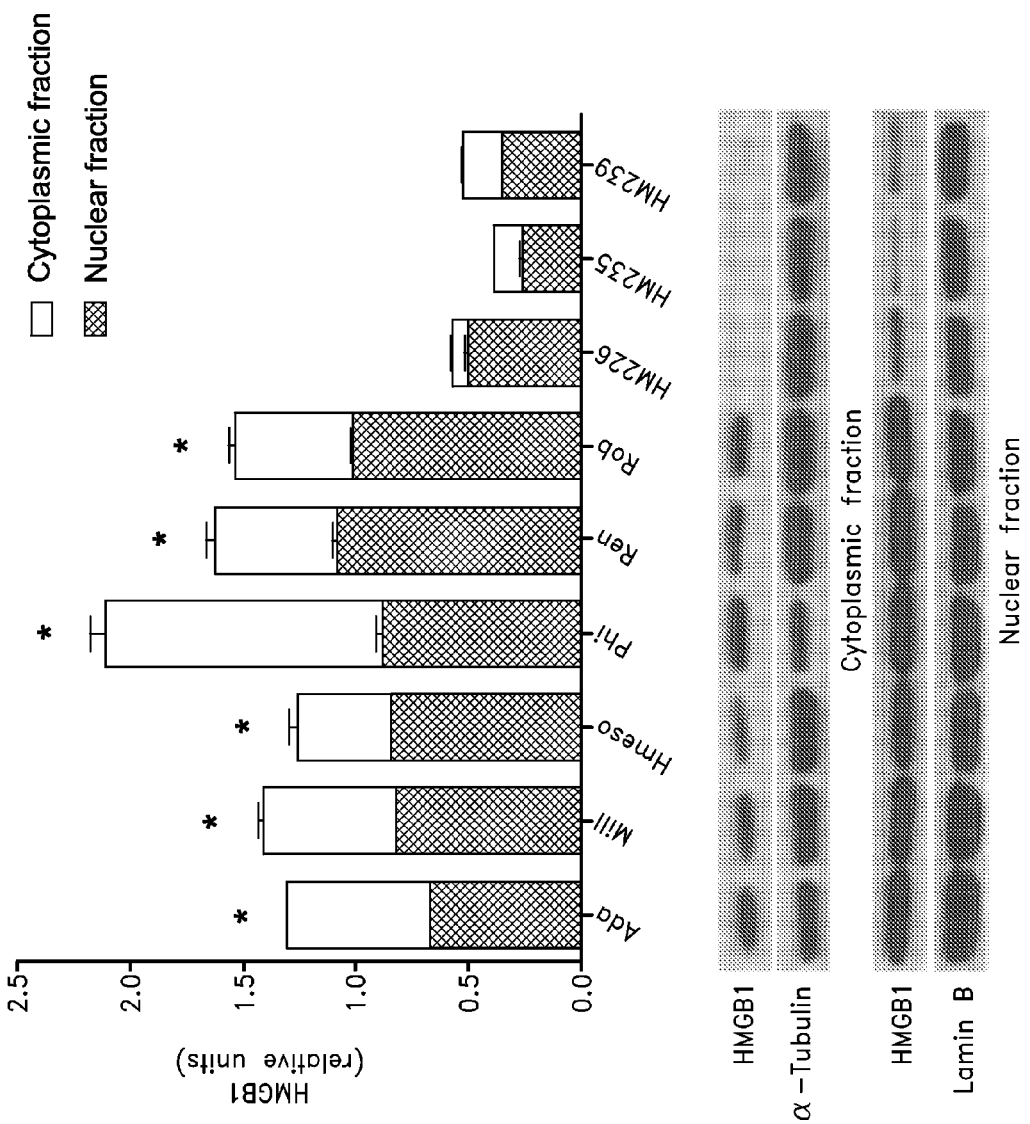
FIG. 1C is a Western Blot and graph comparing levels of HMGB1 in normal human mesothelial (HM) cells and MM cells.
Figure 1D:
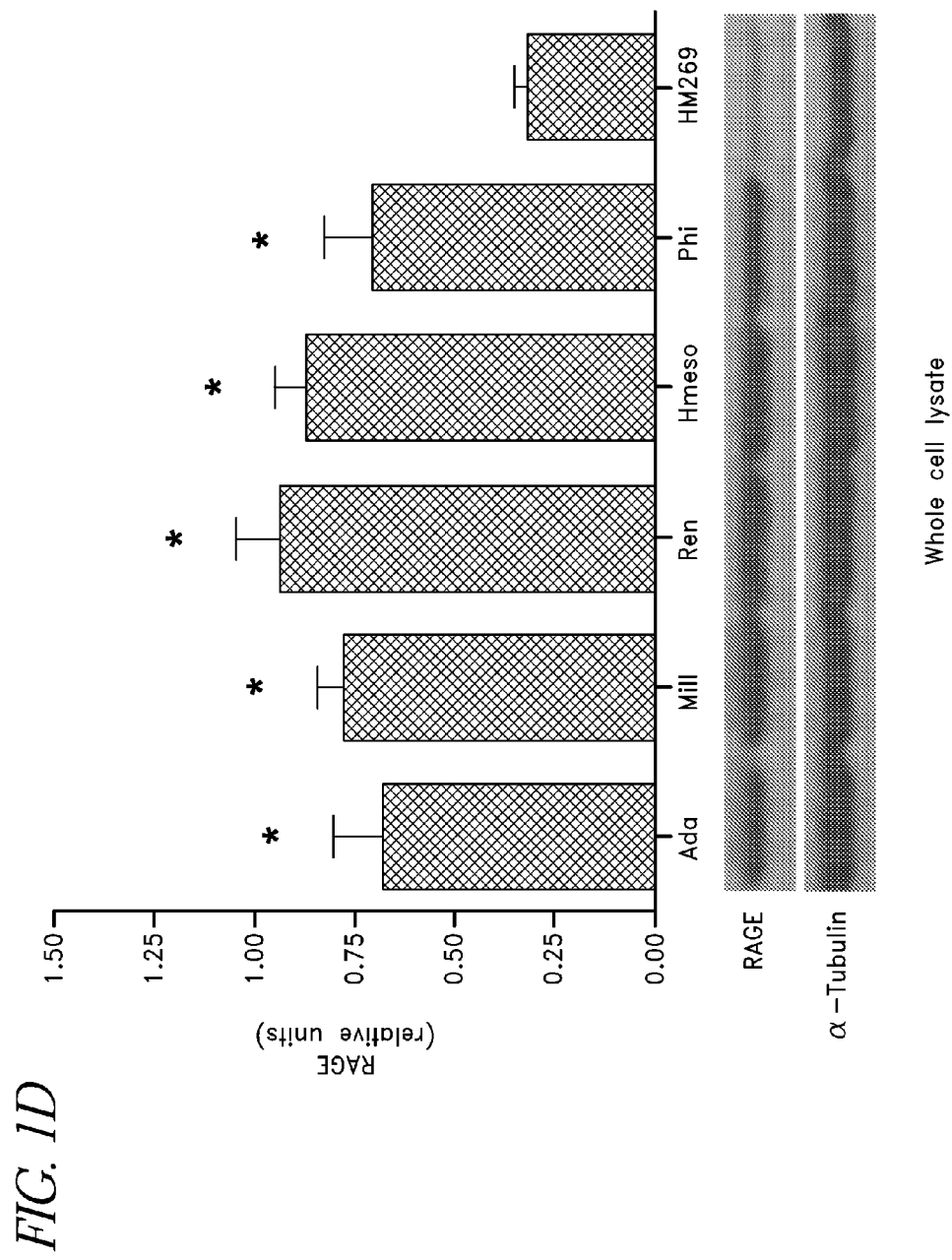
FIG. 1D is a Western Blot and graph comparing levels of RAGE in normal human mesothelial (HM) cells and MM cells.

In HM, HMGB1 was almost exclusively detected in the nuclear fraction; instead, MM cells contained high amounts of HMGB1 in both the nucleus and the cytoplasm (FIG. 1C). The results were confirmed by immunostaining: MM cells (PPM-Gor, PPM-Phi, and REN) had both nuclear and cytoplasmic HMGB1 staining, while HM cells had exclusively nuclear staining (FIG. 1E).

Figure 1F:
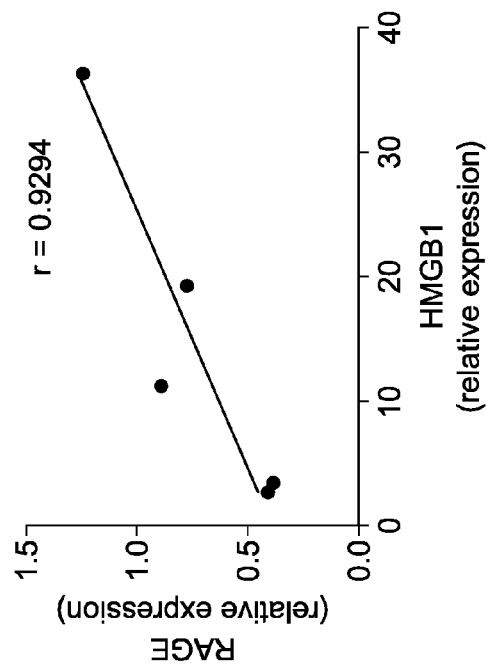
FIG. 1F is a graph showing positive correlation between HMGB1 and RAGE transcript levels in five different MM cell lines tested (r=0.93, P=0.022).
Figure 1E:
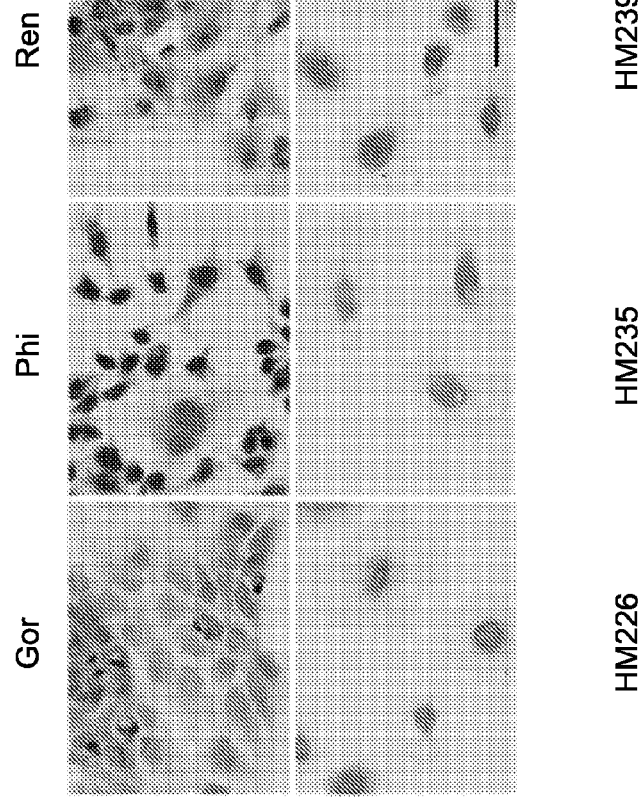
FIG. 1E is a panel of immunocytochemistry images showing a comparison of HMGB1 protein in HM cells and MM cells.
Figure 1G:
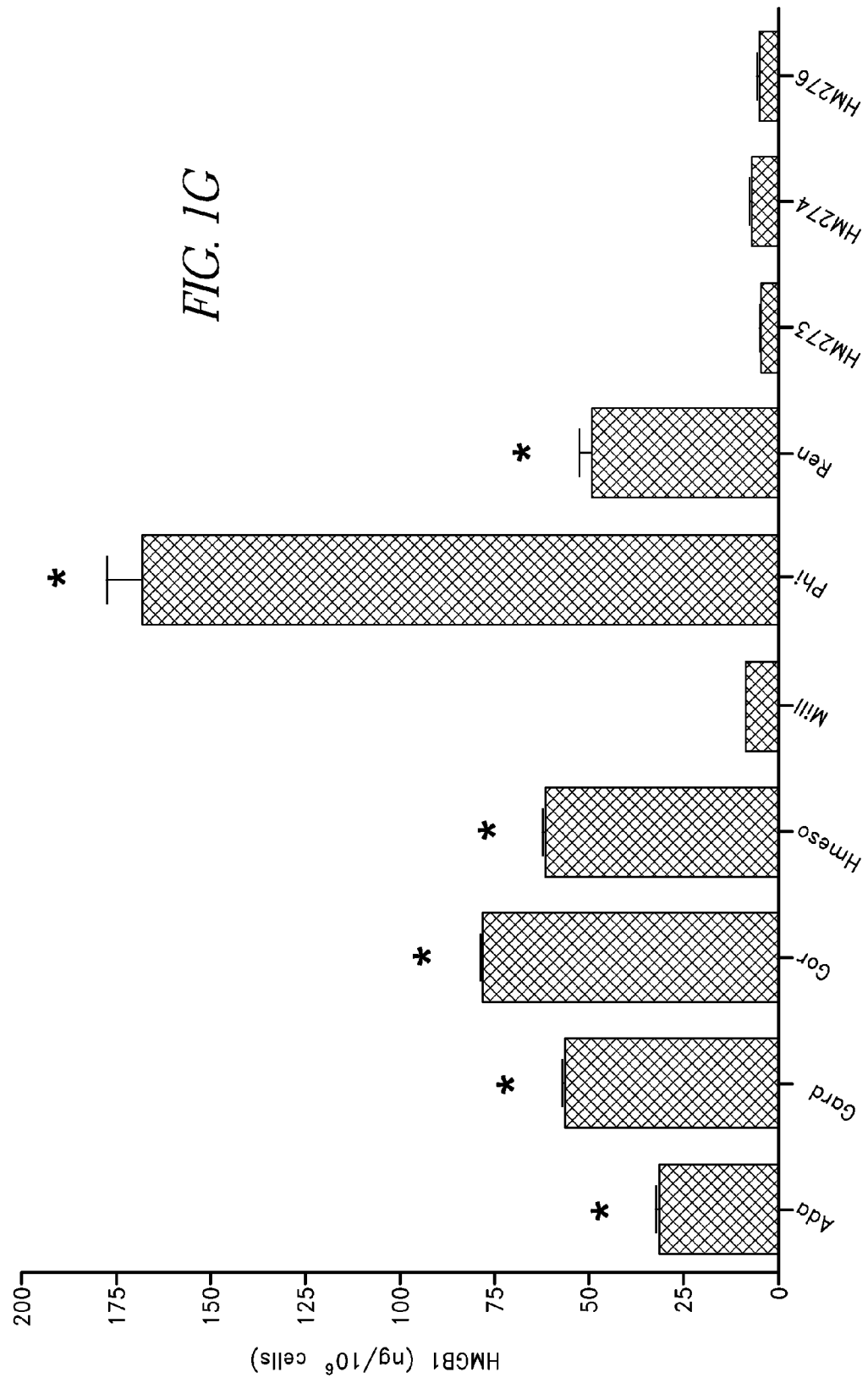
FIG. 1G is a graph showing the amount of HMGB1 released by in vitro cell cultures measured by ELISA.
Figure 2A:
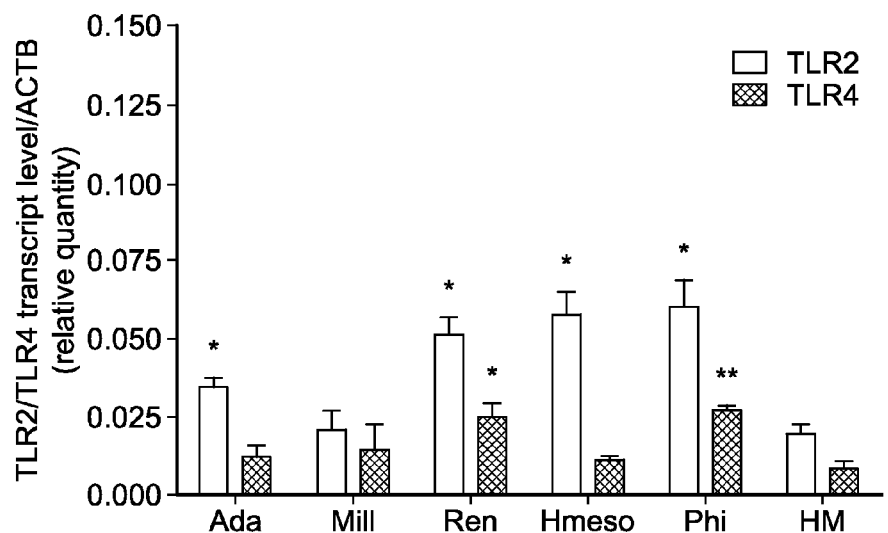
FIG. 2A is a graph showing qPCR measurements of TLR2 and TLR4 mRNA transcript levels in HM cells and MM cells.
Figure 2B:
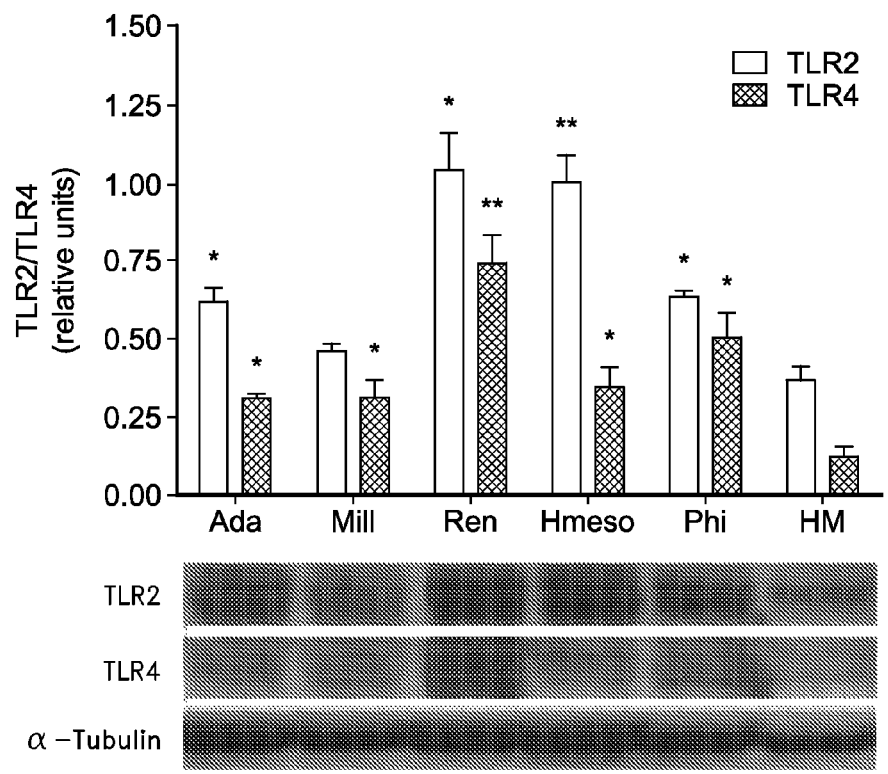
FIG. 2B is a Western Blot and graph comparing levels of TLR2 and TLR4 in HM cells and MM cells.

The amounts of RAGE transcripts paralleled the amounts of HMGB1 mRNA in the MM cell lines (FIG. 1F). Cells with abundant HMGB1 transcripts (PPM-Phi, REN, and PPM-Hmeso) had high amounts of RAGE transcripts, while cells with little HMGB1 mRNA (PPM-Ada and PPM-Mill) had low levels of RAGE mRNA (FIG. 1B). TLR2 and TLR4 transcript expression was also higher in MM than in HM cells, although the overall levels were lower than that of RAGE (FIG. 2A). The expression levels detected by qRT-PCR were confirmed at the protein level by Western blot analyses (FIG. 1D and FIG. 2B). In summary, the results indicate that most MM cell lines expressed high levels of HMGB1 and of its main receptors RAGE, TLR2 and TLR4.

Example 2

HMGB1 Inhibitors Hinder Asbestos-Induced HM Transformation

In vivo, macrophages are recruited to the sites of asbestos deposition. In order to mimic the cross-talk between HM and macrophages, a co-culture system was developed in which HM cells are exposed to crocidolite asbestos fibers (obtained from the Union Internationale Contre le Cancer (Geneva, Switzerland) and processed as previously described (Yang H, et al., "TNF-α inhibits asbestos-induced cytotoxicity via a NF-κB-dependent pathway, a possible mechanism for asbestos-induced oncogenesis. *Proc Natl Acad Sci USA.* 2006; 103(27):10397-10402)) in the presence of macrophages (Yang H, et al., "Programmed necrosis induced by asbestos in human mesothelial cells causes high-mobility group box 1 protein release and resultant inflammation," *Proc Natl Acad Sci USA.* 2010; 107(28):12611-12616), each of which is herein incorporated by reference in its entirety.

Primary HM cells were seeded in 6-well plates and were co-cultured with macrophages differentiated from monocytic THP-1 cells. Macrophages were cultured in separate inserts (BD Falcon, Bedford, Mass.) separated by membranes with 0.4 µm pores and allowing the free flux of cytokines between the two types of cells. Crocidolite asbestos (5 µg/cm$^2$) was added once to the co-culture, and after 48 hours asbestos-containing medium was replaced with fresh medium. HMGB1 antagonists BoxA (100 ng/ml) or monoclonal anti-HMGB1 (1 µg/ml), were added twice a week together with freshly differentiated macrophages for 8 weeks. HM cells were checked daily for signs of morphological transformation. The number and size of foci formed in each treatment were recorded at the end of the experiment. In this co-culture system, HM became transformed and formed tridimensional foci 1-2 months after asbestos exposure.

Figure 3A:
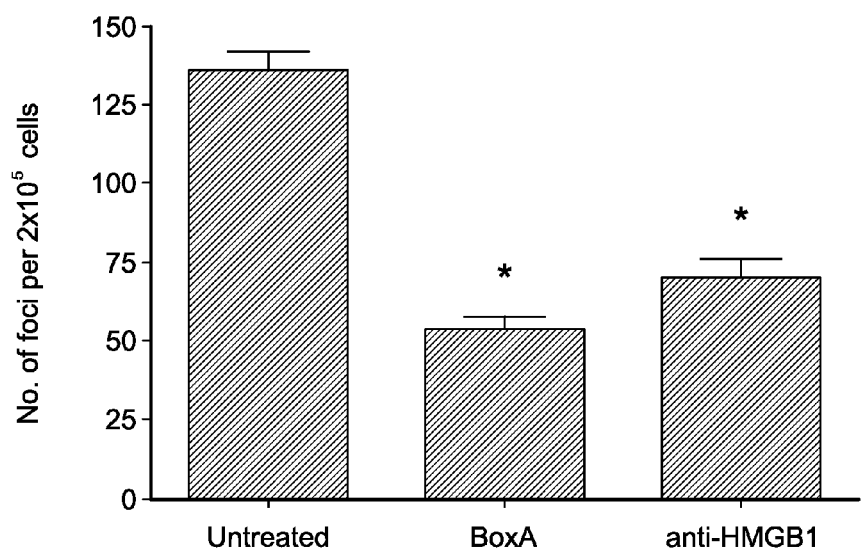
FIG. 3A is a graph showing the number of foci formed in HM/macrophage co-cultured, exposed to asbestos, and treated with BoxA or anti-HMGB1 antibody.
Figure 3B:
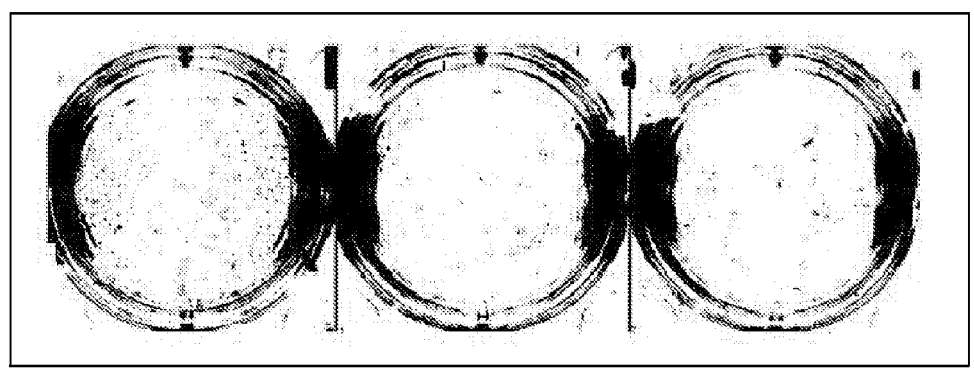
FIG. 3B shows foci formation under different treatments.
Figure 4:
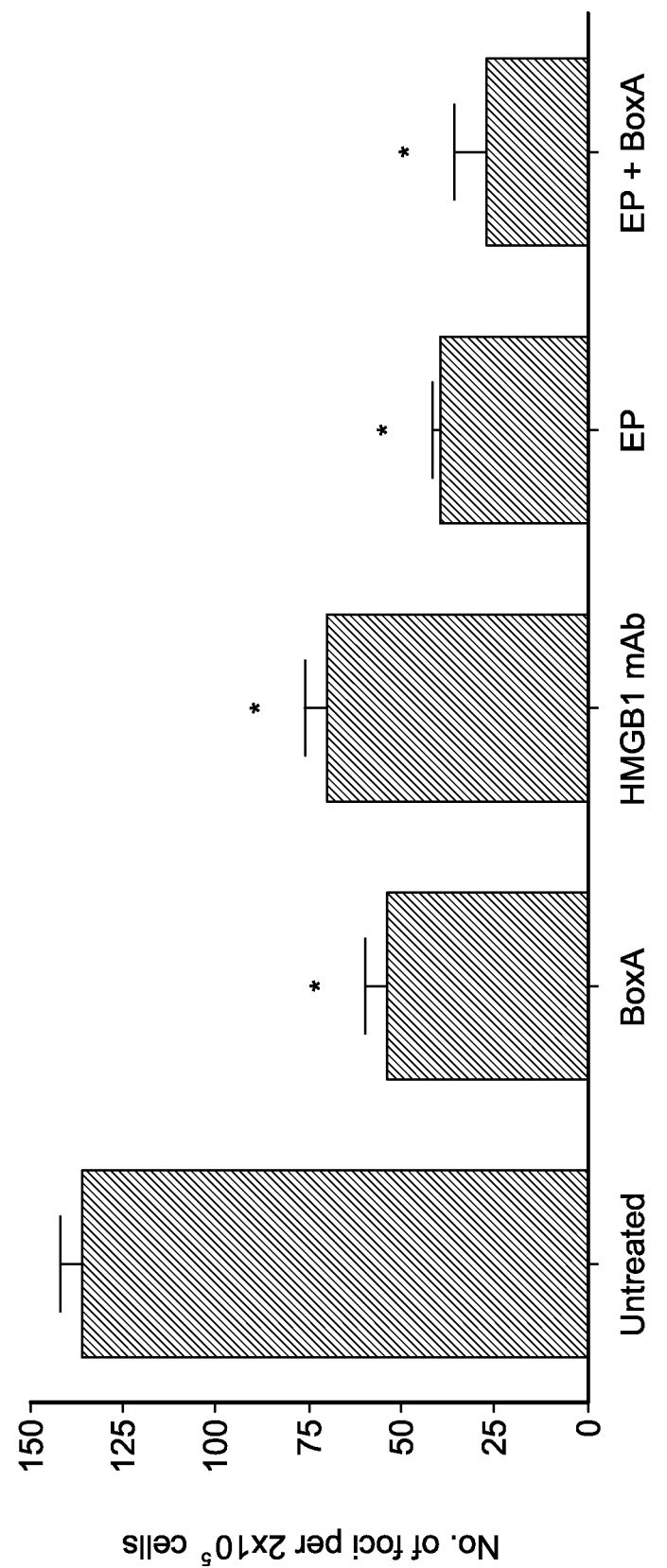
FIG. 4 is a graph showing HMGB1 inhibitors hinder asbestos-induced HM transformation.

To test the role of HMGB1 in the initial transformation of HM, two different HMGB1 inhibitors were used: BoxA (obtained from HMGBiotech (Milan, Italy)), a truncated form of HMGB1 comprising its first DNA-binding domain, which acts as a competitive antagonist (Sitia G, Iannacone M, Müller S, Bianchi M E and Guidotti L G (2007), "Treatment with HMGB1 inhibitors diminishes CTL-induced liver disease in HBV transgenic mice," *J Leukoc Biol* 81: 100-7), which is herein incorporated by reference in its entirety, and an anti-HMGB1 neutralizing monoclonal antibody (010910 obtained from DiaPro Diagnostics (Milan, Italy). The number of foci (mean±SEM) formed in the co-cultures treated with either BoxA (53.5±6.4) or anti-HMGB1 (70.0±9.9) was significantly lower than in the untreated co-cultures (136.5±7.8; FIG. 3). Similarly, the number of foci formed in the co-cultures treated with ethyl pyruvate (EP) or ethyl pyruvate plus BoxA (EP+BoxA) was significantly lower than in the untreated co-cultures (FIG. 4). Moreover, a two-week delay in the initial development of foci for the HMGB1-neutralized co-cultures, compared to the control was observed. In summary, HMGB1 inhibition reduced the rate and the amount of asbestos-induced HM transformation.

Example 3

HMGB1 is Mitogenic and Induces Migration of MM Cells

Figure 5A:
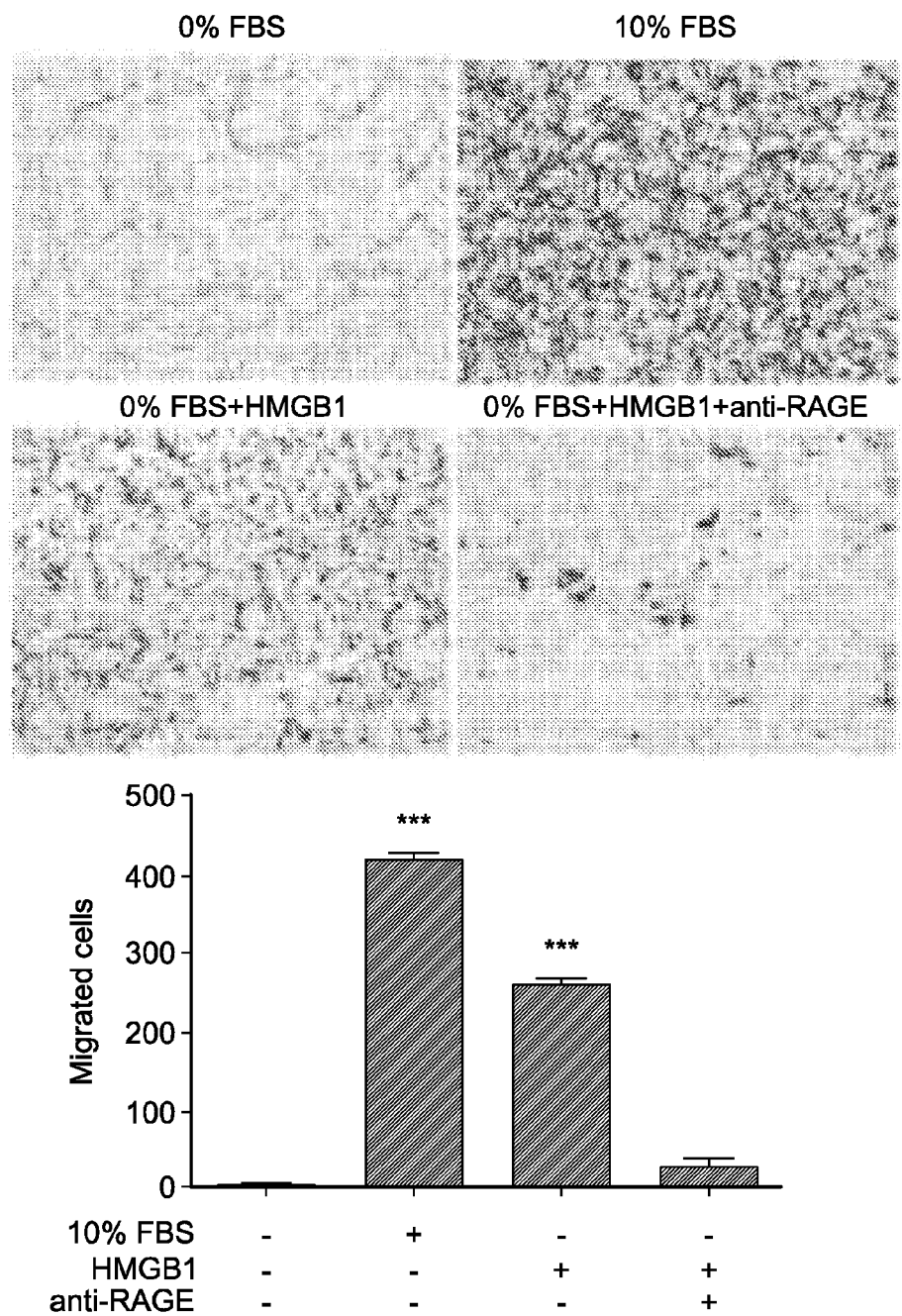
FIGS. 5A-B show the effect of exogenous recombinant HMGB1 on REN and PPM-Mill cells, respectively, in TRANSWELL migration assays.
Figure 5B:
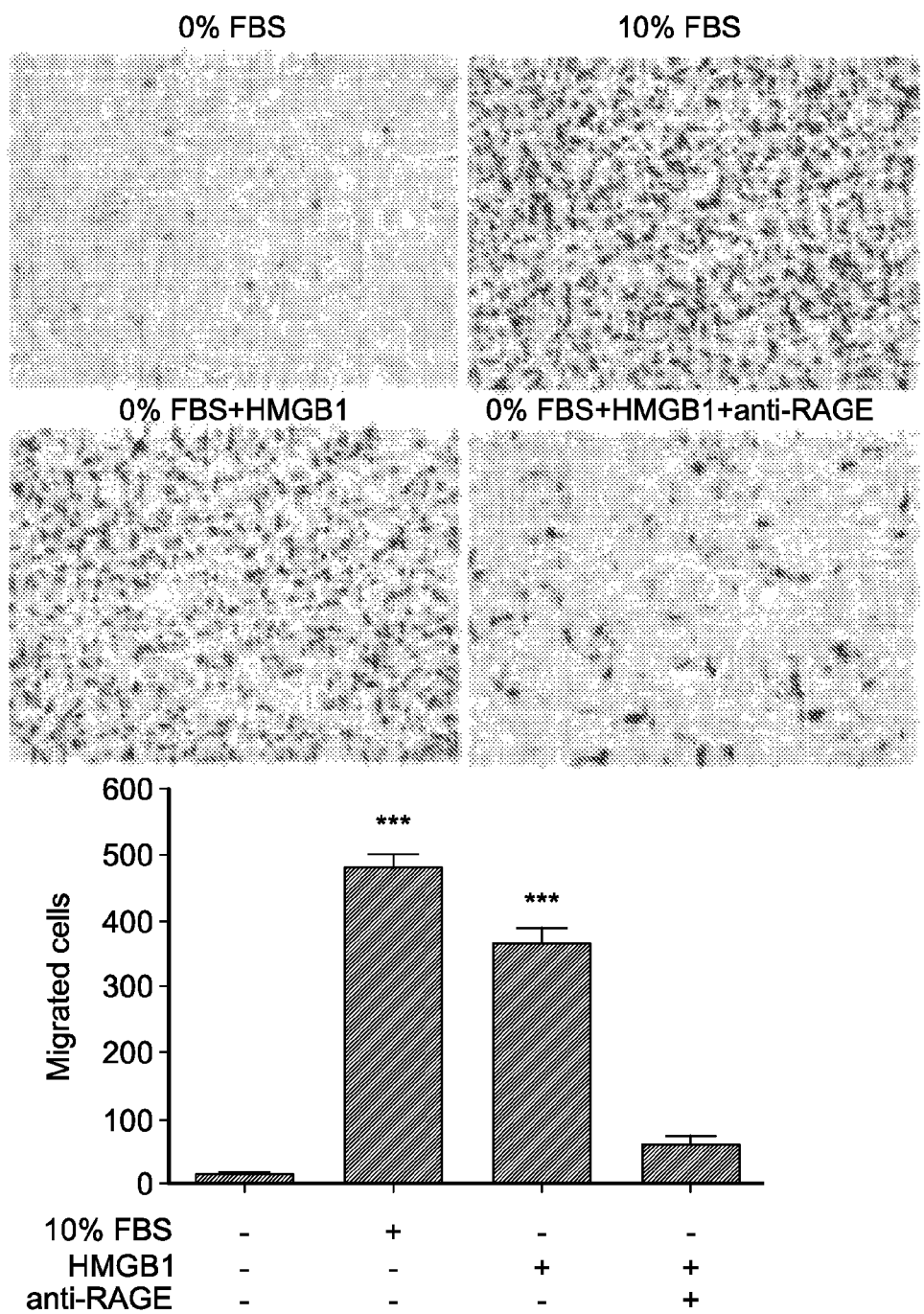
Figure 6A:
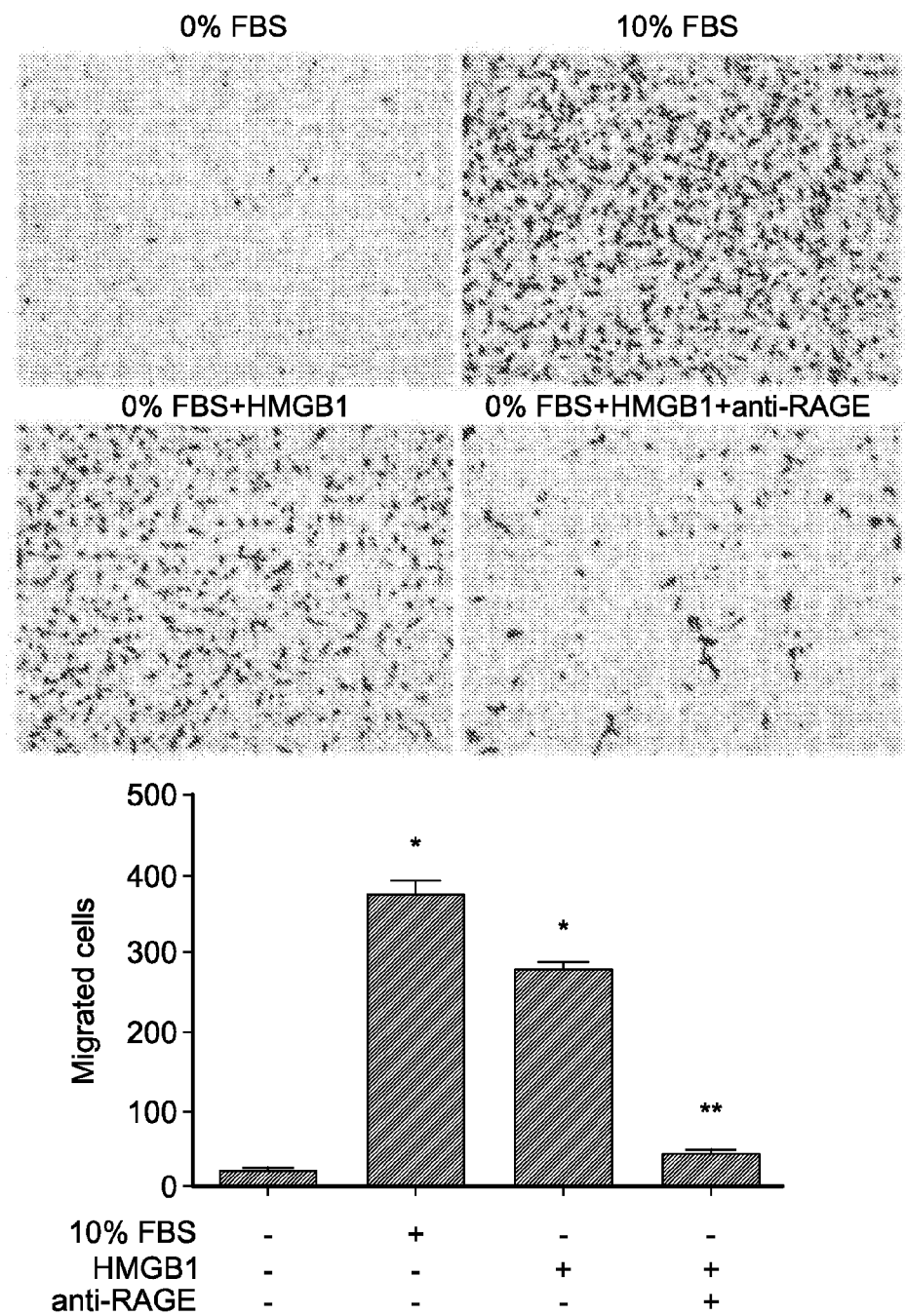
FIG. 6A shows the effect of exogenous recombinant HMGB1 on PPM-Phi cells in a TRANSWELL migration assay.

A chemoattractant assay toward purified recombinant human HMGB1 (100 ng/ml) (HM-114 obtained from HMG-Biotech) or 10% FBS (positive control) on 3 MM cell lines (REN, PPM-Mill and PPM-Phi) was conducted. All 3 MM cell lines migrated to the bottom chamber in the TRANSWELL system (FIGS. 5A and 5B; FIG. 6A). Anti-Rage monoclonal antibody (AF1145 obtained from R&D Systems (Minneapolis, Minn.)) abrogated the chemotactic activity of HMGB1.

Next, the mitogenic activity of recombinant HMGB1 on MM cells was evaluated. Briefly, MM cells ($4 \times 10^4$) were cultured in DMEM plus 1% FBS with or without purified recombinant HMGB1 (100 ng/ml) up to 96 hours and counted every 24 hours using a hemocytometer. Experiments were done in triplicate and performed three times.

Figure 5C:
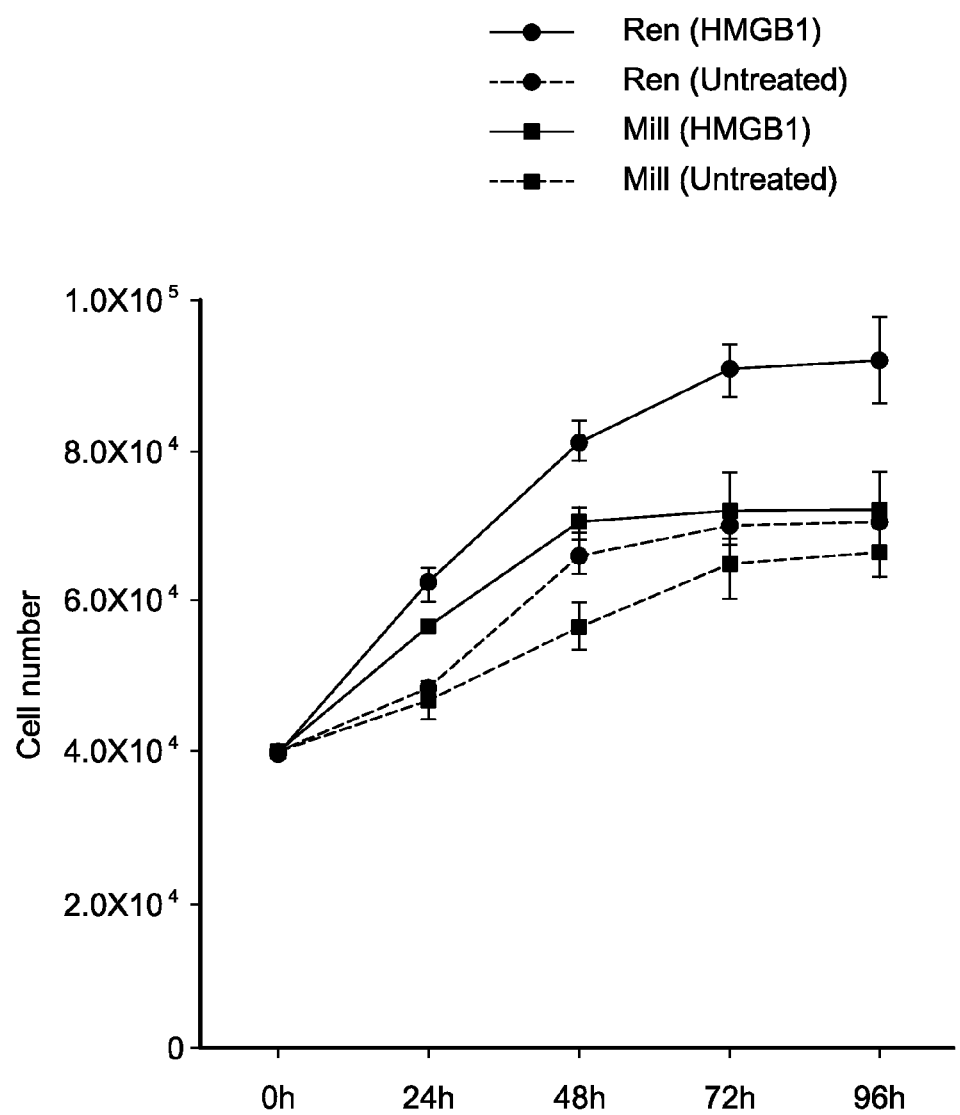
FIG. 5C is a graph of a cell proliferation assay showing that recombinant HMGB1 has mitogenic activity on MM cells.
Figure 6B:
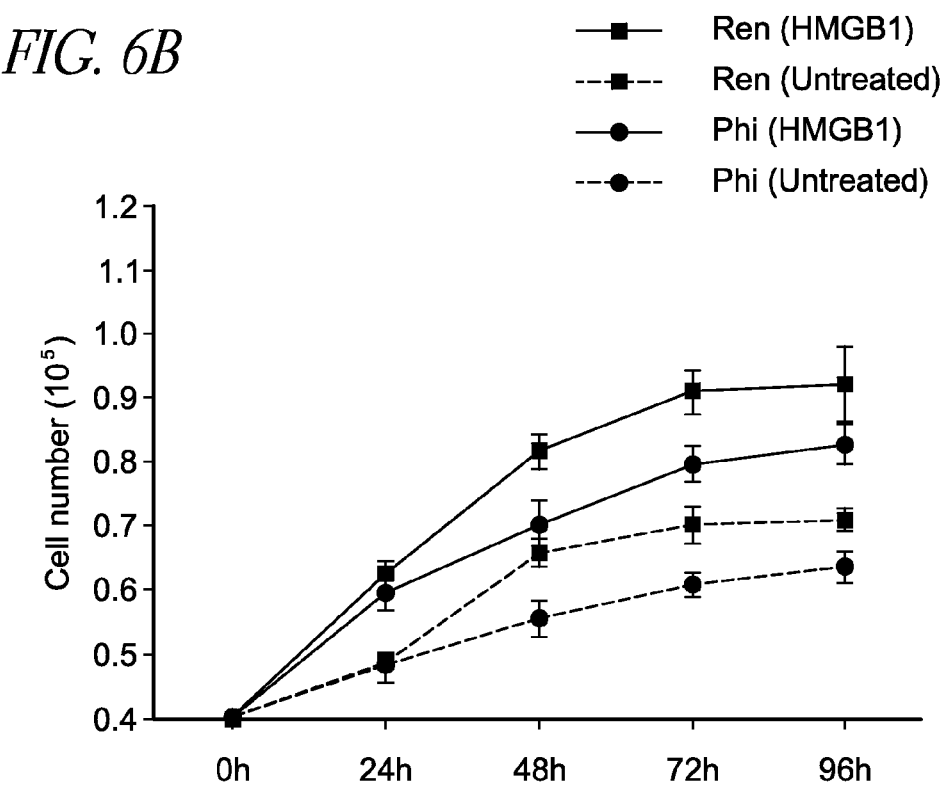
FIG. 6B a graph of a cell proliferation assay showing that recombinant HMGB1 induces cell proliferation in PPM-Phi cells.
Figure 6C:
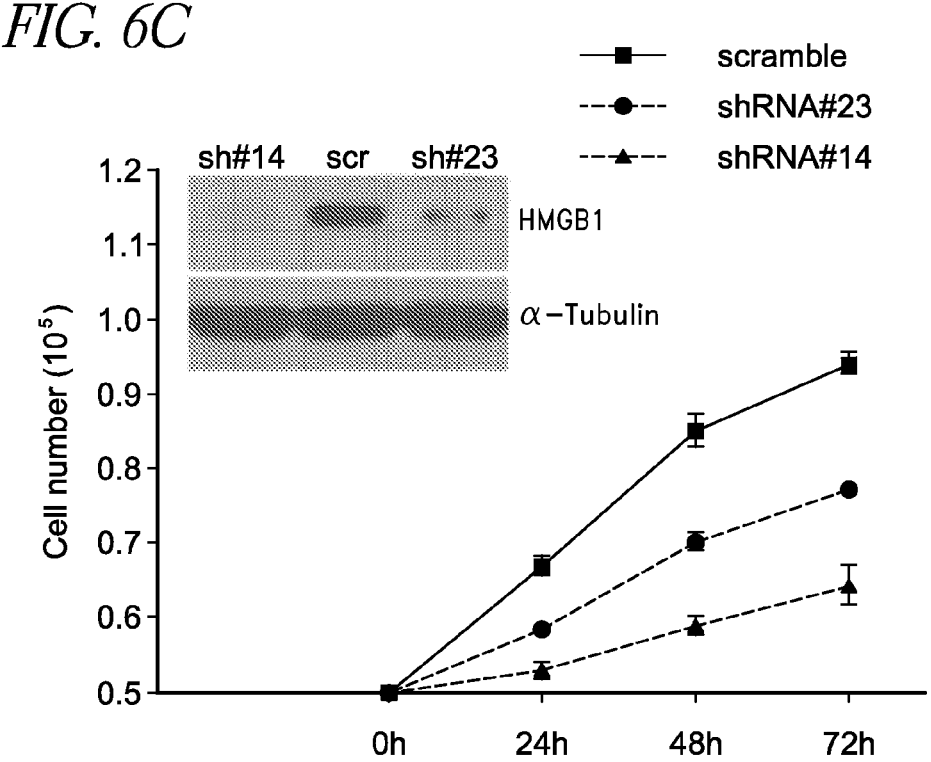
FIG. 6C depicts the effect of HMGB1 knock-down on cell proliferation using HMGB1 shRNA.

Exogenous recombinant HMGB1 significantly increased the cell proliferation rate of high HMGB1-secreting MM cells (REN and PPM-Phi), but had a less pronounced effect on the low HMGB1-secreting PPM-Mill cells (FIG. 5C; FIG. 6B). These experiments indicate that MM cells respond to HMGB1 by migration and proliferation.

Additionally, high-HMGB1 producing REN cells were transfected with HMGB1-specific shRNA (HuSH shRNA Plasmid Panels (29-mer), Origene). Experiments were performed according to the manufacturer's protocol. Briefly, 3×105 REN cells were plated into each well of a 6-well plate. TURBOFECTIN solution (3.0 µl) (Origene) and shRNA expression plasmid DNA (1.0 µg) (HMGB1-specific shRNAs and scrambled noneffective shRNA) were added to serum-free media (100 µl) and the mixture added to the cells in the 6-well plate. Cells were incubated at 37° C. with the same medium until the cells were ready to be passaged. Transfected cells were then passaged into a new plate containing fresh media supplemented with 1.0 µg/ml puromycin for stable transfection. Clonal population was selected by transferring a well-isolated single clump of cells into a well of a 24-well plate. Different clones were kept under puromycin selection and checked for HMGB1 knockdown by Western blotting. Two different clones carrying different HMGB1-specific shRNA constructs were used for cell proliferation. down-regulation of HMGB1 with two different gene-specific shRNA constructs significantly inhibited cell proliferation of REN cells compared to cells transfected with a scrambled control non-effective shRNA. FIG.

6C shows that HMGB1 expression was knocked-down by transfection of genespecific shRNA in REN cells, which are high HMGB1-producers. Down-regulation of HMGB1 with two different shRNA constructs significantly inhibited cell proliferation compared to REN cells transfected with a scrambled control non-effective shRNA. P<0.05; shRNA#14 and #23 versus scrambled shRNA. In all panels, error bars represent SEM.

Next TRANSWELL migration assays were performed to verify whether the endogenous HMGB1 secreted by MM cells has bioactivity. Briefly, the in vitro cell migration assays were performed using the Costar TRANSWELL permeable polycarbonate support (8.0 µm pores) in 24-well plates (Corning Inc., Corning, N.Y.). In the upper compartment, MM cells ($1 \times 10^5$) were suspended in 200 µl of serum-free medium. The lower compartment contained DMEM with no serum (negative control) or DMEM plus 10% FBS (positive control). To check for the chemotactic property of HMGB1, DMEM 10% FBS was substituted for either purified recombinant HMGB1 (100 ng/ml) or concentrated cell culture medium (200 µl) from REN or PPM-Mill cells. The cells were allowed to migrate into the lower compartment for 48 hours, then cells of the upper surface of the membrane were removed by a cotton swab, and the cells on the lower surface were stained using the HEMA 3 Staining Kit (Millipore, Billerica, Mass.). The migrated cells were counted from three random fields using the ImageJ software. Experiments were done in duplicate and performed three times.

Figure 5D:
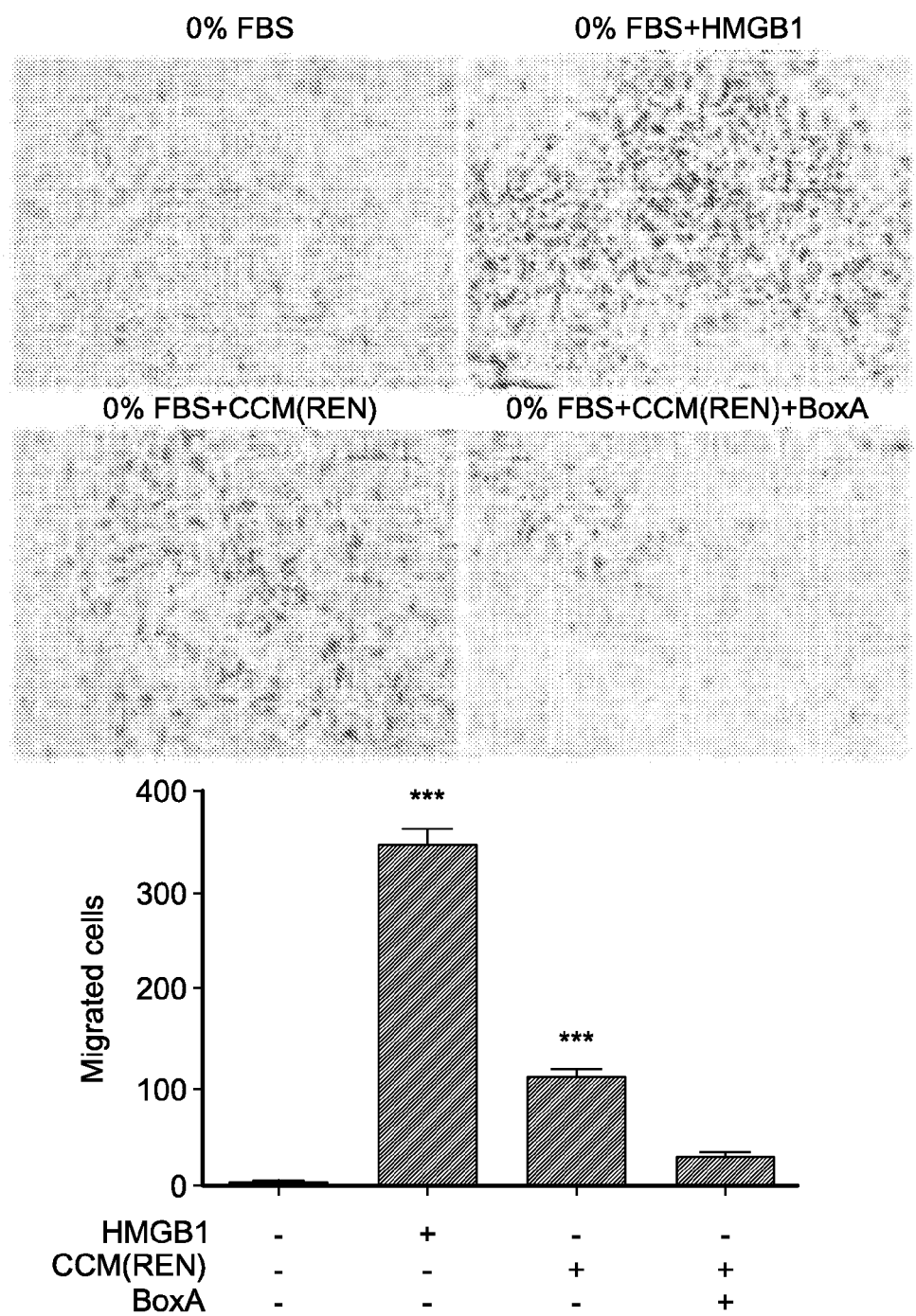
FIGS. 5D-E show the effect of conditioned concentrated media from REN cells and PPMMill cells, respectively, in TRANSWELL migration assays.
Figure 5E:
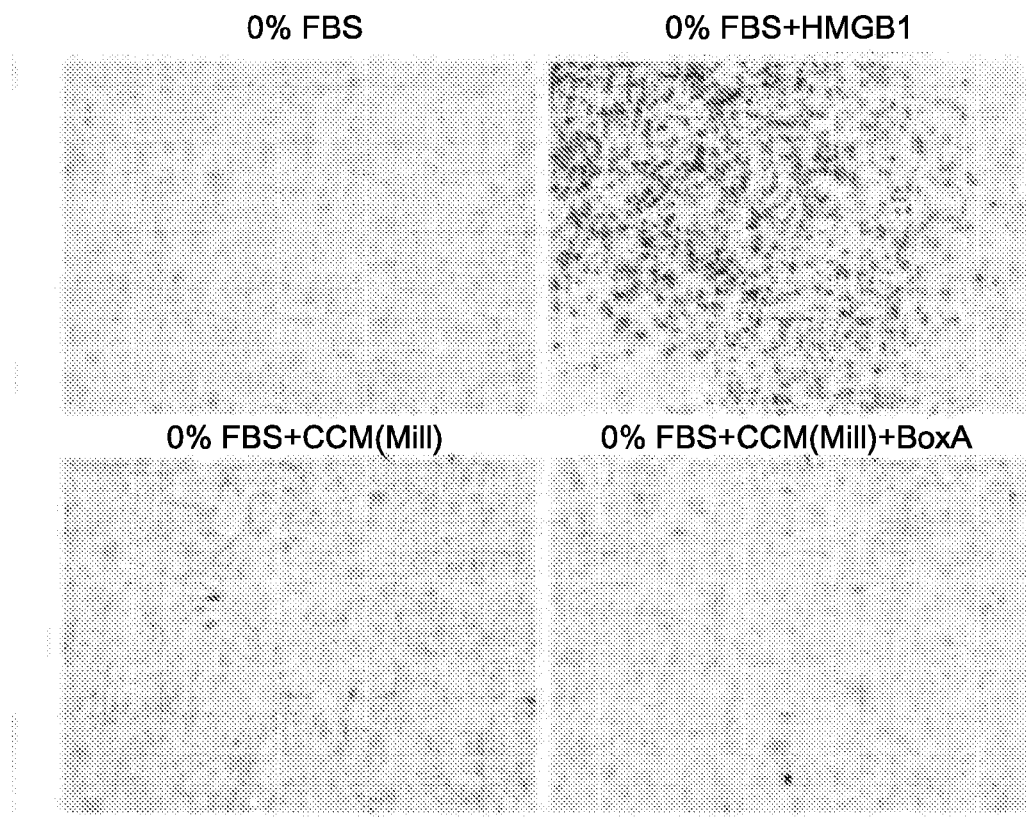
Figure 5E:
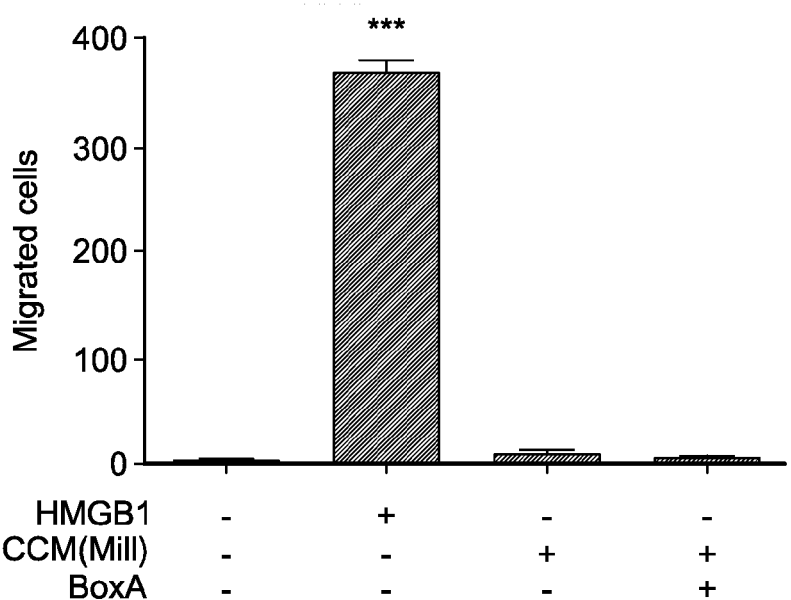
Figure 7A:
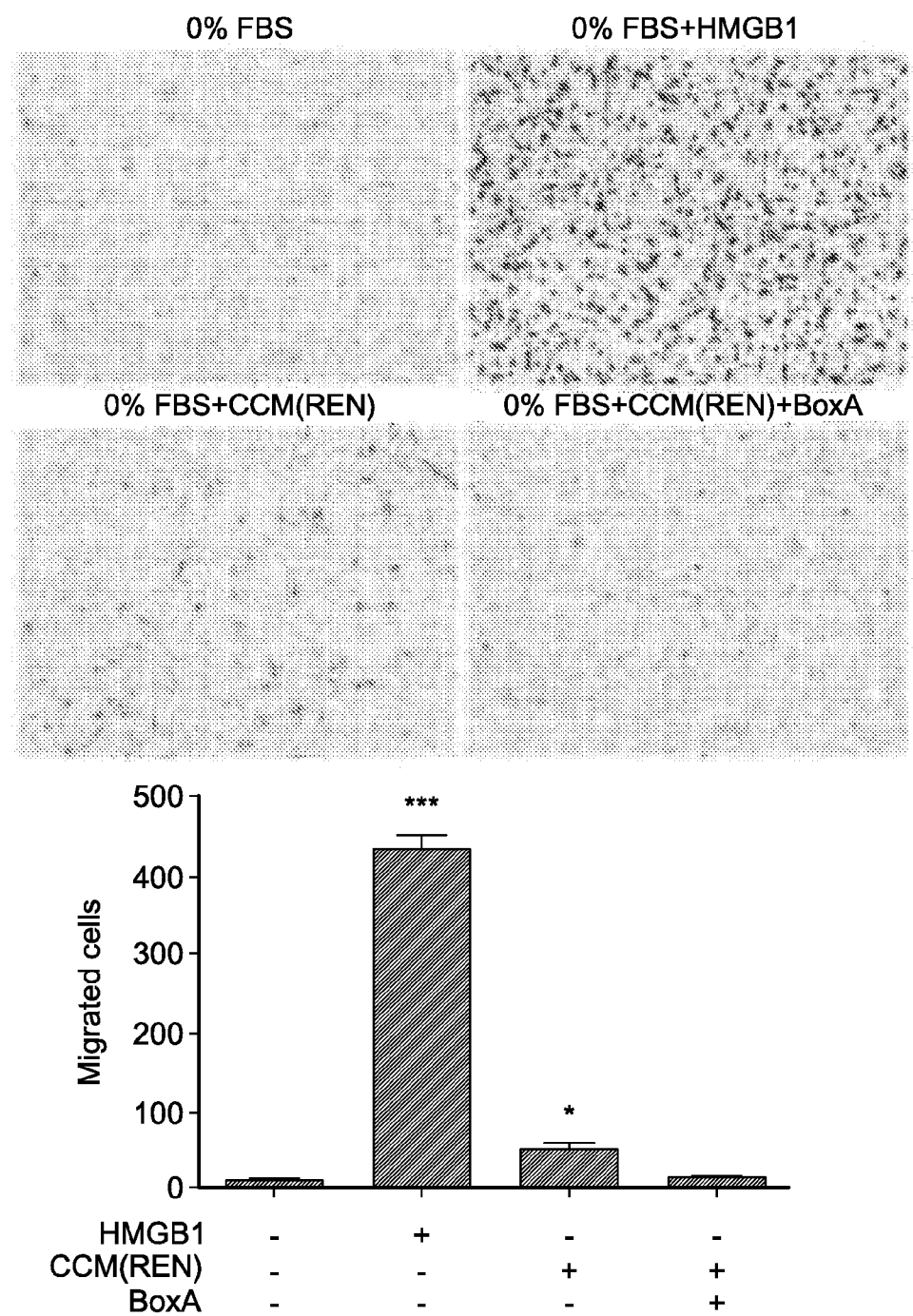
FIG. 7A shows that conditioned concentrated media from REN cells induced the migration of PPM-Mill cells.
Figure 7B:
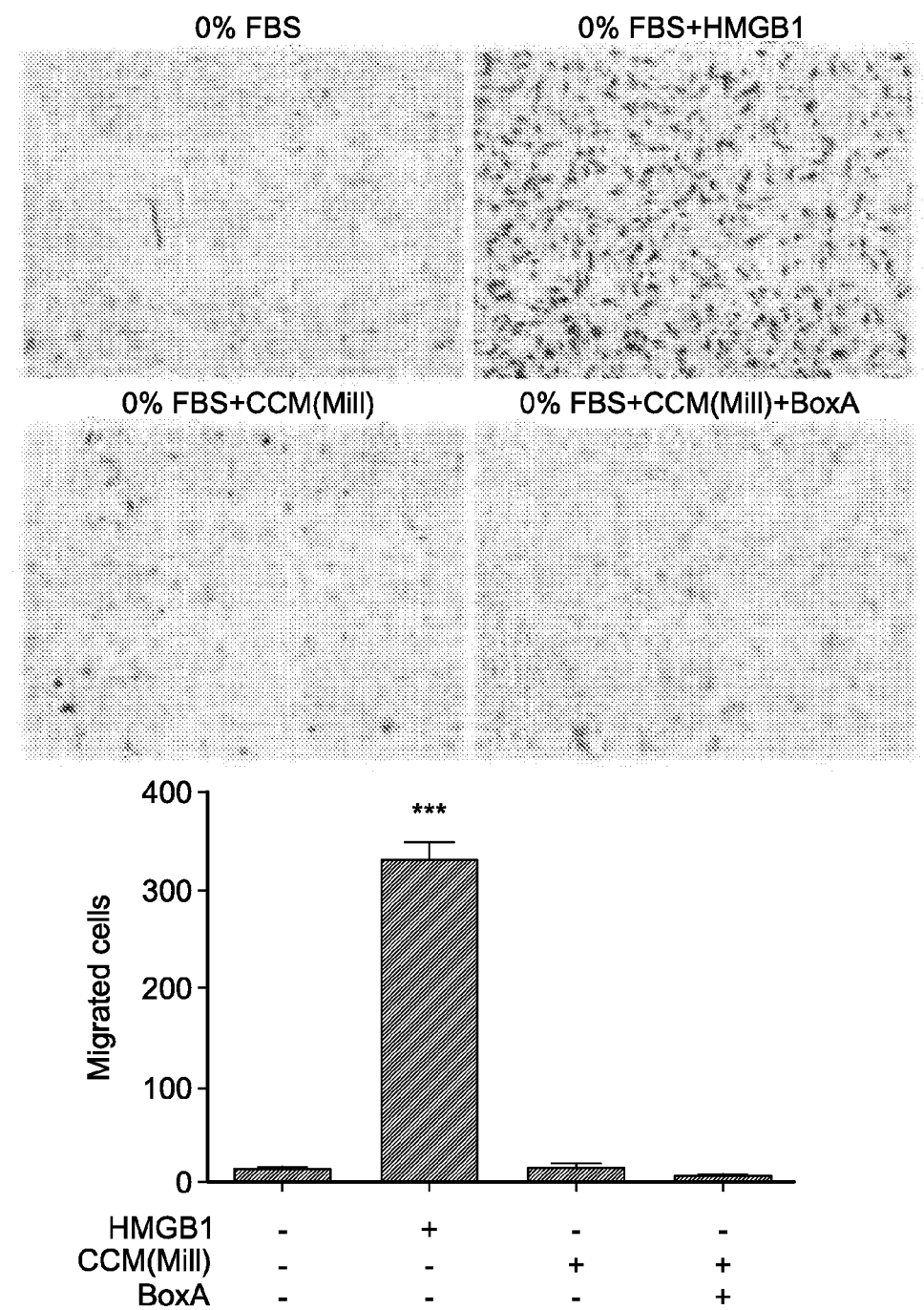
FIG. 7B shows that migration was blocked by the addition of BoxA.
Figure 7C:
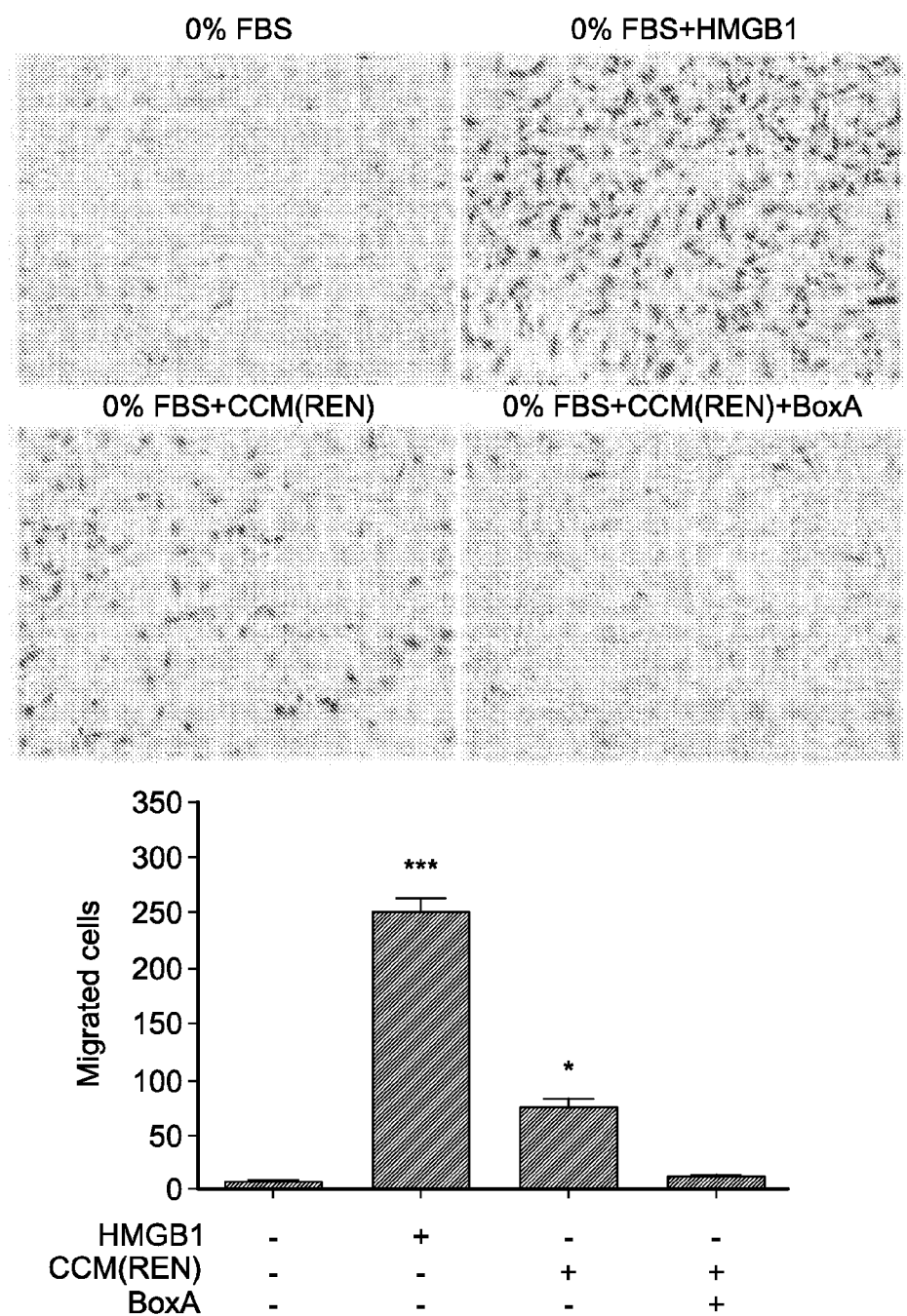
FIG. 7C shows that conditioned concentrated media from REN cells induced the migration of PPM-Phi cells.
Figure 7D:
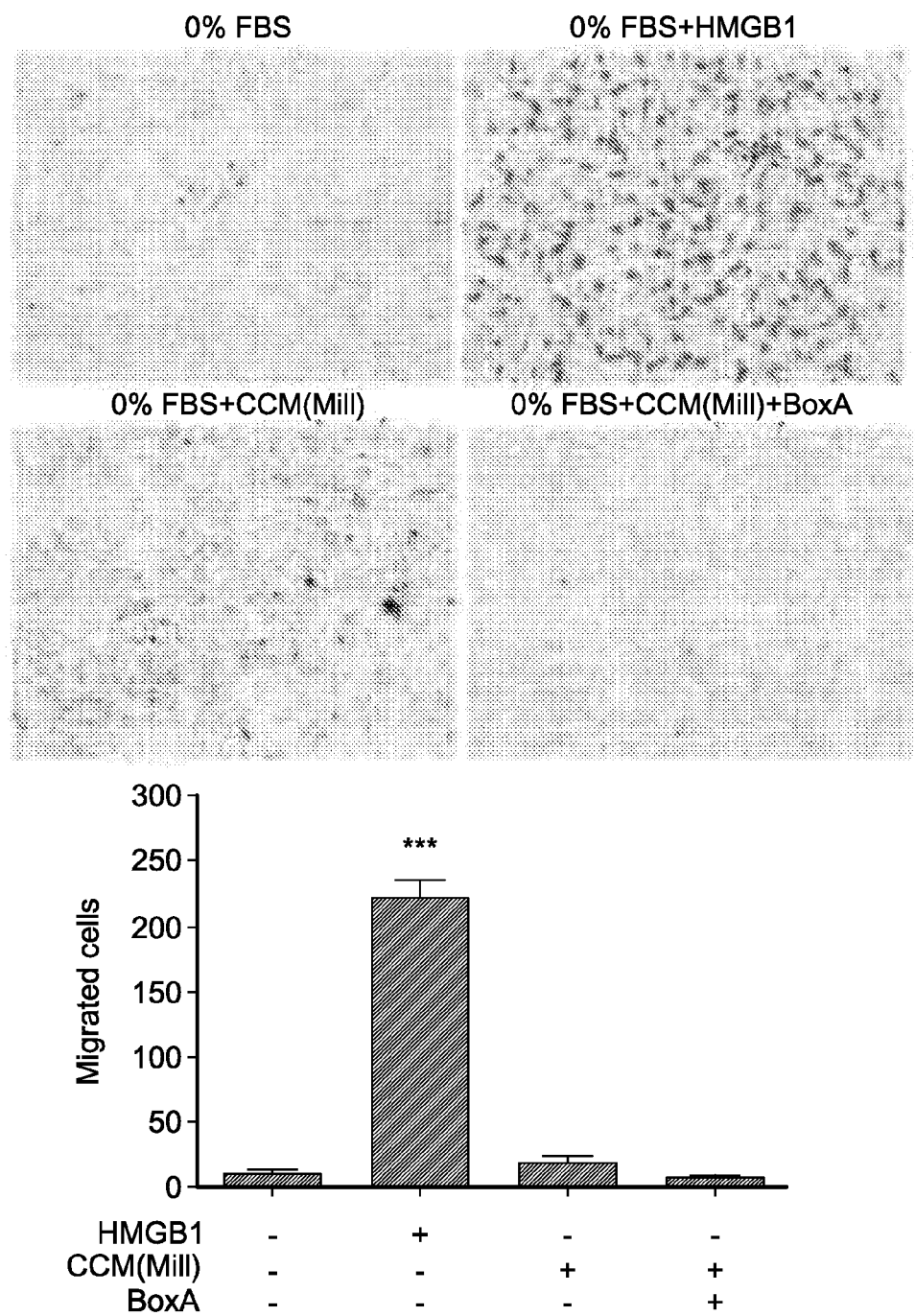
FIG. 7D shows that migration was blocked by the addition of BoxA.

Conditioned media from REN cells (high producers of HMGB1) induced the TRANSWELL system migration of REN cells themselves (FIG. 5D), of PPM-Mill cells (FIG. 7A) and PPM-Phi cells (FIG. 7C). Migration was blocked by the addition of BoxA. Instead, conditioned media collected from PPM-Mill cells (low producers of HMGB1) did not induce any significant chemotactic response in any of the 3 MM cell lines tested (FIG. 5E; FIGS. 7B and 7D). PPM-Mill cells do not express or secrete high levels of HMGB1 and thus can represent a negative control. These results demonstrate that HMGB1 secreted by MM cells is bioactive.

Example 4

MM Cells Require HMGB1 for Survival

The high HMGB1-secreting cell lines Ren (99.0±6.0 ng/ml) and PPM-Phi (333.0±17.6 ng/ml) and the lowest HMGB1-secreting cell line, PPM-Mill (17.4±4.8 ng/ml) were tested for cell viability and cytotoxicity following HMGB1 inhibition.

Briefly, MM were seeded in a 96-well tissue culture plate at a density of $10^4$ cells per well and incubated for 24 hours in DMEM with 1% FBS containing one of the HMGB1 antagonists: BoxA (100 ng/ml); anti-HMGB1 (1 µg/ml) (010910 obtained from DiaPro Diagnostics (Milan, Italy)); or anti-RAGE (1.7 µg/ml). Mouse IgG (1.7 µg/ml) were used as control. The CELLTITER reagent 96 Aqueous Cell Proliferation Assay-MTS (Promega, Madison, Wis.) was used to check cell metabolic activity according to manufacturer's instruction. Cytotoxicity was assessed with the LDH cytotoxicity detection kit (Roche, Germany) according with manufacturer's instruction. quadruplicate and performed twice.

Figure 8C:
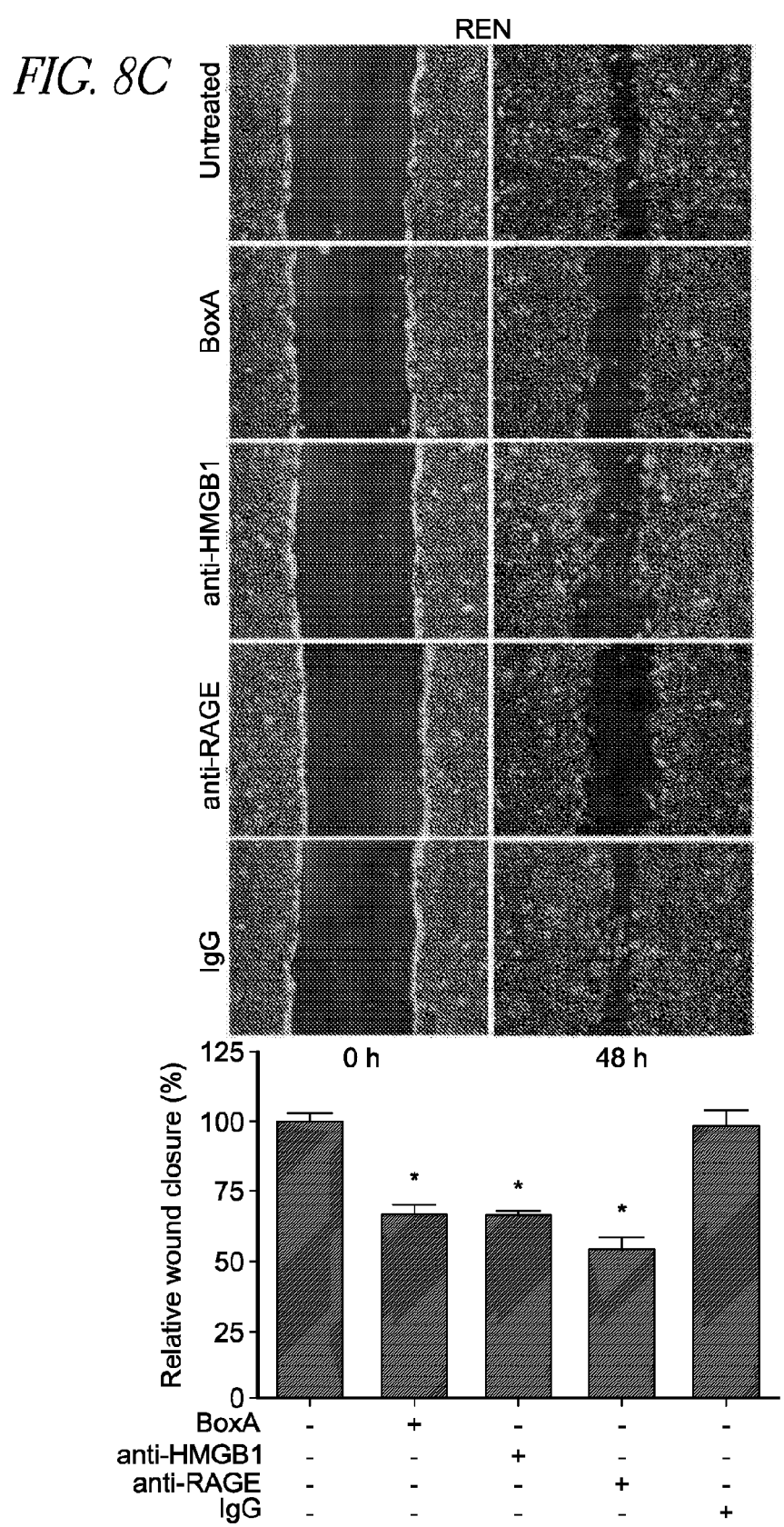
FIG. 8C shows that wound closure time of REN cells was significantly increased by all HMGB1 antagonists.
Figure 9A:
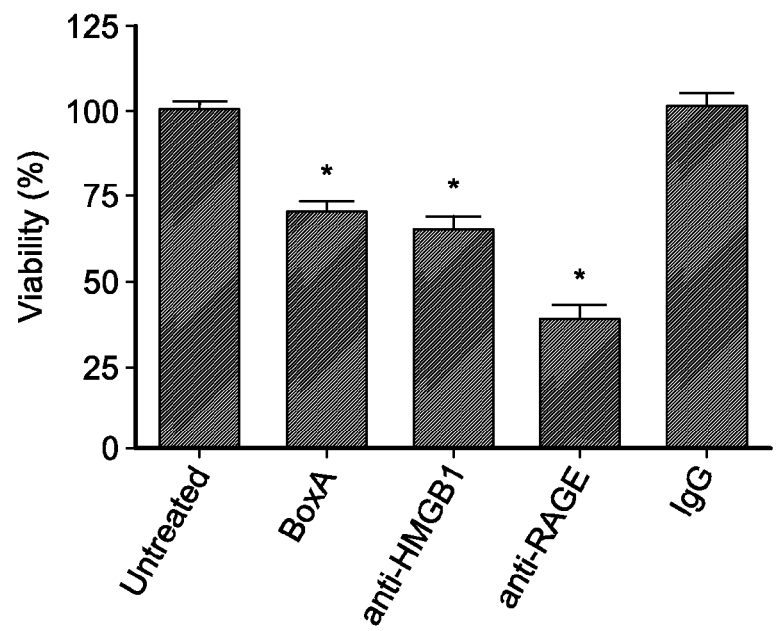
FIG. 9A is a graph representing a viability assay showing that inhibition of HMGB1 by BoxA or anti-HMGB1 or anti-RAGE antibodies substantially decreased the viability of PPM-Phi cells.
Figure 9B:
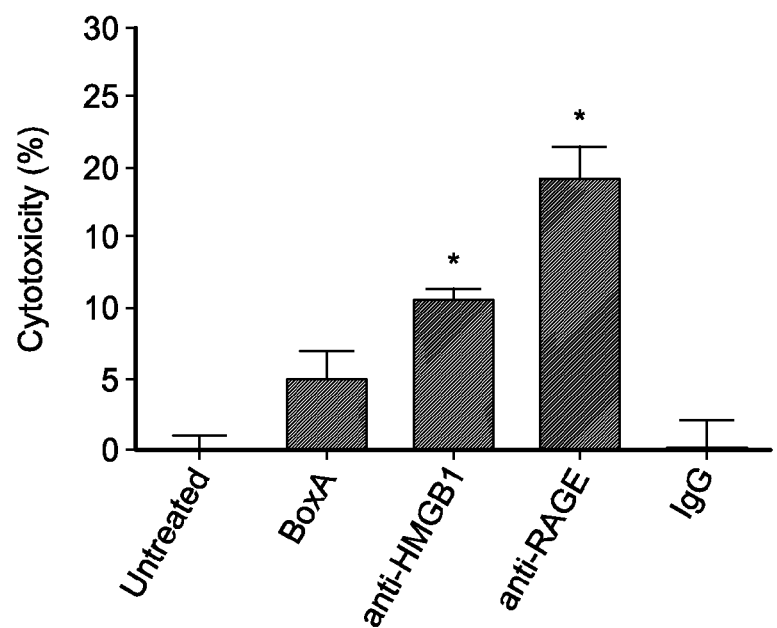
FIG. 9B is a graph representing a cytotoxicity assay showing that anti-HMGB1 and anti-RAGE antibodies induced substantial cytotoxicity (P<0.05) in PPM-Phi cells.

Inhibition of HMGB1 by BoxA or anti-HMGB1 or anti-RAGE antibodies substantially decreased the metabolic activity of REN (FIG. 8A) and PPM-Phi cells (FIG. 9A) but had mild effects on PPM-Mill cells (FIG. 8A), which do not express or secrete high levels of HMGB1 and thus can represent a negative control. Reduced metabolic activity can be due to cytotoxicity, which is assayed by LDH release. Both anti-HMGB1 and anti-RAGE antibodies induced substantial cytotoxicity in REN (FIG. 8B) and PPM-Phi cells (FIG. 9B) and mild cytotoxicity in PPM-Mill cells (FIG. 8B) compared with untreated controls. The degree of cytotoxicity correlated with the amount of HMGB1 secreted by these cells. These results suggest that MM cells that secrete high levels of HMGB1 become dependent on it ("addicted") for cell survival, while cells that secrete low levels do not.

Example 5

HMGB1 Controls Motility in MM Cells

Figure 8D:
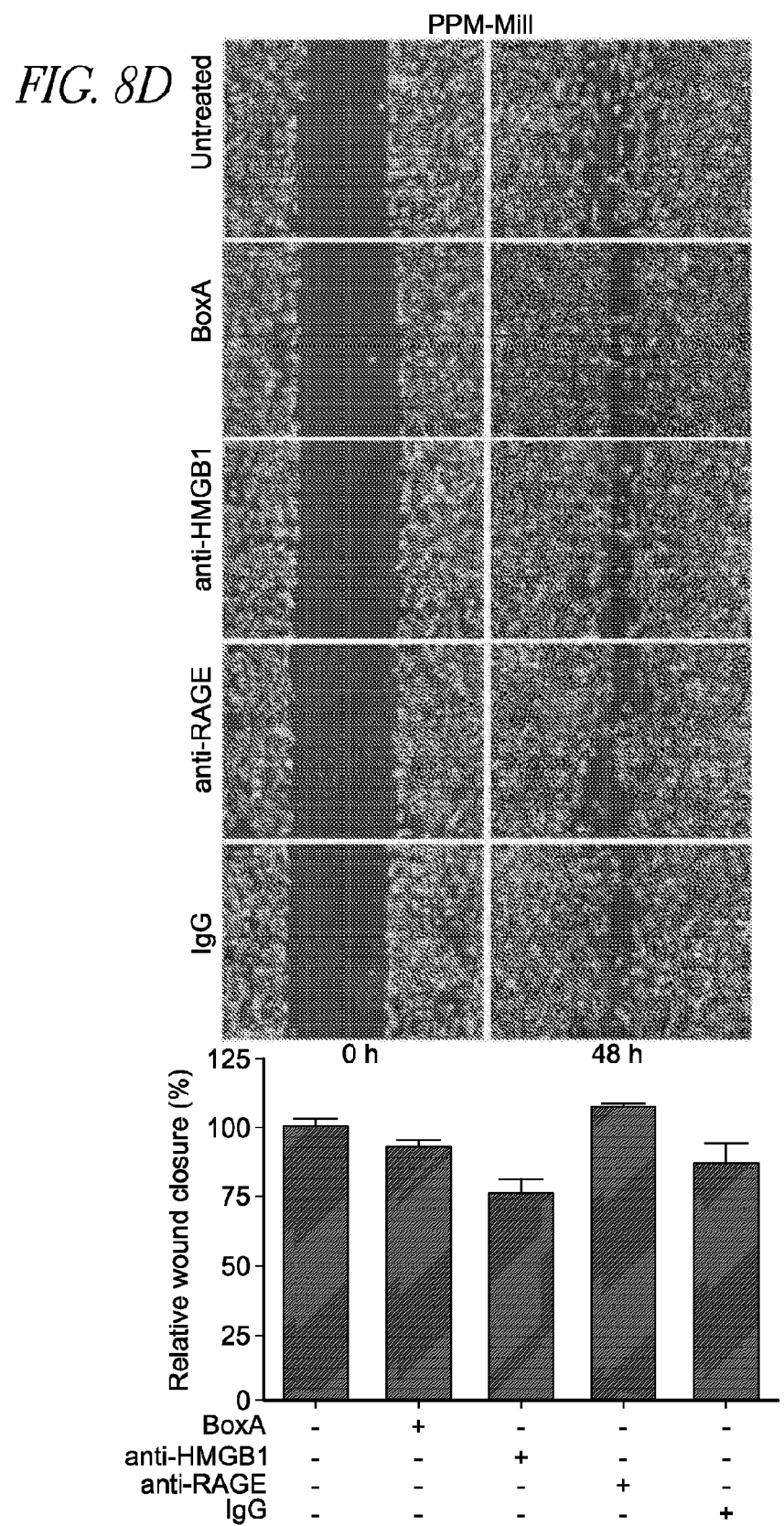
FIG. 8D shows that no effects of HMGB1 antagonists on would closure time of PPM-Mill cells.

The effect of different antagonists on cell motility, as assayed by wound healing was tested. REN and PPM-Phi (high HMGB1 producers) and PPM-Mill (low HMGB1 producer) cells were cultured in 6-well plates and pretreated with BoxA (100 ng/ml), anti-HMGB1 antibodies (1 µg/ml), anti-RAGE (1.7 µg/ml), or an irrelevant IgG control (1.7 µg/ml) for 1 hour prior to wounding of the cell monolayer. Wounding was made to the monolayer using a P200 pipette tip, and wound closure was observed after 48 hours. Experiments were done in duplicate and performed three times. Wound closure time of REN (FIG. 8C) and PPM-Phi (FIG. 9C) cells was significantly increased by all HMGB1 antagonists. No effects were observed on PPM-Mill cells (FIG. 8D), which do not express or secrete high levels of HMGB1 and thus can represent a negative control.

These results show that HMGB1 contributes significantly to cell motility of HMGB1-addicted MM cells, and much less to those of cells that are not addicted.

Example 6

Inhibition of HMGB1 Disrupts MM Cells Anchorage-Independent Growth and Invasion

Figure 10B:
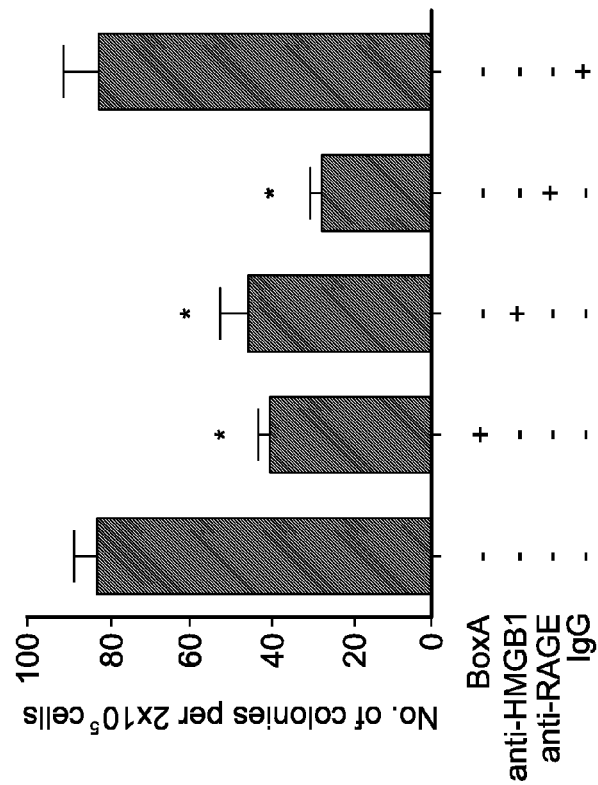
FIG. 10B is a graph showing that treatment of REN cells with HMGB1 antagonists decreased the number of the colonies.
Figure 10A:
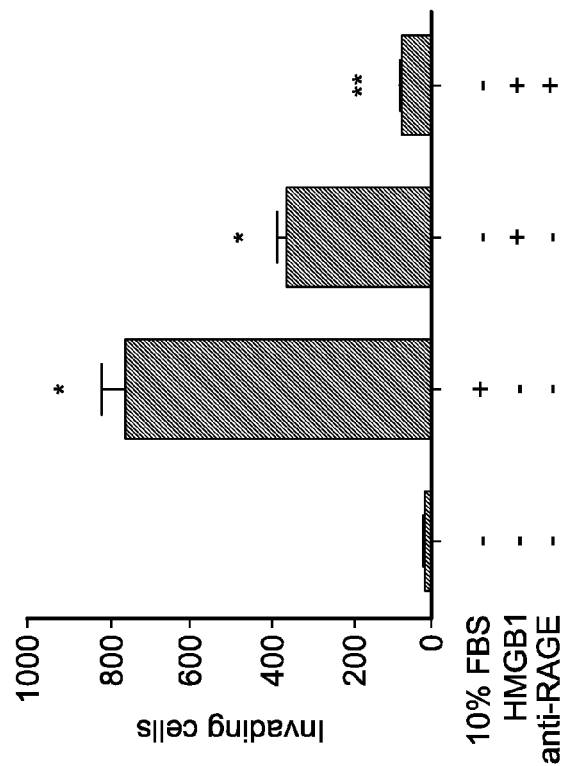
FIG. 10A is a graph showing that treatment of REN cells with HMGB1 antagonists inhibited HMGB1-induced cell invasion.
Figure 10C:
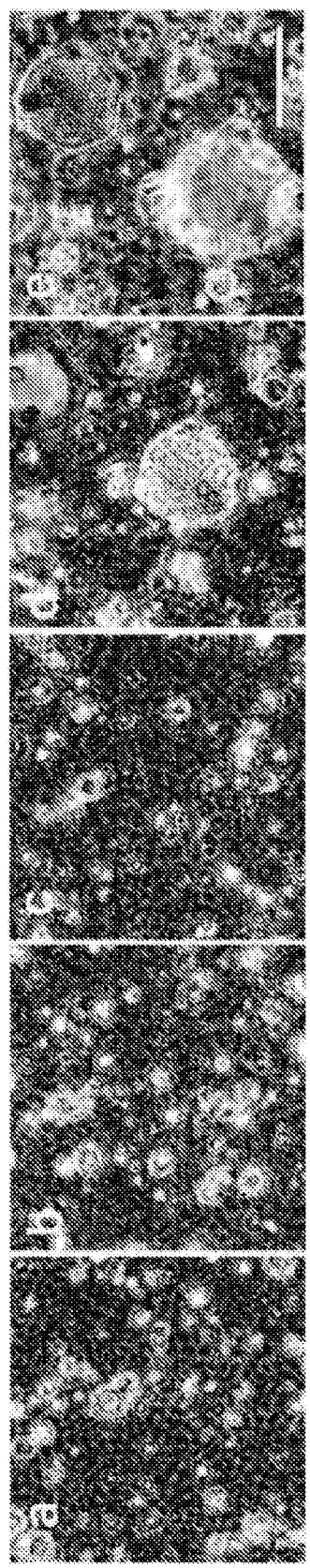
FIG. 10C shows that treatment of REN cells with HMGB1 antagonists decreased the size of colonies formed on soft agar.

HMGB1 inhibitors (BoxA, anti-HMGB1, and anti-RAGE) caused a significant decrease in REN anchorage-independent invasion and growth, as indicated by a marked reduction in the number of invading cells (FIG. 10A) and the number (FIG. 10B) and size (FIG. 10C) of colonies.

Briefly, anchorage-independent cell proliferation was determined by the soft agar assay. REN cells ($4 \times 10^3$) were pretreated for 1 hour with either BoxA (100 ng/ml), anti-HMGB1 (1 µg/ml), anti-RAGE (1.7 µg/ml) or irrelevant IgG control (1.7 µg/ml). After pretreatment, cells were mixed with 0.6% agar in DMEM plus 10% FBS (1:1) and placed on top of a 6-well plate precoated with 1.2% agar in DMEM plus 10% FBS (1:1). Cells were cultured at 37° C. with 5% $CO_2$ and fresh medium (DMEM plus 1% FBS) supplemented with one of the HMGB1 inhibitors (BoxA, anti-HMGB1 or anti-RAGE) was added every two days. After 23 days of culture, the number and size of the colonies formed in each treatment were evaluated. For each well, all colonies larger than 0.1 mm in diameter were counted using ImageJ software. Experiments were done in duplicate and performed twice. For the invasion assays, $2 \times 10^5$ MM cells in serum-free DMEM were seeded in the upper compartment coated with MATRIGEL gel. The lower compartment contained serum-free DMEM (negative control) or DMEM plus 10% FBS (positive control), purified recombinant HMGB1 (100 ng/ml) or concentrated medium (200 µl) from REN or PPM-Mill cells.

These data show that disrupting the HMGB1-RAGE interaction inhibits the anchorage-independent growth and invasion of MM cells. Ability to invade and grow in soft agar correlates with enhanced tumor progression and is a hallmark of malignant transformation.

Example 7

Anti-HMGB1 Monoclonal Antibody Reduces Tumor Growth and Enhances Survival in a Mouse Model of MM Severe combined immunodeficient (NOD.CB17-SCID) female mice aged 6 to 8 weeks (Jackson Laboratories, Bar Harbor, Me.) were housed and handled under aseptic conditions, in accordance with our institution's Institutional Animal Care and Use Committee (IACUC) guidelines. Immunodeficient mice were injected intra peritoneum (i.p.) with MM cells (REN/luc cells) ($5 \times 10^5$) suspended in 500 µl of PBS, as described (Bertino P, Piccardi F, Porta C, Favoni R, Cilli M, Mutti L, Gaudino G. Matinib mesylate enhances therapeutic effects of gemcitabine in human malignant mesothelioma xenografts. Clin Cancer Res. 2008; 14(2): 541-548).

Xenografts were visualized by luminescence after D-luciferin injection (150 mg/kg), using the In vivo Imaging System (IVIS™, Xenogen Corp., Alameda, Calif.), with regions of interest (ROI) quantified as total photon counts by Living Image software (Xenogen Corp.). An elapsed period of 4 days was allowed for the formation of detectable tumor nodules by IVIS imaging. Mice were then weighed and stratified into controls (IgG and PBS) and treatment (anti-HMGB1 mAb) groups of seven animals each.

The "treatment" group received a total of 1.8 mg/mouse of anti-HMGB1 mAb (010910 obtained from DiaPro Diagnostics (Milan, Italy)) divided into 200 µg i.p. doses on days 4, 6, 8, 10, 12, 17, 24, 31, and 38. Control groups received either i.p. injections of matched isotype control (200 µg/mouse/injection) or PBS at the same schedule as the anti-HMGB1-treated group. Tumor dimension was measured and determined every 7th day as the average radiance (photons/s/cm2/sr). Mice were killed and necropsied when tumor developments caused severe ascites limiting the animal's mobility.

Statistical significance between two groups of interest was evaluated by unpaired Student's t test. Differences were considered significant at $P<0.05$. Differences in the HMGB1 levels in human sera were evaluated by Mann-Whitney U-test. For the SCID MM xenografts experiment, differences across groups were assessed by fitting a parametric model to the survival time data. A Weibull distribution was assumed for the random disturbance term. The LIFEREG procedure in SAS 9.2 performed the analysis.

Figure 11A:
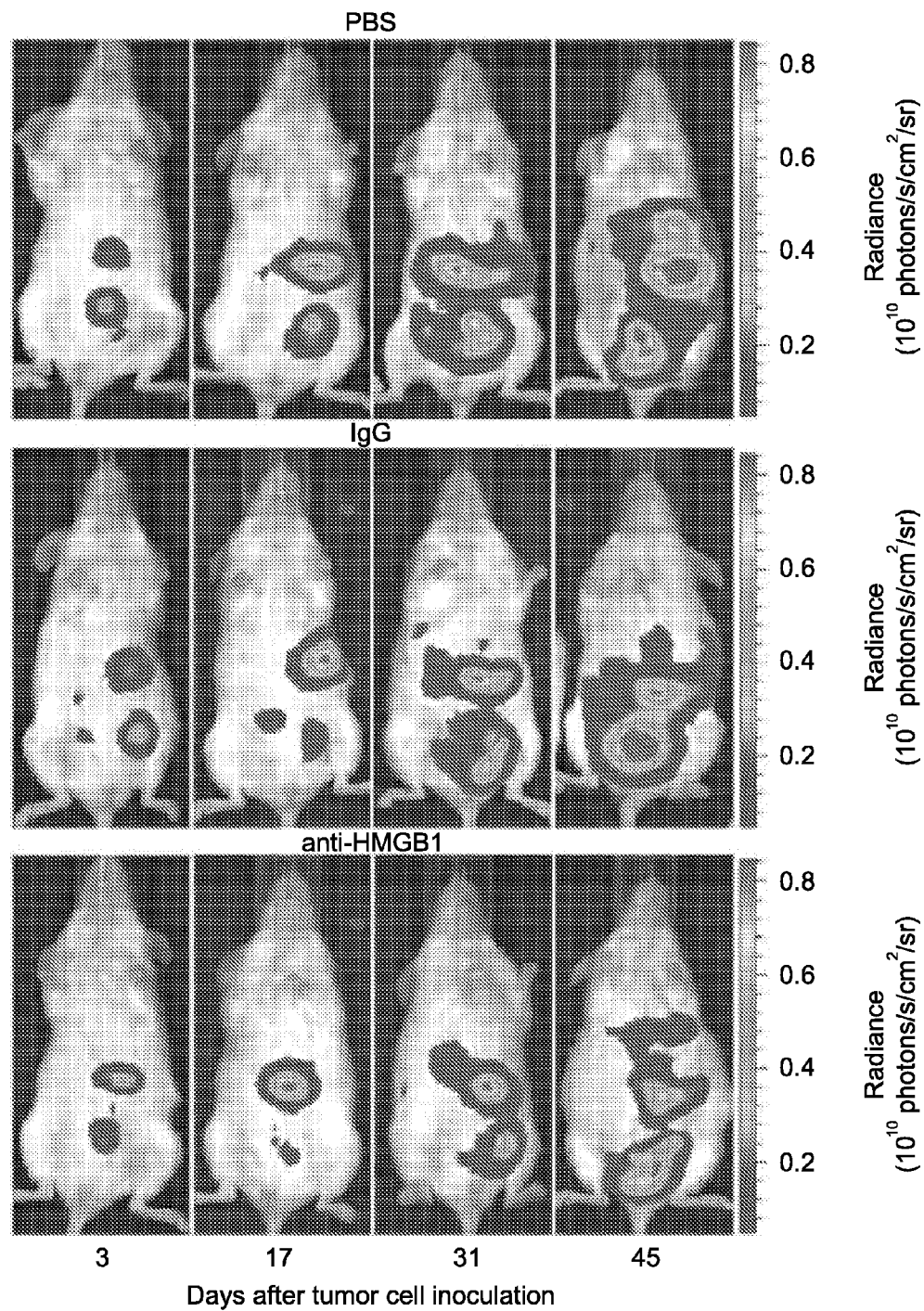
FIG. 11A shows in vivo bioluminescence imaging of mice bearing luciferase-transduced MM cells and injected i.p. with a neutralizing anti-HMGB1 mAb or an irrelevant IgG or vehicle (PBS).
Figure 11B:
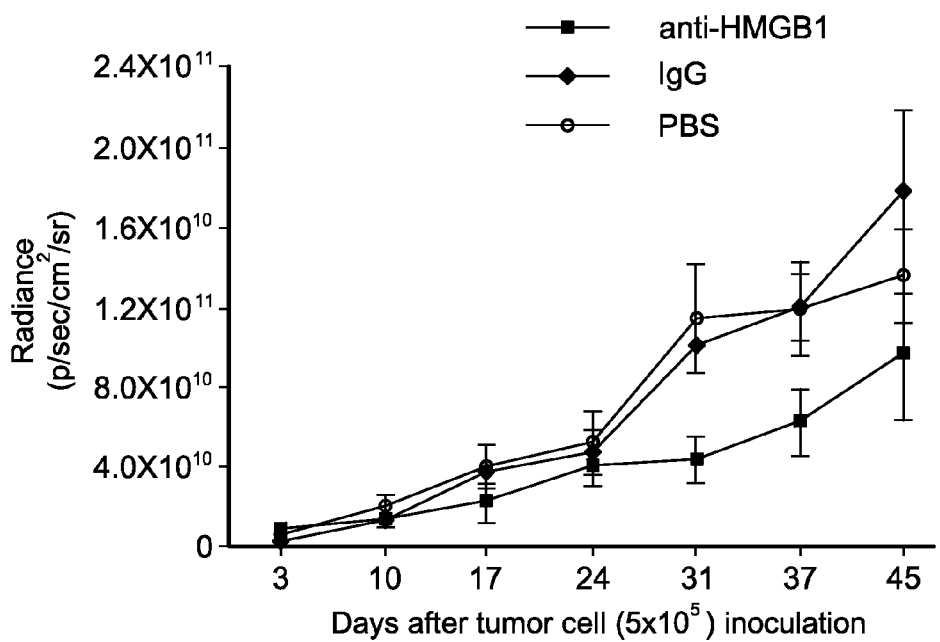
FIG. 11B is a graph quantifying the bioluminescence of one representative mouse from each group.
Figure 11C:
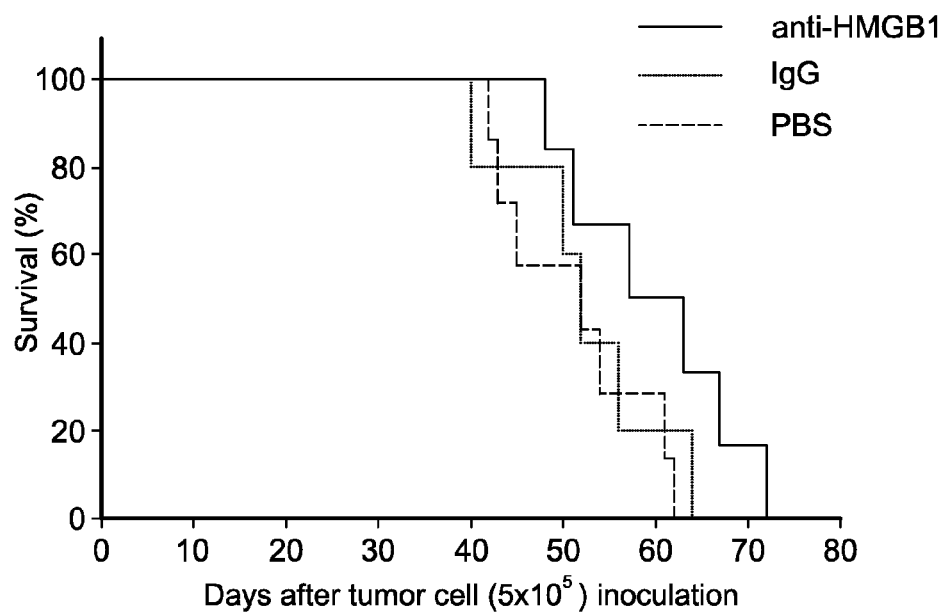
FIG. 11C is a survival curve showing that inhibition of HMGB1 with anti-HMGB1 mAb enhanced animal survival in comparison with PBS and IgG control groups.
Figure 12:
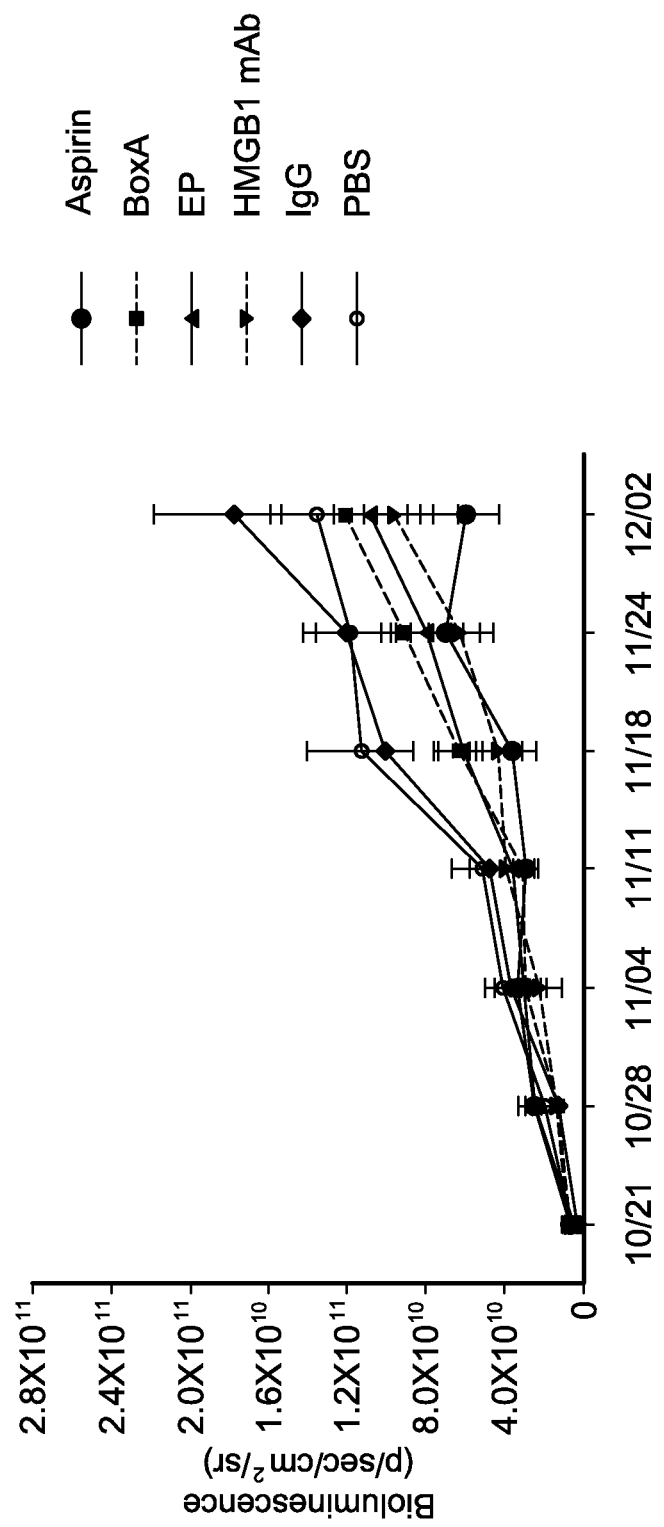
FIG. 12 is a graph quantifying the bioluminescence of luciferase-transduced MM cells in mice treated with aspirin, BoxA, ethyl pyruvate, HMGB1 mAb, IgG, or PBS.

Mice treated with anti-HMGB1 showed significant reduction in tumor growth at 45 days after implantation with MM cell Xenografts ($P<0.05$; FIGS. 11A and 11B). The results showed that the anti-HMGB1 group also had significantly longer survival than both the IgG (P=0.032) and PBS (P-0.047) groups (FIG. 11C).

Figure 18A:
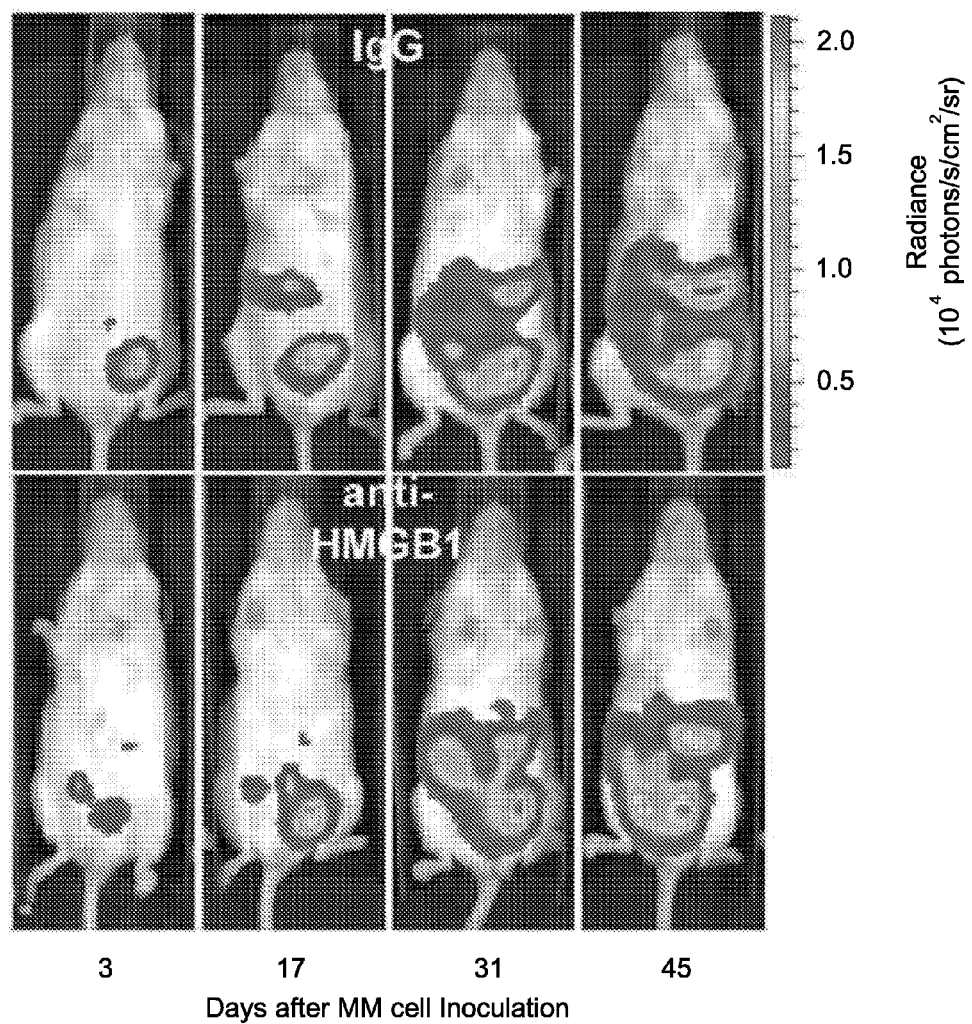
FIG. 18 shows treatment with anti-HMGB1 monoclonal antibody does not reduce tumor growth of "non-addicted" MM cell line (PPM-Mill). (A) Bioluminescence imaging of mice xenografted i.p. with 5×105 luciferase-transduced MM cells (PPMMill/luc) shows tumor development. Mice were imaged on the indicated days after inoculation and injected i.p. at days 4, 6, 8, 10, 12, 17, 24, 31, and 37 with neutralizing anti-HMGB1 mAb, an irrelevant isotype-matched mAb (IgG). One representative mouse from each group is shown. (B) No statistically significant difference is observed in the tumor growth rate of mice injected with anti-HMGB1 mAb in comparison with isotype-matched IgG control. Mean±SEM of each group is shown (n=10 per group).
Figure 18B:
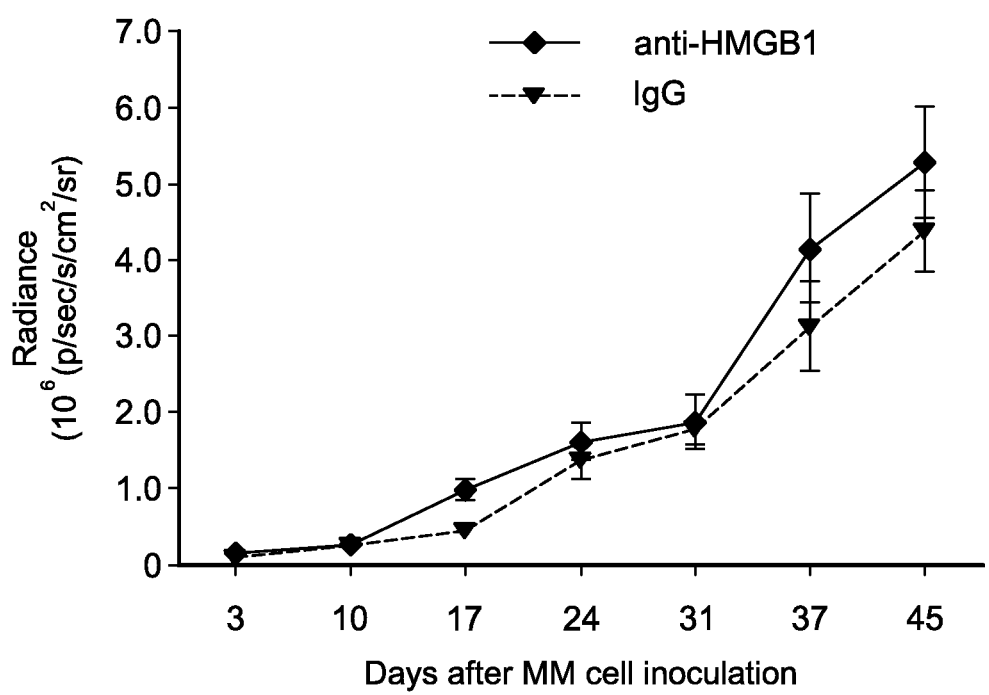

In contrast, treatment with anti-HMGB1 mAb did not significantly inhibit tumor growth in mice inoculated with PPM-Mill cells, which are not "addicted" to HMGB1 (FIGS. 18A and B).

In summary, mice injected with REN, a HMGB1 secreting MM cell line, and treated bi-weekly with an anti-HMGB1 mAb showed a significant decrease in MM tumor growth compared to control animals treated with an irrelevant mouse IgG1. Treatment with anti-HMGB1 mAb also resulted in prolonged survival.

Example 8

Anti-HMGB1 Antibody Reduces Tumor Growth and Enhances Survival in a Mouse Model of MM Immunodeficient mice are injected intra peritoneum (i.p.) with MM cells as described in Example 7 and four days later treated with any of the anti-HMGB1 antibodies described herein. The anti-HMGB1 antibody reduces tumor growth and/or extends survival of the mice.

Example 9

Aspirin, Ethyl Pyruvate, and BoxA Reduce Tumor Growth in a Mouse Model of MM Immunodeficient mice were injected intra peritoneum (i.p.) with MM cells as described in Example 7 and four days later treated with aspirin (25 mg/kg/day orally), ethyl pyruvate (80 mg/kg/day), BoxA (400 µg/mouse/injection for the first two weeks), HMGB1 antibody (200 µg/mouse/injection), control IgG (200 µg/mouse/injection), or control PBS. The data show that treatment with aspirin, ethyl pyruvate, BoxA, or HMGB1 antibody reduced tumor growth in vivo compared to control IgG or PBS.

Example 10

Aspirin Delays Human MM Cell Growth in Mice

Figure 13A:
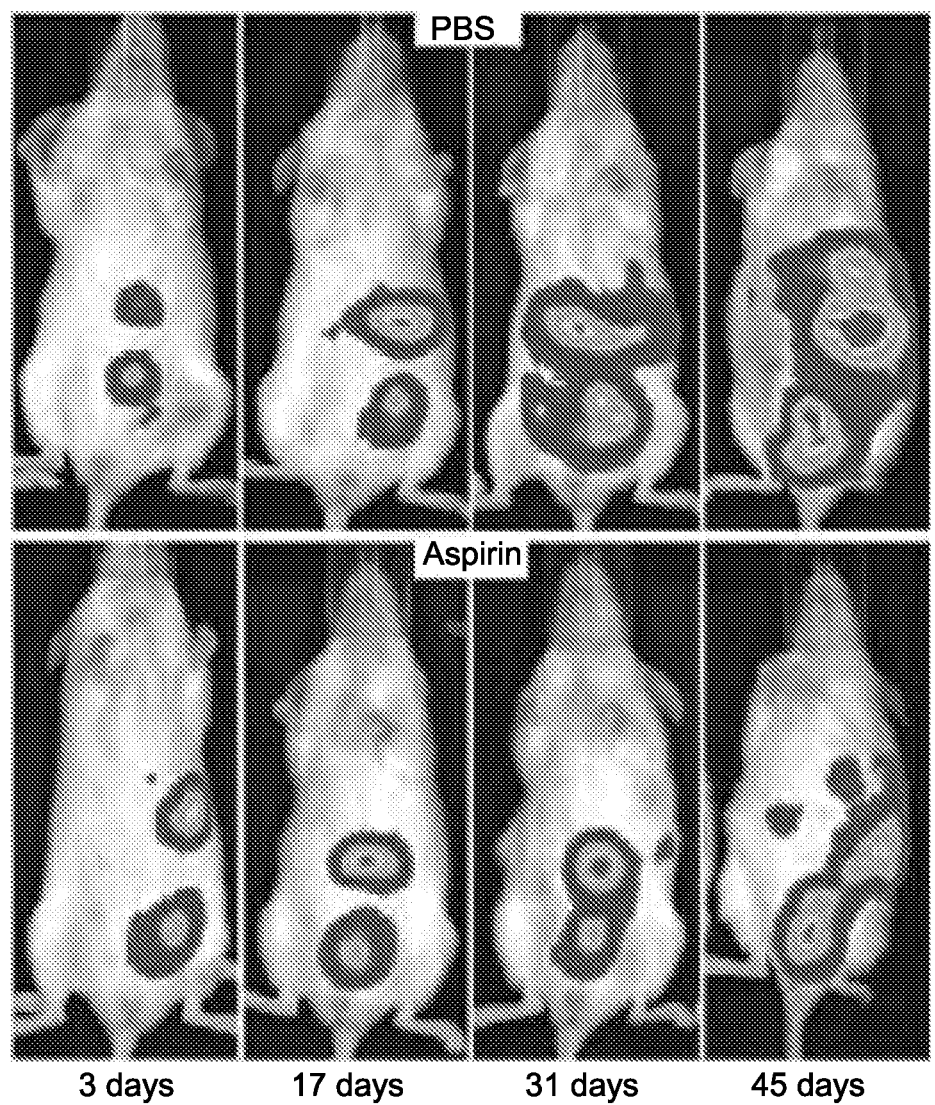
FIG. 13A shows in vivo bioluminescence imaging of mice pre-treated with aspirin or PBS and given aspirin or PBS while bearing luciferase-transduced MM cells.
Figure 13B:
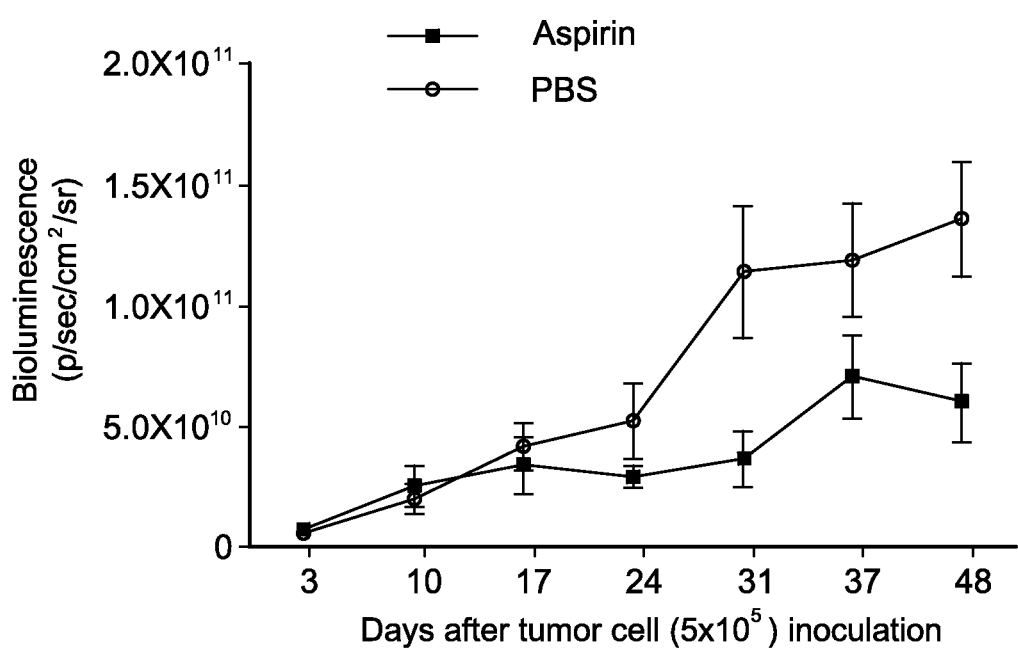
FIG. 13B is a graphical representation of tumor growth of both groups.

SCID mice were pre-treated with aspirin (25 mg/kg/day) or PBS for 5 days before i.p. injection of 300,000 luciferase+ REN human MM cells. The mice were fed with aspirin or PBS every other day for one month. Tumor growth was monitored weekly using an IVIS imaging system. Visual images of REN/luc cells in SCID mice 3, 17, 31 and 45 days after tumor challenge show that tumor growth is inhibited in mice treated with aspirin (FIG. 13A). A graphical representation of tumor growth in SCID mice shows that aspirin treatment inhibited outgrowth of REN human MM cells in vivo (FIG. 13B). These data suggest that long-term aspirin administration may delay MM occurrence after asbestos exposure.

Example 11

Anti-Inflammatory Drug Reduces Tumor Growth in a Mouse Model of MM

Immunodeficient mice are injected intra peritoneum (i.p.) with MM cells as described in Example 7 and four days later treated with any of the anti-inflammatory drugs described herein. The anti-inflammatory drug reduces tumor growth and/or extends survival of the mice.

Example 12

Anti-Inflammatory Drug Delays Human MM Cell Growth in Mice

Immunodeficient mice are pre-treated with any of the anti-inflammatory drugs described herein for 5 days before i.p. injection of MM cells as described in Example 7. The mice are optionally given the anti-inflammatory drug after injection of the MM cells. The anti-inflammatory drug inhibits outgrowth of MM cells in the mice.

Example 13

Anti-HMGB1 Antibody Delays Human MM Cell Growth in Mice

Immunodeficient mice are pre-treated with any of the anti-HMGB1 antibodies described herein for 5 days before i.p. injection of MM cells as described in Example 7. The mice are optionally given the anti-HMGB1 antibody after injection of the MM cells. The anti-HMGB1 antibody inhibits outgrowth of MM cells in the mice.

Example 14

HMGB1 Inhibition does not Induce Cell Death in HM

Figure 14A:
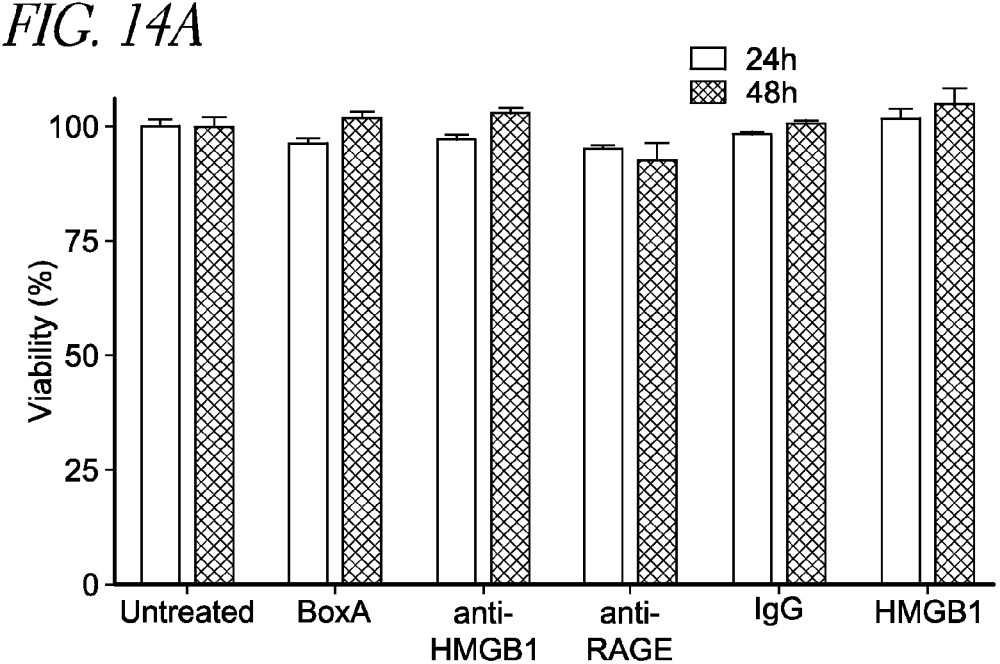
FIG. 14 shows HMGB1 inhibition does not induce cell death in HM. HM were assayed for viability (MTS assay) (A), cell proliferation (B) and cytotoxicity (C) in the presence of BoxA, anti-HMGB1 or anti-RAGE antibodies. HMGB1 addition or inhibition does not significantly affect primary HM in any of the conditions assayed. Experiments were done in quadruplicate and performed twice.
Figure 14B:
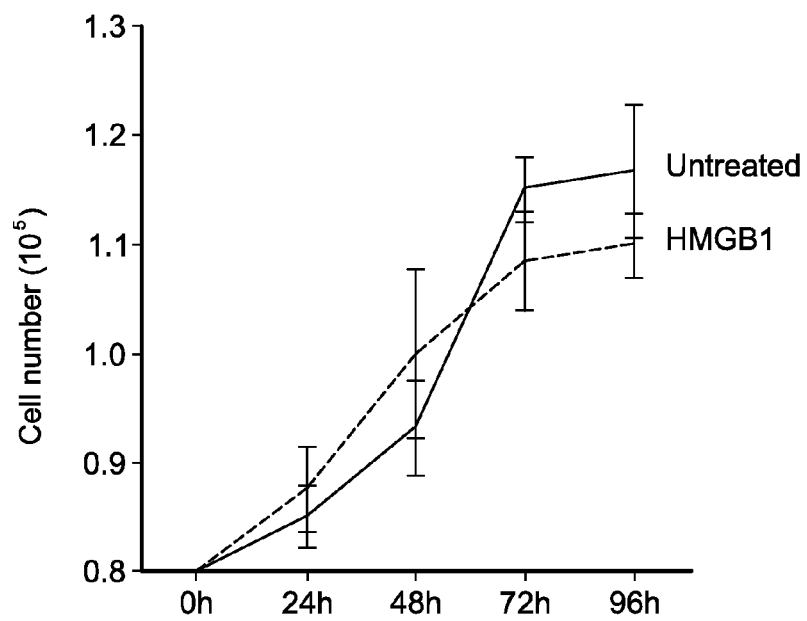
Figure 14C:
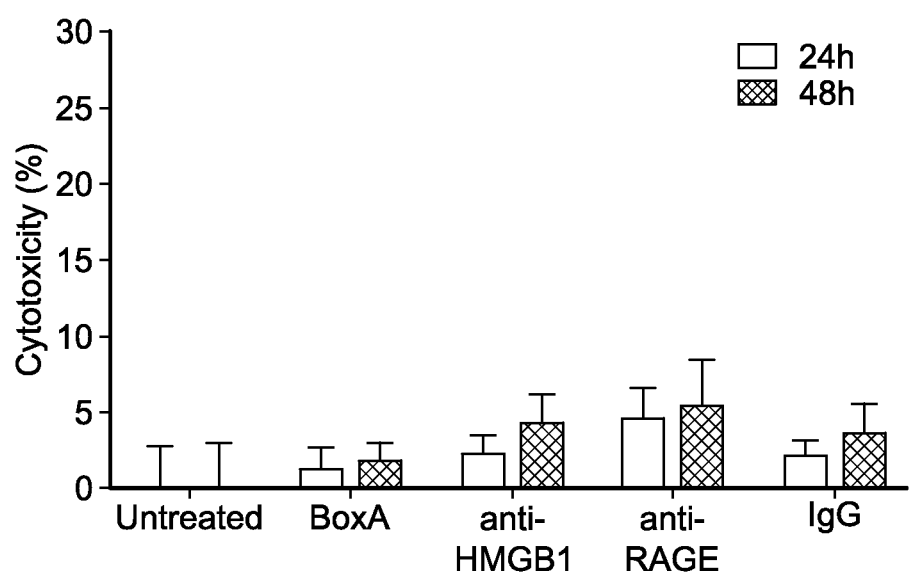

HM were assayed for viability (MTS assay), cell proliferation and cytotoxicity in the presence of BoxA, anti-HMGB1 or anti-RAGE antibodies. HMGB1 addition or inhibition does not significantly affect primary HM in any of the conditions assayed. The results are set forth in FIG. 14. Experiments were done in quadruplicate and performed twice.

Example 15

Inhibition of HMGB1 Induces Apoptosis in MM Cells "Addicted" to HMGB1

Figure 15B:
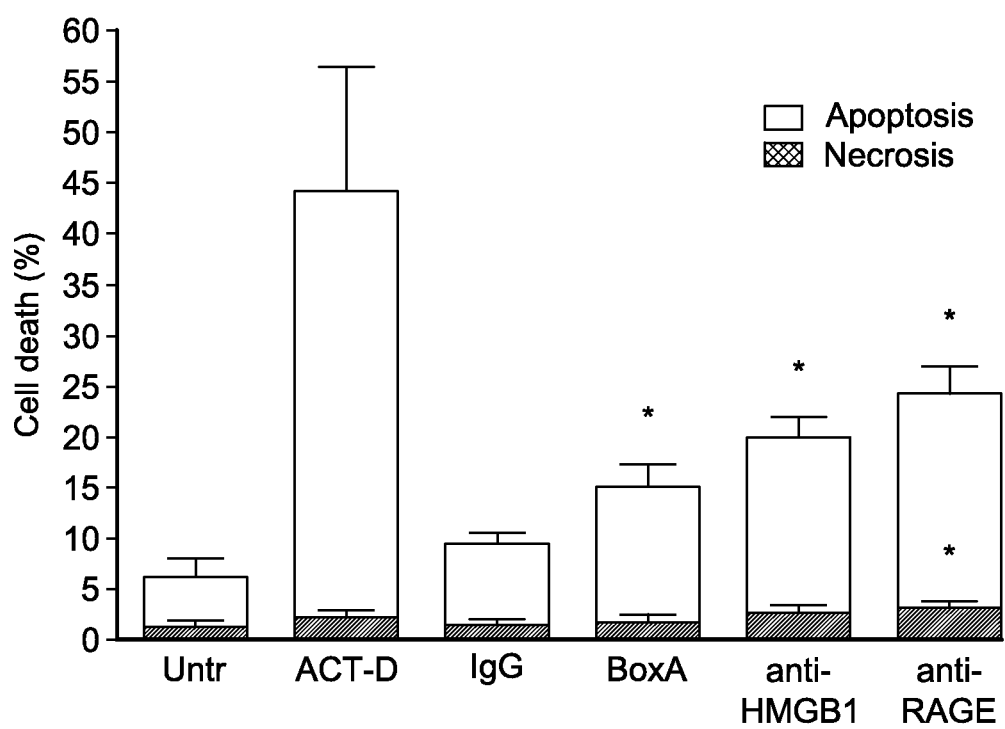
FIG. 15 shows inhibition of HMGB1 induces apoptosis in MM cells "addicted" to HMGB1. Apoptosis and necrosis was assessed in REN (A and B) and PPM-Mill (C and D) cells by flow cytometry analysis with Annexin V and 7-AAD staining. Actynomicin D (0.1 µM) treated cells was used as positive control for apoptosis. Cells in the upper left quadrant (Q1) indicate Annexin V-positive and 7-AAD negative, early apoptotic cells. The cells in the upper right quadrant (Q2) indicate Annexin V-positive and 7-AADpositive, late apoptotic cells. The cells in the lower right quadrant (Q4) indicate Annexin V-negative and 7-AAD-positive, necrotic cells. Representative data were shown for REN (A) and PPM-Mill (C) cells treated with different HMGB1 inhibitors Inhibition of HMGB1 by BoxA or anti-HMGB1 or anti-RAGE antibodies significantly induces apoptosis in REN cells (high HMGB1 producer) but had no effect on PPM-Mill cells (low HMGB1 producer). Significant cell necrosis was observed only in REN cells treated with anti-RAGE mAb. All other HMGB1 inhibitors did not induce significant necrosis in REN or PPM-Mill cells. Bar graphs represent the average percentages of apoptotic (early and late) and necrotic cells ±SEM (n=3) in REN (B) and in PPM-Mill (D) cells. *P<0.05; treated versus untreated.
Figure 15C:
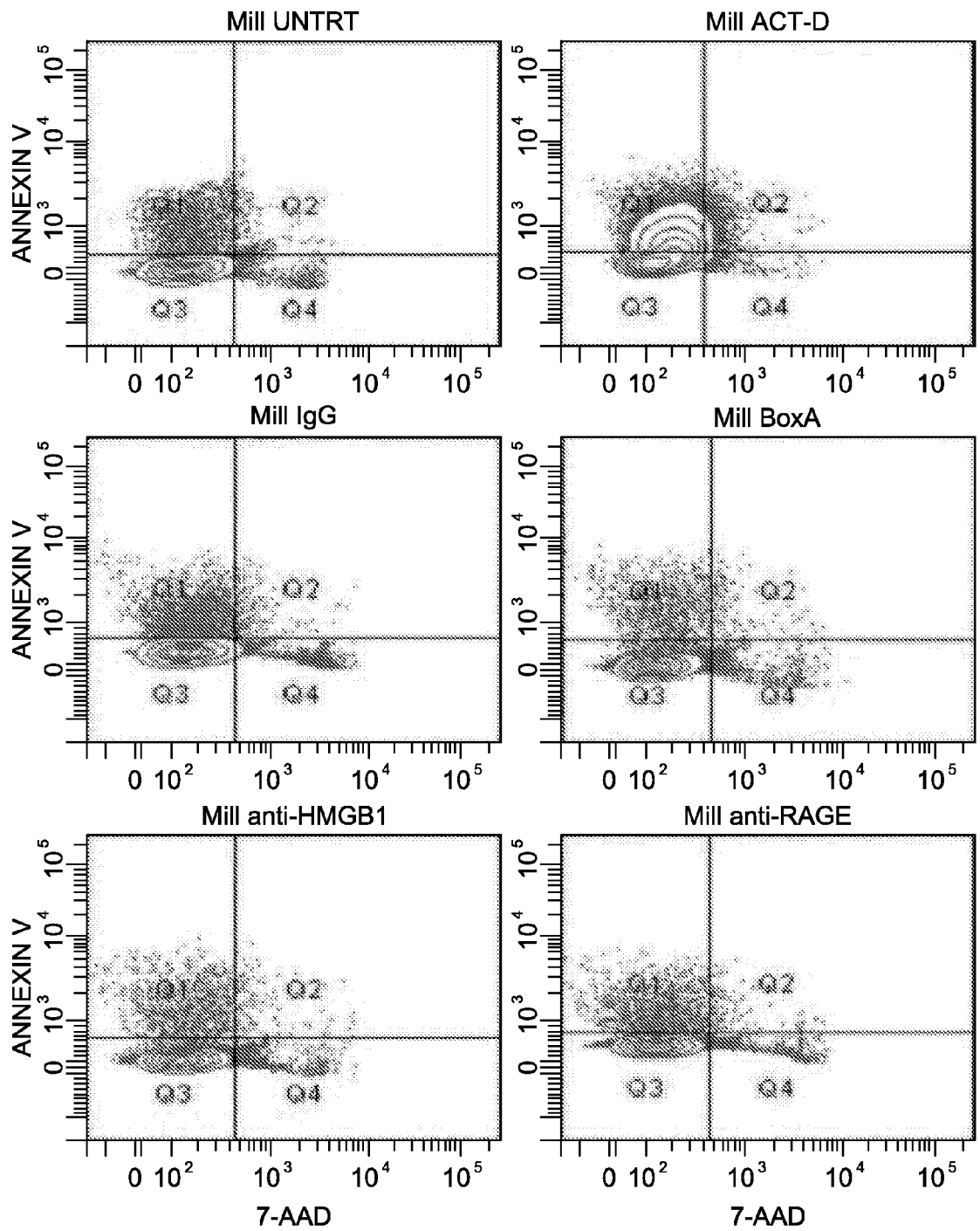
Figure 15D:
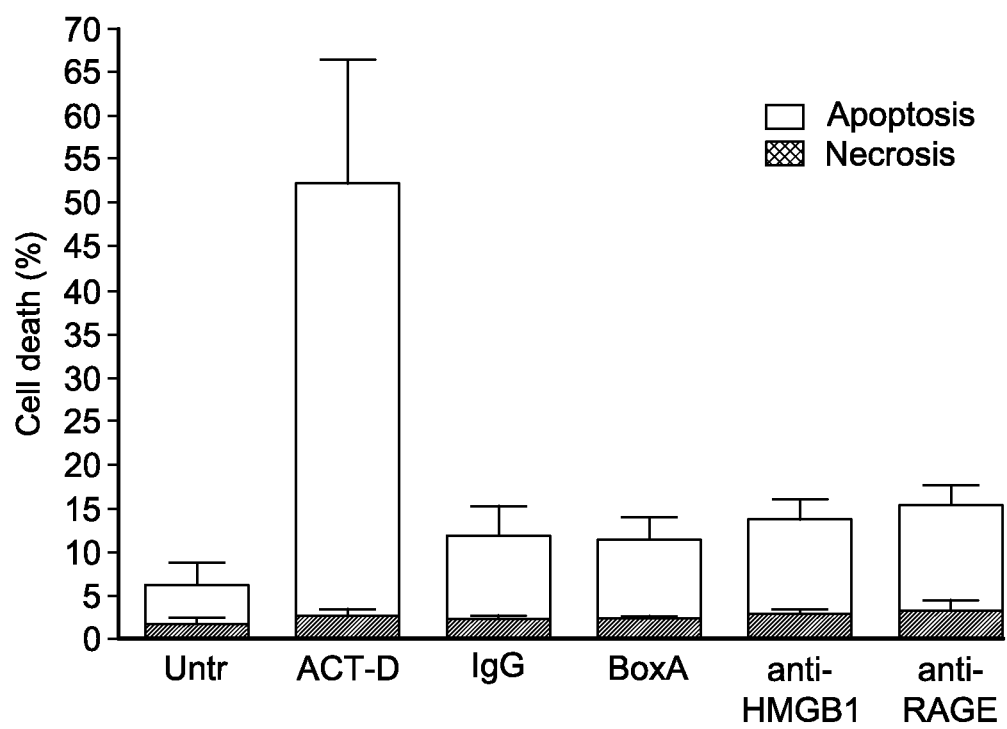

Cell death induced by HMGB1 antagonists was then analyzed. Flow cytometry revealed that BoxA, anti-HMGB1 and anti-RAGE antibodies significantly induced apoptosis in REN cells (FIGS. 15 A and B), but not in PPM-Mill cells (FIGS. 15 C and D). Without intending to be bound by theory, these results strongly suggest that MM cells secreting high levels of HMGB1 are "addicted" to HMGB1 for their viability.

Briefly, the number of apoptotic and necrotic cells was determined using a PE Annexin V Apoptosis Detection Kit I (BD Biosciences). Experiments were performed according to the manufacturer's protocol. Briefly, REN and PPM-Mill cells were culture in 6 well plates and treated for 24 hours with either BoxA (100 ng/ml), anti-HMGB1 (1.0 µg/ml), anti-RAGE (1.7 µg/ml) or irrelevant IgG control (1.7 µg/ml). All cells (attached and floating) were harvested and washed twice with cold PBS, then resuspended in 100 µl of 1× binding buffer at a concentration of $1\times10_5$ cells/ml. The cells were then stained with 5 µl of PE Annexin V and 5 µl of 7-AAD and incubated at RT in the dark for 15 minutes. After incubation, 400 µl of 1× Binding Buffer was added to each tube and the cells were analyzed by flow cytometry within 1 hour by using a BD FACSARIA sorter I, 2 laser, 7 color sorter running BDFACSDIVA software (BD Biosciences). The PE Annexin V signal was collected of the 488 laser in P2 channel with 576/26 filter, while the 7-AAD signal was collected in the P4 channel with the 695/40 filter.

Example 16

HMGB1 Supports the Invasive Phenotype in MM Cells

Figure 16:
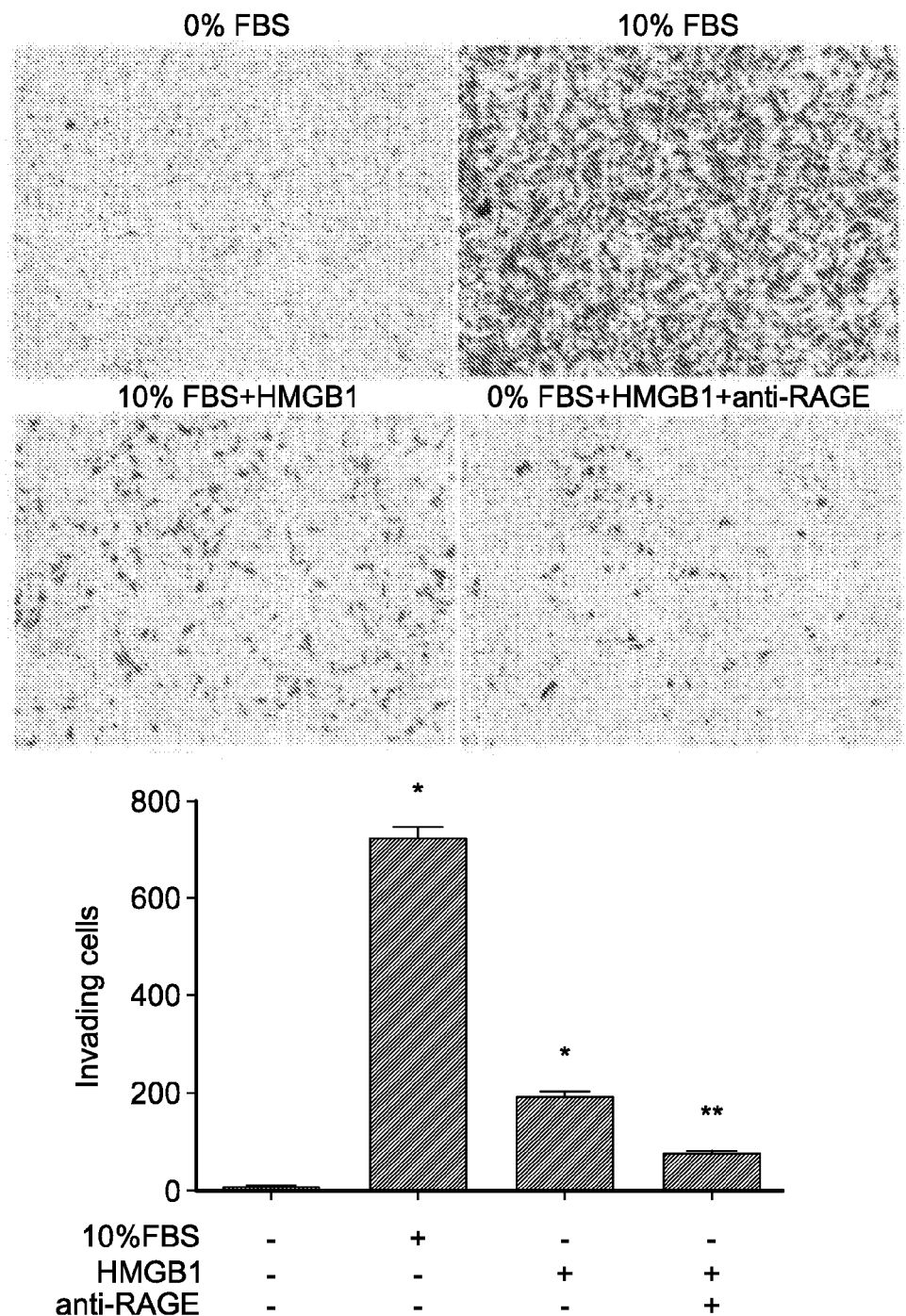
FIG. 16 shows HMGB1 supports the invasive phenotype in MM cells. The addition of exogenous recombinant HMGB1 (100 ng/ml) to the culture media stimulated PPM-Phi cells to invade MATRIGEL gel. Original magnification, ×40. Figure shows representative images from three experiments done in duplicate. Invading cells were counted using ImageJ software and represent mean values per field from at least 3 fields (graph at the bottom). Error bars represent SEM. *P<0.05; HMGB1 and 10% FBS (positive control) versus 0% FBS (negative control). **P<0.05; HMGB1 alone versus HMGB1 plus anti-RAGE.

A MATRIGEL gel invasion assay was performed using PPM-Phi cells, as described previously in Example 6. The results are set forth in FIG. 16, and show that shows HMGB1 supports the invasive phenotype in MM cells.

Example 17

Gene Expression Analysis of REN Cells Treated with HMGB1

Expression analysis was performed with the Affymetrix HumanGene 1.0 ST array, as follows. Briefly, differential gene expression profiles caused by exogenous recombinant HMGB1 or anti-HMGB1 mAb were evaluated using Affymetrix Human GENECHIP chip 1.0 ST array. MM cell line REN was used due to its high expression of HMGB1 and RAGE. The experiments were done in triplicate to ensure reproducibility. REN cells were treated with or without recombinant HMGB1 (100 ng/ml) or anti-HMGB1 mAb (1.0 µg/ml) for 4, 8, 16 and 24 hours separately. At each time point total RNA was isolated using MIRNEASY mini kit (Qiagen) and amplified using Ambion WT expression kit (Invitrogen) according to the manufacturer's manual. Amplified sense strand cDNAs were fragmented and terminally labeled before hybridization. The arrays were stained and scanned using Affymetrix GENECHIP chip Fluidics Station 450 and GENECHIP chip Scanner 3000 7G (Affymetrix) according to the respective manufacturers' instructions. Data were normalized using Robust Multichip Average (RMA) normalization and analyzed using Partek Genomic Suite (Partek).

Figure 17A:
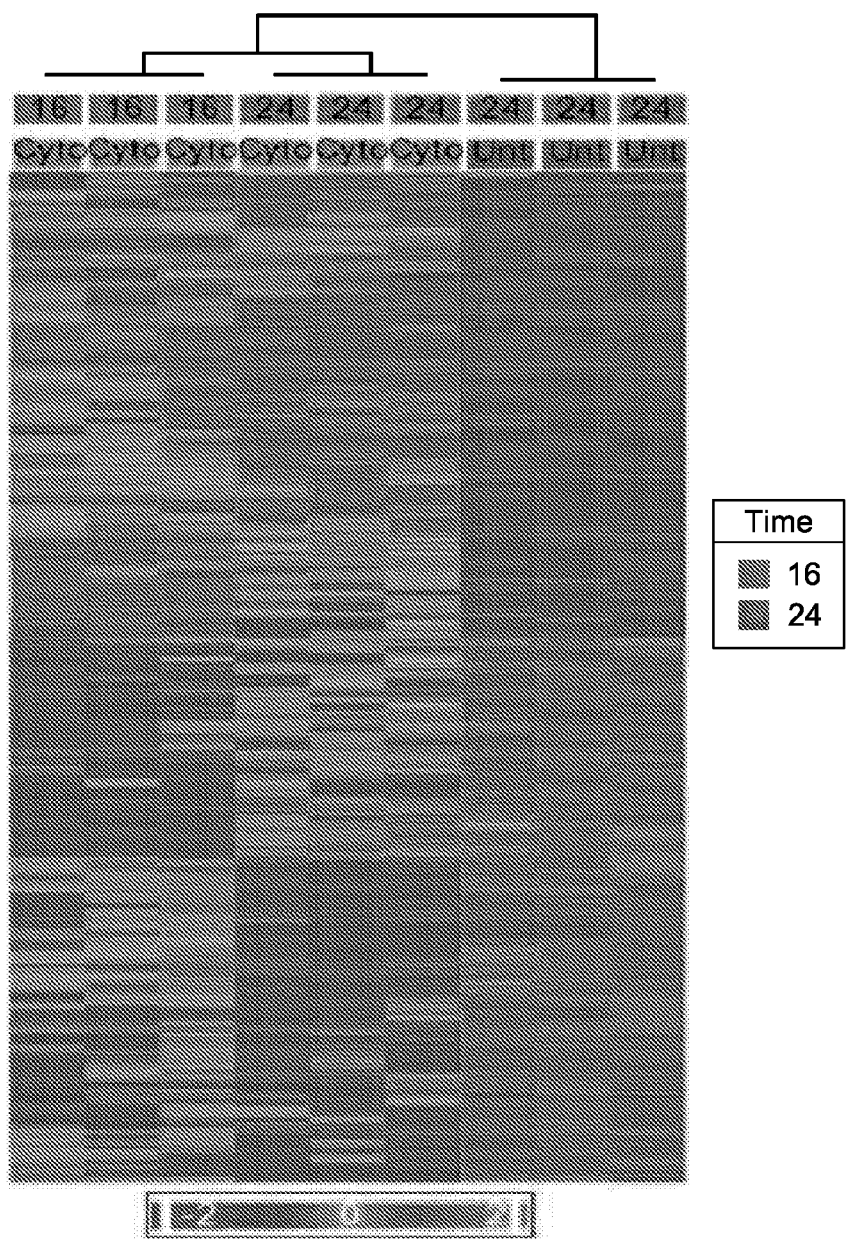
FIG. 17 shows gene expression analysis of REN cells treated with HMGB1. (A) Heatmap of differentially expressed genes (P<0.005) identified at 16 and 24 hours compared with untreated controls at 24 hours. A total of 1380 genes were induced by HMGB1 cytokine treatment. Red represents up-regulation and blue represents down-regulation. (B) Visualization of gene expression changes related to HMGB1 signaling pathway. (C) Canonical pathways significantly changed post HMGB1 treatment.
Figures 1, 17B:
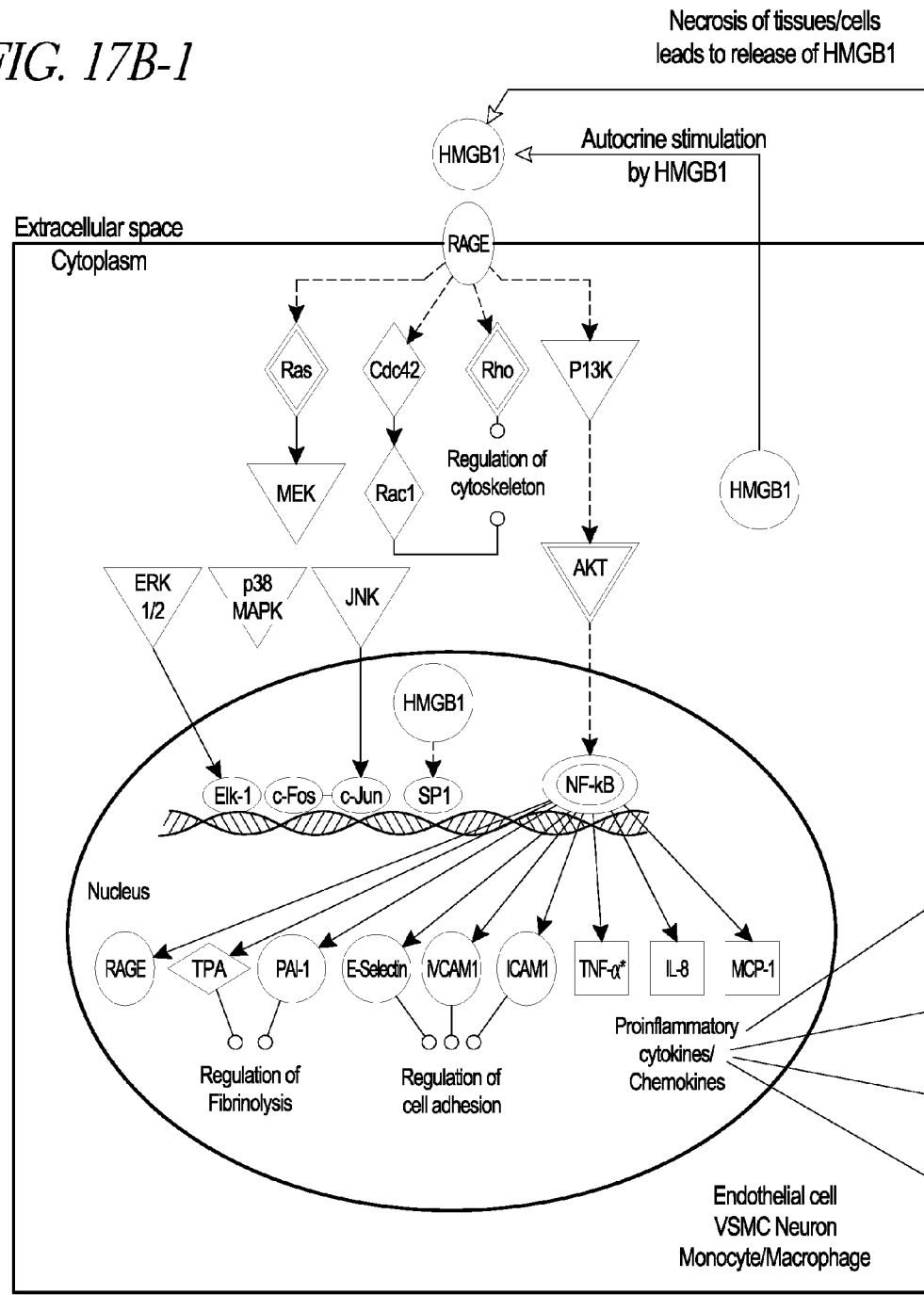
FIG. 1 shows that HMGB1 and RAGE are both upregulated in malignant mesothelioma (MM) cell lines.
Figure 17C:
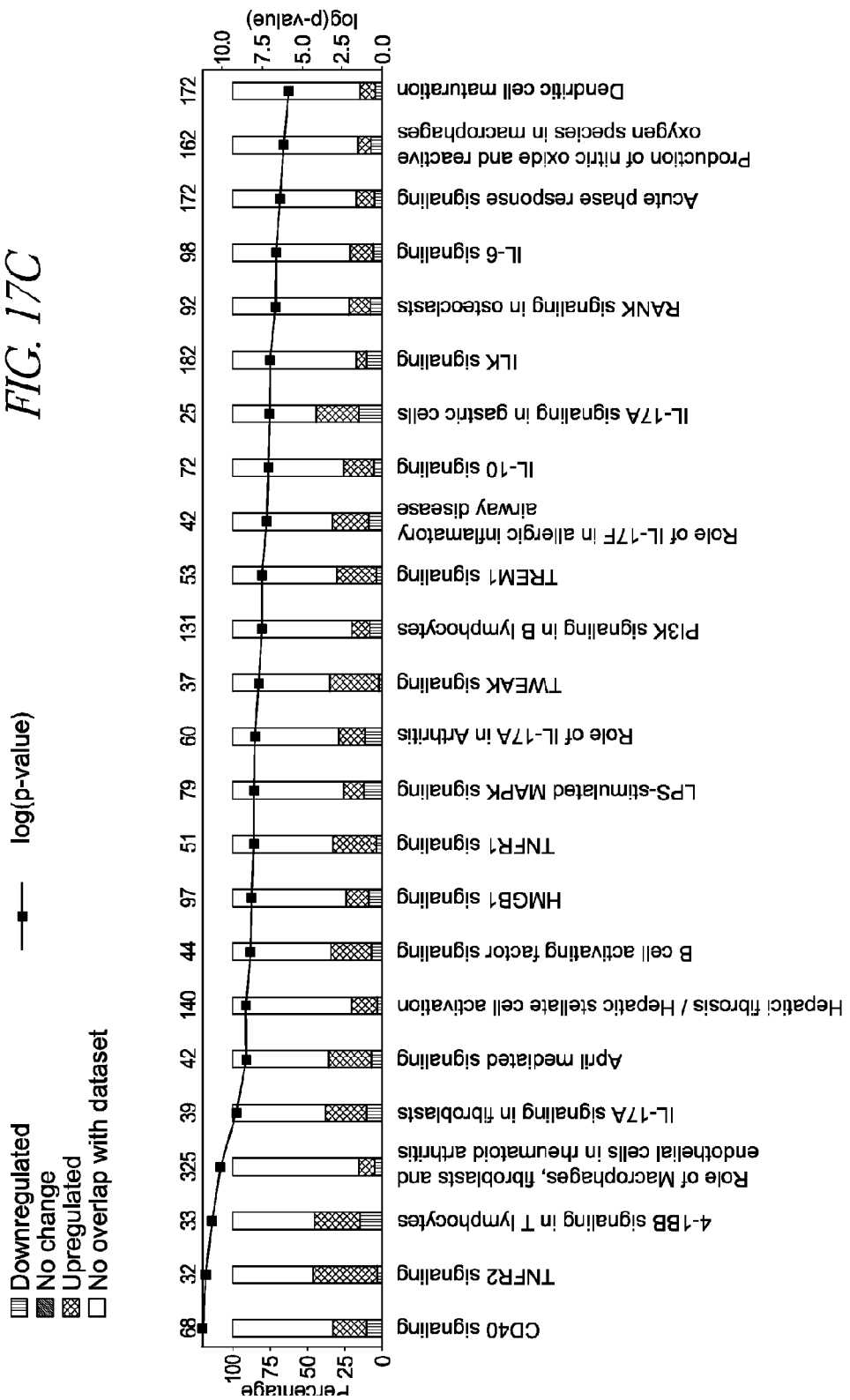

This analysis revealed that stimulation with HMGB1 enhanced the transcription of multiple genes controlled by the activation of NF-κB, and downstream genes. Genes such as TNF-α and IL-1α were up-regulated and genes downstream of TNFR1 and TNFR2 signaling were activated (FIG. 17). Activation of these genes has been linked to MM growth and invasion. These results indicate that HMGB1 sustains the main properties of the malignant phenotype (invasiveness and anchorage-independent growth) of MM cells.

Example 18

Aspirin Reduces HMGB1 Levels in Mice

BALB/c (BALB/cAnNCrl) female mice aged 3 to 4 weeks (Charles River Laboratories, Wilmington, Mass.) were housed and handled under aseptic conditions, in accordance with our institution's Institutional Animal Care and Use Committee (IACUC) guidelines. Mice were weighed and randomly assigned to negative control (vehicle), positive control (crocidolite) and treatment (crocidolite+aspirin) groups of 5 animals each. Aspirin was initially dissolved in dimethyl sulfoxide (DMSO; 5% by final volume) and then diluted to the desired concentration (5 mg/ml) with 0.5% carboxymethylcellulose in PBS (vehicle). Both aspirin (200 µl) and vehicle (200 µl) were orally administered via a 22-gauge feeding needle (Kent Scientific Co., Litchfield, Conn.) attached to a 1 cc syringe. Mice in the treatment group were first pre-treated with 25 mg/kg/day of aspirin for 3 days, and then injected i.p. with 1 mg crocidolite asbestos. After crocidolite injection, animals in the treatment group were given daily doses of aspirin (25 mg/kg/day in 200 µl volume. This is about 0.5 mg/day taken by each mouse, which is equivalent to 80-100 mg/day for human being) for 15 days, while animals in the control groups received 200 µl vehicle with the same schedule as the aspirin-treated group. Blood was drawn from the animals in all groups at days 1 and 5 after crocidolite injection; the sera was then collected and used for the detection of HMGB1 levels by ELISA (IBL International, Germany). Following completion of the treatment period, mice were euthanized according to IACUC regulations.

Figure 19A:
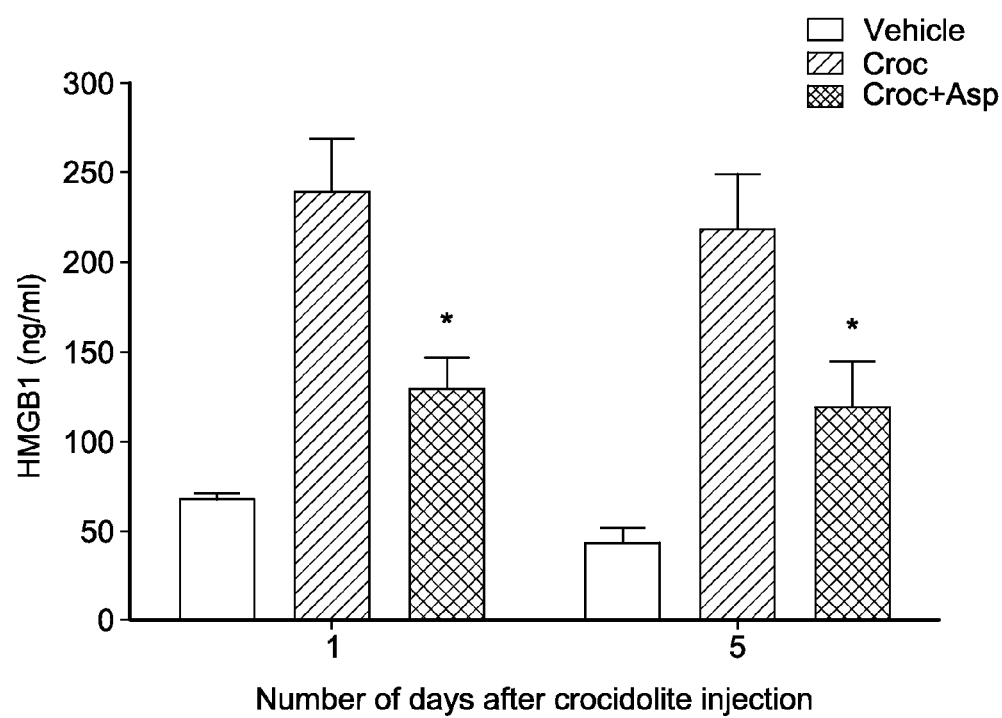
FIG. 19A-D shows that aspirin and BoxA are capable of reducing HMGB1 levels and reduce tumor growth in mice.

The results are set forth in FIG. 19A, and show that treatment with aspirin reduces levels of HMGB1 in blood serum.

Example 19

Aspirin Delays Human MM Cell Growth and Enhances Survival in Mice

In order to assess the ability of aspirin to reduce tumor growth, the following xenograft assay was performed.

Severe combined immunodeficient (NOD.CB17-SCID) female mice aged 6 to 8 weeks (Jackson Laboratories, Bar Harbor, Me.) were housed and handled under aseptic conditions, in accordance with our institution's Institutional Animal Care and Use Committee (IACUC) guidelines. Twenty SCID mice were injected intra peritoneum (i.p.) with $5 \times 10^5$ REN/luc cells suspended in 500 µl of PBS. Xenografts were visualized by luminescence after D-luciferin injection (150 mg/kg) using the In Vivo Imaging System (IVIS™, Xenogen Corp., Alameda, Calif.), with regions of interest (ROI) quantified as total photon counts by Living Image software (Xenogen Corp.). Four days were required for the formation of detectable tumor nodules by IVIS imaging. Mice were then weighed and randomly assigned to control (regular diet with no aspirin) and treatment (diet supplemented with aspirin) groups of ten animals each. Mice in the treatment group were first given a diet supplemented with 200 ppm aspirin for 34 consecutive days. The animals consumed approximately 2.5 g feed per day, containing approximately 500 µg aspirin. This is equivalent to a dose of 80-110 mg/day in humans on a 2000 kcal diet, based on the principle of nutrient density (Newmark, 1987). After 34 days, the animals were switched to a diet supplemented with 400 ppm aspirin, consuming approximately 1000 µg of aspirin per day, which is equivalent to 160-220 mg/day in humans. Control groups were fed diet without drug supplementation. Animals were weighted weekly for signs of weight loss. During the course of the experiment there was no difference in body weight between the control and treatment groups, suggesting that there is no toxicity in the treatment group. Tumor dimension was measured every 7th day as average radiance (photons/s/cm$^2$/sr). All animals died spontaneously probably due to tumor progression and ascite formation.

Figure 19B:
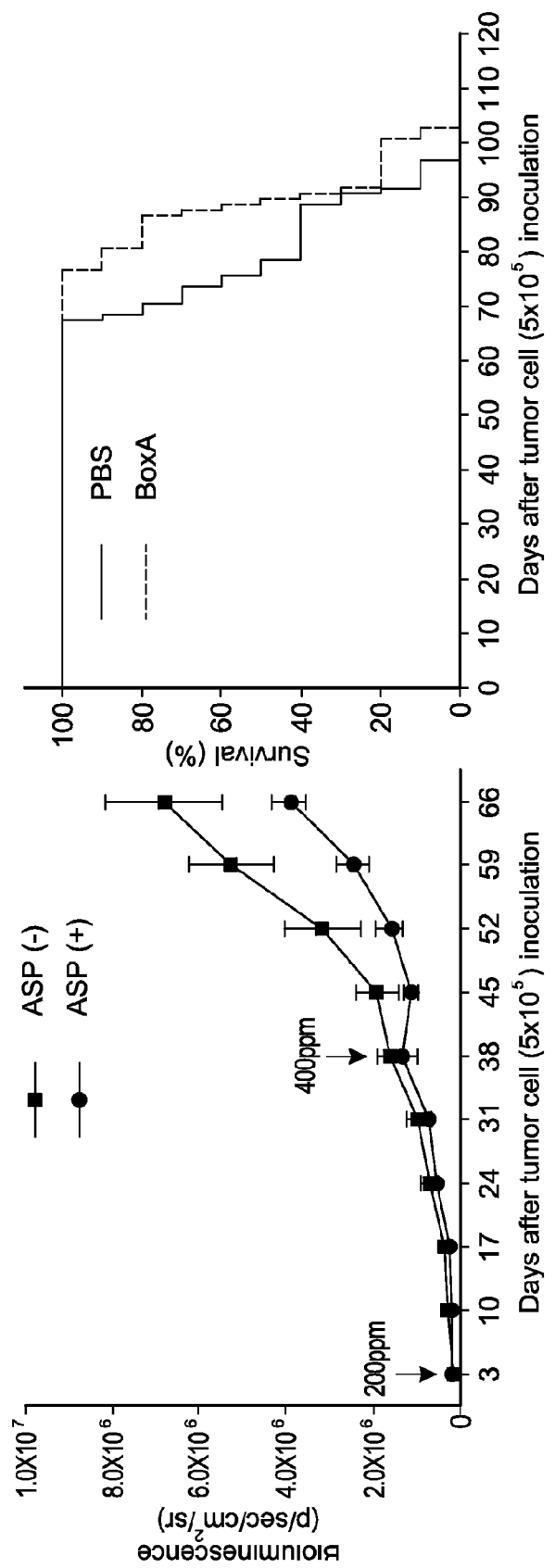

The results are set forth in FIG. 19B, and demonstrate that aspirin causes a delay in tumor growth and enhances survival.

Example 20

BoxA and Aspirin ReduceHMGB1 Levels in Mice

Severe combined immunodeficient (NOD.CB17-SCID) female mice aged 6 to 8 weeks (Jackson Laboratories, Bar Harbor, Me.) were housed and handled under aseptic conditions, in accordance with our institution's Institutional Animal Care and Use Committee (IACUC) guidelines. Thirty SCID mice were injected intra peritoneum (i.p.) with $5 \times 10^5$ REN/luc cells suspended in 500 µl of PBS. Mice were then weighed and randomly assigned to control (PBS-vehicle) and treatments (aspirin and BoxA) groups of ten animals each. Mice in the aspirin group were first given a diet supplemented with 200 ppm aspirin for 34 consecutive days. The animals consumed approximately 2.5 g feed per day, containing approximately 500 µg aspirin. This is equivalent to a dose of 80-110 mg/day in humans on a 2000 kcal diet, based on the principle of nutrient density (Newmark, 1987). After 34 days, the animals were switched to a diet supplemented with 400 ppm aspirin, consuming approximately 1000 µg of aspirin per day, which is equivalent to 160-220 mg/day in humans. Control groups were fed diet without drug supplementation. Animals in the BoxA group received 400 µg BoxA/injection i.p. three times a week for a total of 10 weeks (12 mg BoxA/mouse). The control groups received i.p. injections of 200 µl vehicle (PBS) with the same schedule as the BoxA-treated group. Two months after the beginning of the experiment, blood was drawn from animals in the control and treatments groups, the sera was then collected and used for the detection of HMGB1 levels by ELISA (IBL International, Germany).

Figure 19C:
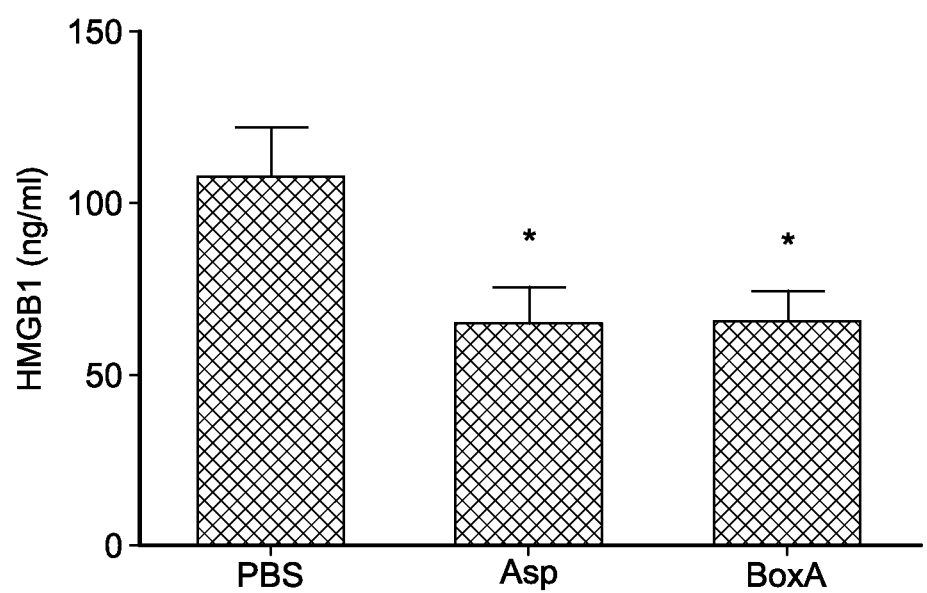

The results are set forth in FIG. 19C, and demonstrate that treatment with aspirin or BoxA reduces levels of HMGB1 in blood serum.

Example 21

BoxA Delays Human MM Cell Growth and Enhances Survival in Mice

In order to assess the ability of BoxA to reduce tumor growth, the following xenograft assay was performed.

Severe combined immunodeficient (NOD.CB17-SCID) female mice aged 6 to 8 weeks (Jackson Laboratories, Bar Harbor, Me.) were housed and handled under aseptic conditions, in accordance with our institution's Institutional Animal Care and Use Committee (IACUC) guidelines. Twenty SCID mice were injected intra peritoneum (i.p.) with $5 \times 10^5$ REN/luc cells suspended in 500 µl of PBS. Xenografts were visualized by luminescence after D-luciferin injection (150 mg/kg) using the In Vivo Imaging System (IVIS™, Xenogen Corp., Alameda, Calif.), with regions of interest (ROI) quantified as total photon counts by Living Image software (Xenogen Corp.). Four days were required for the formation of detectable tumor nodules by IVIS imaging. Mice were then weighed and randomly assigned to control (PBS-vehicle) and treatment (BoxA) groups of ten animals each. Each mouse in the treatment group received 400 µg BoxA/injection i.p. three times a week for a total of 10 weeks (12 mg BoxA/mouse). The control groups received i.p. injections of 200 µl vehicle (PBS) with the same schedule as the BoxA-treated group. Animals were weighted weekly for signs of weight loss. During the course of the experiment there was no difference in body weight between the control and treatment groups. Tumor dimension was measured every 7th day as average radiance (photons/s/cm$^2$/sr). The majority of the animals died spontaneously probably due to tumor progression and ascite formation, except for one mouse in the BoxA group, which died accidently from a blood draw.

Figure 19D:
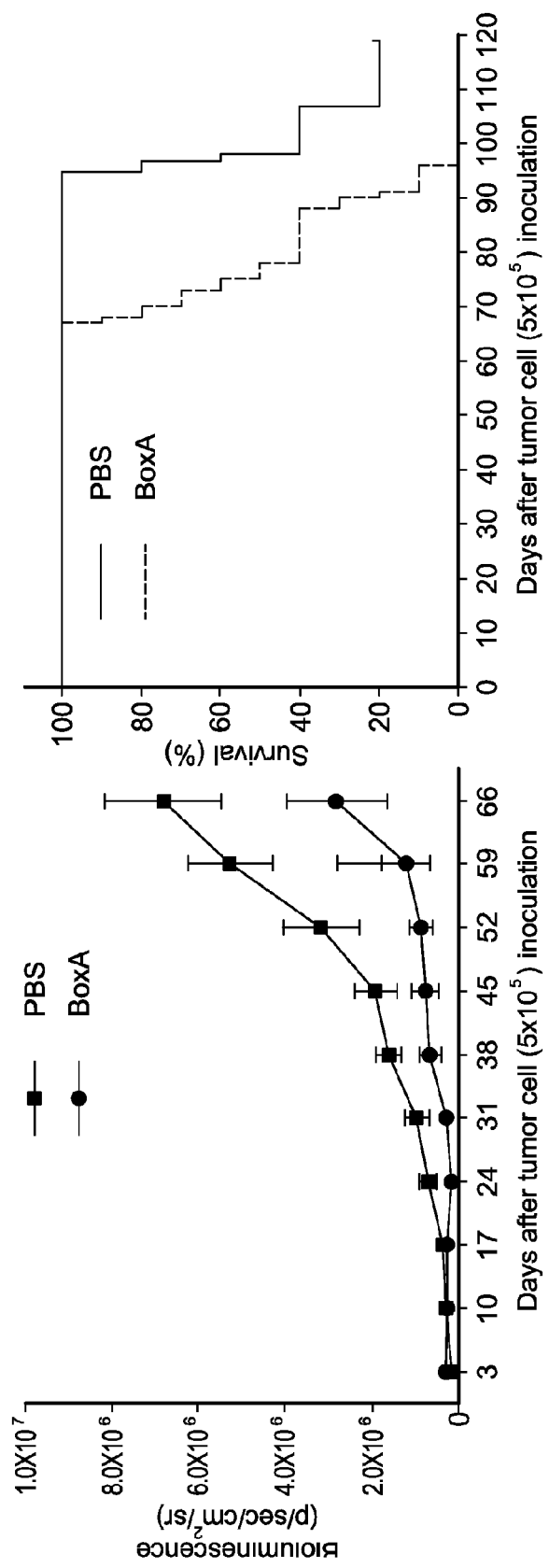

The results are set forth in FIG. 19D, and demonstrate that BoxA causes a delay in tumor growth and enhances survival.

What is claimed is:

1. A method of treating mesothelioma, the method comprising administering an amount of monoclonal antibody specific for High-Mobility Group Box 1 (HMGB1) to a subject having cancer, wherein the cancer is mesothelioma.

2. The method of claim 1, wherein the monoclonal antibody comprises a human constant region.

3. The method of claim 1, wherein the monoclonal antibody comprises a human variable region.

4. The method of claim 1, wherein the monoclonal antibody is chimeric and comprises a human constant region and a mouse variable region.

5. The method of claim 1, wherein the mesothelioma is malignant mesothelioma.

6. The method of claim 1, wherein the subject is human.

7. The method of claim 1 additionally comprising administering an anti-inflammatory compound to the subject.

8. The method of claim 1, wherein the amount of monoclonal antibody is about 1 μs to about 10,000 mg.

9. The method of claim 1, wherein the amount of monoclonal antibody is administered as a dosage of about 1 μg/kg to about 1000 mg/kg.

10. The method of claim 1, wherein the antibody binds to secreted HMGB1.

11. The method of claim 1, wherein the antibody is neither fused to a toxin nor conjugated to a toxin.

12. The method of claim 1, wherein the antibody is neither fused to a drug nor conjugated to a drug.

13. The method of claim 1, wherein the subject is a human who has been exposed to asbestos.

* * * * *

UNITED STATES PATENT AND TRADEMARK OFFICE
CERTIFICATE OF CORRECTION

PATENT NO. : 9,561,274 B2
APPLICATION NO. : 14/123607
DATED : February 7, 2017
INVENTOR(S) : Haining Yang Page 1 of 5

It is certified that error appears in the above-identified patent and that said Letters Patent is hereby corrected as shown below:

On the Title Page (Item (57), Abstract) at Line 2, Change "herewith" to --herein--.

In Column 1 (page 3, item (56)) at Line 32, Under Other Publications, change "activites`," to --activities`,--.

In Column 1 (page 3, item (56)) at Line 34, Under Other Publications, change "Pahse" to --Phase--.

In Column 1 (page 3, item (56)) at Line 55, Under Other Publications, change "`Matinib" to --`Imatinib--.

In Column 2 (page 3, item (56)) at Line 31, Under Other Publications, change "NΔ,N'Δ-" to --N",N'''- --.

In Column 2 (page 3, item (56)) at Line 33, Under Other Publications, change "(bromoacetannido)" to --(bromoacetamido)--.

In Column 1 (page 4, item (56)) at Line 17, Under Other Publications, change "`Artifical" to --`Artificial--.

In Column 1 (page 4, item (56)) at Line 33, Under Other Publications, change "checmical" to --chemical--.

In Column 1 (page 4, item (56)) at Line 46, Under Other Publications, change "rediced" to --reduced--.

In Column 1 (page 4, item (56)) at Lines 61-62, Under Other Publications, change "actication" to --activation--.

Signed and Sealed this
Thirtieth Day of May, 2017

Michelle K. Lee
*Director of the United States Patent and Trademark Office*

CERTIFICATE OF CORRECTION (continued)
U.S. Pat. No. 9,561,274 B2

In Column 2 (page 4, item (56)) at Line 9, Under Other Publications, change "discvoery`," to --discovery`,--.

In Column 2 (page 4, item (56)) at Line 12, Under Other Publications, change "ineractions`," to --interactions`,--.

In Column 2 (page 4, item (56)) at Line 14, Under Other Publications, change "sSolid" to --Solid--.

In Column 2 (page 4, item (56)) at Line 31, Under Other Publications, change "`Bacteriphage" to --`Bacteriophage--.

In Column 2 (page 4, item (56)) at Line 40, Under Other Publications, change "FcyR11`," to --FcyRII`,--.

In Column 2 (page 4, item (56)) at Line 53, Under Other Publications, change "antiboides:" to --antibodies:--.

In Column 2 (page 4, item (56)) at Line 57, Under Other Publications, change "Ann." to --Annu.--.

In Column 1 (page 5, item (56)) at Line 23, Under Other Publications, change "anlysis'," to --analysis',--.

In Column 1 (page 5, item (56)) at Line 28, Under Other Publications, change "regualtion`," to --regulation`,--.

In Column 1 (page 5, item (56)) at Line 68, Under Other Publications, change "encdoed" to --encoded--.

In Column 2 (page 5, item (56)) at Line 4, Under Other Publications, change "Immunogloblllin" to --Immunoglobulin--.

In Column 2 (page 5, item (56)) at Line 11, Under Other Publications, change "complementaritu" to --complementarity--.

In Column 2 (page 5, item (56)) at Line 28, Under Other Publications, change "Ann." to --Annu.--.

In Column 2 (page 5, item (56)) at Line 31, Under Other Publications, change "Reidirect" to --Redirect--.

In Column 2 (page 5, item (56)) at Line 48, Under Other Publications, change "Backcone" to --Backbone--.

In Column 2 (page 5, item (56)) at Line 57, Under Other Publications, change "Vuris" to --Virus--.

CERTIFICATE OF CORRECTION (continued)
U.S. Pat. No. 9,561,274 B2

In the Drawings

Sheet 42 of 49 (FIG. 17) at Line 12 (approx.), Change "Bacteriocidal" to --Bactericidal--.

Sheet 43 of 49 (FIG. 17C) at Line 13, Change "inflamatory" to --inflammatory--.

Sheet 43 of 49 (FIG. 17C) at Line 22, Change "Hepatici" to --Hepatic--.

In the Specification

In Column 1 at Line 8, Change "No." to --Nos.--.

In Column 3 at Line 16, Change "an another" to --another--.

In Column 6 at Line 52, Change "Actynomicin" to --Actinomycin--.

In Column 6 at Line 60, Change "inhibitors" to --inhibitors.--.

In Column 7 at Line 10, Change "Image]" to --ImageJ--.

In Column 10 at Lines 50-51, Change "HMGB 1" to --HMGB1--.

In Column 10 at Line 54, Change "HMGB1mAb," to --HMGB1 mAb,--.

In Column 12 at Line 1, Change "$s^1$," to --$s^{-1}$,--.

In Column 12 at Line 5, Change "$M^-s^{-1}$," to --$M^{-1}s^{-1}$,--.

In Column 13 at Line 49, Change "molecule" to --molecule.--.

In Column 13 at Line 67, Change "fusions" to --fusions.--.

In Column 16 at Line 56, Change "$V_L$CDRs" to --$V_L$ CDRs--.

In Column 16 at Line 57, Change "$V_L$CDRs." to --$V_H$CDRs.--.

In Column 16 at Line 59, Change "$V_L$CDRs" to --$V_L$ CDRs--.

In Column 23 at Lines 63-64, Change "transcription translation" to --transcription/translation--.

In Column 25 at Line 7, Change "Ann." to --Annu.--.

In Column 25 at Line 9, Change "Ann." to --Annu.--.

In Column 28 at Line 48, Change "tenoposide." to --teniposide.--.

CERTIFICATE OF CORRECTION (continued)

U.S. Pat. No. 9,561,274 B2

In Column 28 at Lines 48-49, Change "colchicin," to --colchicine,--.

In Column 28 at Lines 50-51, Change "dehydrotestosterone," to --dihydrotestosterone,--.

In Column 28 at Line 55, Change "decarbazine)," to --dacarbazine),--.

In Column 28 at Line 56, Change "thioepa" to --thiotepa--.

In Column 28 at Line 57, Change "(BSNU)" to --(BCNU)--.

In Column 28 at Line 58, Change "cyclothosphamide," to --cyclophosphamide,--.

In Column 30 at Line 34, Change "a" to --A--.

In Column 34 at Line 9, Change "amine" to --amine.--.

In Column 36 at Line 18, Change "onyphenbutazone," to --oxyphenbutazone,--.

In Column 36 at Line 21, Change "etofenamice" to --etofenamate--.

In Column 36 at Line 26, Change "oxprozin)," to --oxaprozin),--.

In Column 36 at Line 45, Change "quinozolinone" to --quinazolinone--.

In Column 42 at Line 27, Change "polysaccarides" to --polysaccharides--.

In Column 42 at Line 28, Change "chitosane" to --chitosan--.

In Column 42 at Line 57, Change "J" to --J.--.

In Column 47 at Line 45, Change "Biochemica" to --Biochemika--.

In Column 49 at Line 21, Change "Pharmacopia" to --Pharmacopeia--.

In Column 52 at Line 49, Change "albumin" to --albumin.--.

In Column 54 at Line 26, Change "(Ferment as," to --(Fermentas,--.

In Column 54 at Line 62, Change "-a-" to -- -α- --.

In Column 56 at Line 64, Change "down-regulation" to --Down-regulation--.

In Column 57 at Line 3, Change "HMGBI-" to --HMGB1- --.

In Column 57 at Line 62. After "instruction." insert --Both assays were done in--.

CERTIFICATE OF CORRECTION (continued)
U.S. Pat. No. 9,561,274 B2

In Column 59 at Line 21, Change "Matinib" to --Imatinib--.

In Column 61 at Line 50, Change "$10_5$" to --$10^5$--.

In Column 63 at Line 57, Change "ReduceHMGB1" to --Reduce HMGB1--.

In the Claims

In Column 68 at Line 45 (in Claim 8), Change "μs" to --μg--.

SEQUENCE LISTING

<160> NUMBER OF SEQ ID NOS: 3

<210> SEQ ID NO 1
<211> LENGTH: 215
<212> TYPE: PRT
<213> ORGANISM: Homo sapiens

<400> SEQUENCE: 1

```
Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
             20                  25                  30

Asp Ala Ser Val Asn Phe Ser Glu Phe Ser Lys Lys Cys Ser Glu Arg
         35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
            195                 200                 205

Glu Glu Asp Asp Asp Asp Glu
210                 215
```

<210> SEQ ID NO 2
<211> LENGTH: 215
<212> TYPE: PRT
<213> ORGANISM: Homo sapiens

<400> SEQUENCE: 2

```
Met Gly Lys Gly Asp Pro Lys Lys Pro Thr Gly Lys Met Ser Ser Tyr
 1               5                  10                  15

Ala Phe Phe Val Gln Thr Cys Arg Glu Glu His Lys Lys Lys His Pro
             20                  25                  30

Asp Ala Ser Val Asn Phe Ser Glu Phe Ser Lys Lys Cys Ser Glu Arg
         35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Leu Pro Ser Ala Phe Phe Leu Phe Cys Ser Glu Tyr Arg Pro Lys
```

```
                100               105               110
Ile Lys Gly Glu His Pro Gly Leu Ser Ile Gly Asp Val Ala Lys Lys
            115               120               125

Leu Gly Glu Met Trp Asn Asn Thr Ala Ala Asp Asp Lys Gln Pro Tyr
130             135               140

Glu Lys Lys Ala Ala Lys Leu Lys Glu Lys Tyr Glu Lys Asp Ile Ala
145             150               155               160

Ala Tyr Arg Ala Lys Gly Lys Pro Asp Ala Ala Lys Lys Gly Val Val
            165               170               175

Lys Ala Glu Lys Ser Lys Lys Lys Glu Glu Glu Glu Asp Glu Glu
            180               185               190

Asp Glu Glu Asp Glu Glu Glu Glu Asp Glu Glu Asp Glu Glu Asp
            195               200               205

Glu Glu Asp Asp Asp Asp Glu
            210               215

<210> SEQ ID NO 3
<211> LENGTH: 77
<212> TYPE: PRT
<213> ORGANISM: Homo sapiens

<400> SEQUENCE: 3

Pro Thr Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75
```